US012747264B2

(12) United States Patent
Lampe et al.

(10) Patent No.: US 12,747,264 B2
(45) Date of Patent: Sep. 29, 2026

(54) SELF-ASSEMBLING PEPTIDES AND HYDROGELS

(71) Applicant: UNIVERSITY OF VIRGINIA PATENT FOUNDATION, Charlottesville, VA (US)

(72) Inventors: Kyle Jay Lampe, Charlottesville, VA (US); James D. Tang, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1215 days.

(21) Appl. No.: 17/290,050

(22) PCT Filed: Oct. 31, 2019

(86) PCT No.: PCT/US2019/059052
§ 371 (c)(1),
(2) Date: Apr. 29, 2021

(87) PCT Pub. No.: WO2020/092705
PCT Pub. Date: May 7, 2020

(65) Prior Publication Data

US 2022/0267373 A1 Aug. 25, 2022

Related U.S. Application Data

(60) Provisional application No. 62/813,893, filed on Mar. 5, 2019, provisional application No. 62/753,436, filed on Oct. 31, 2018.

(51) Int. Cl.

| | |
|---|---|
| ***C07K 7/06*** | (2006.01) |
| ***A61K 9/06*** | (2006.01) |
| ***A61L 27/22*** | (2006.01) |
| ***A61L 27/52*** | (2006.01) |
| ***A61P 17/02*** | (2006.01) |
| ***C12N 5/00*** | (2006.01) |

(52) U.S. Cl.
CPC .................. *C07K 7/06* (2013.01); *A61K 9/06* (2013.01); *A61L 27/227* (2013.01); *A61L 27/52* (2013.01); *A61P 17/02* (2018.01); *C12N 5/0018* (2013.01); *A61L 2430/34* (2013.01); *C12N 2533/20* (2013.01)

(58) Field of Classification Search
None
See application file for complete search history.

(56) References Cited

U.S. PATENT DOCUMENTS

| | | | |
|---|---|---|---|
| 5,807,683 A | 9/1998 | Brenner | |
| 2014/0314790 A1 | 10/2014 | D'Adamio et al. | |

FOREIGN PATENT DOCUMENTS

| | | | |
|---|---|---|---|
| JP | 2007217330 * | 1/2007 | |
| WO | 2001/024810 A1 | 4/2001 | |
| WO | WO-2012119989 A2 * | 9/2012 | .............. A61P 35/00 |
| WO | WO-2013049830 A2 * | 4/2013 | ............... C07K 7/06 |
| WO | 2016/187508 A2 | 11/2016 | |
| WO | 2018/093449 A1 | 5/2018 | |

OTHER PUBLICATIONS

Lin et al. (Inhibition of Cathepsin D by synthetic oligopeptides The journal of biological chemistry, vol. 254, No. 23, 1979).*
GenBank ACA84095.1 (https://www.ncbi.nlm.nih.gov/protein/ACA84095> accessed Nov. 29, 2024).*
Xu et al. (Nat Commun. 14,4163(2023).*
International Search Report and Written Opinion dated Feb. 6, 2020 in related International Application No. PCT/US2019/059052.

* cited by examiner

*Primary Examiner* — Tara L Martinez
(74) *Attorney, Agent, or Firm* — Dinsmore & Shohl LLP

(57) ABSTRACT

Novel self-assembling pentapeptides and peptides containing such self-assembling pentapeptides, self-assembled hydrogels, and methods of making and using the same are described. These pentapeptides, and peptides containing such pentapeptides, self-assemble under physiological conditions (e.g., in a physiological buffer under biologically acceptable conditions (e.g., pH≈6-11)) into long fibrils with sequence-dependent fibrillary morphologies. The hydrogels comprise one or more these pentapeptides which make up the 3-dimensional nanofibrous network of the hydrogel structure. The hydrogels are shear-thinning hydrogels that have high storage moduli and high rates of recovery after destruction. These hydrogels are useful in various applications, including but not limited to, scaffolds for tissue engineering, 2-dimensional (2-D) and 3-dimensional (3-D) cell cultures, drug delivery and encapsulation of therapeutic agents (cells, molecules, drugs, compounds), injectables (including those that gel in situ, such as hemostatic compositions), hemostatic agents, wound dressings, pharmaceutical carriers or vehicles, cell transplantation, cell storage, virus culture, and virus storage.

2 Claims, 45 Drawing Sheets

Specification includes a Sequence Listing.

FIG. 1 A
| Sequence | pI |
|---|---|
| KYFIL | 8.50 |
| AYFIL | 5.28 |
| KYFAL | 8.50 |
| KYFIV | 8.50 |
| KYFIA | 8.50 |
| KAFIL | 8.86 |
| KYAIL | 8.50 |
FIG. 1 B
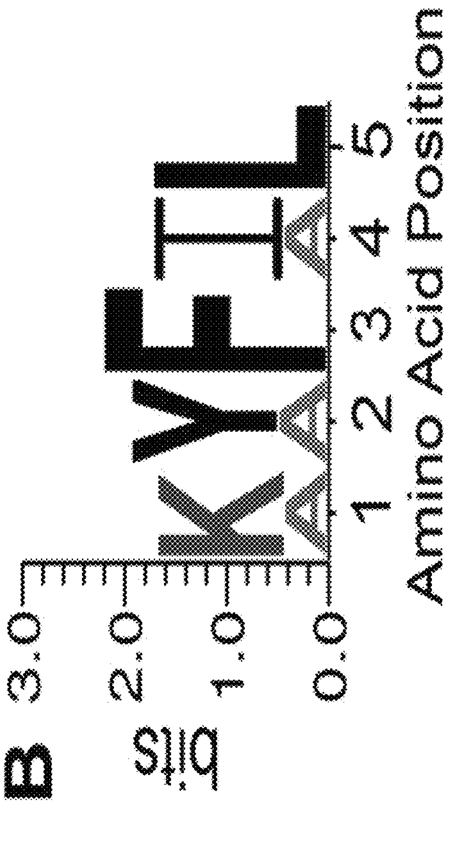
FIG. 1 C
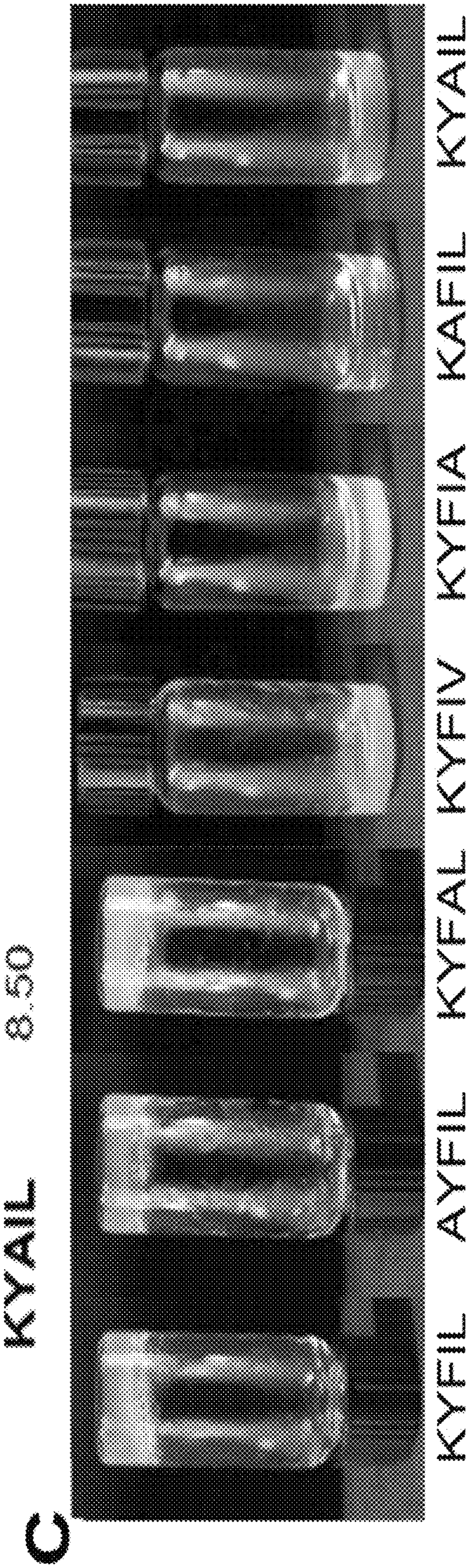

C

D

E

F

A

B

SELF-ASSEMBLING PEPTIDES AND HYDROGELS

CROSS-REFERENCE TO RELATED APPLICATION

This application is a National Phase Application of International Application No. PCT/US2019/059052, filed Oct. 31, 2019 and—claims the benefit of U.S. Provisional Application No. 62/753,436 filed Oct. 31, 2018 and claims benefit of U.S. Provisional Application No. 62/813,893 filed Mar. 5, 2019, the entire contents of which are incorporated herein by reference.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created Nov. 19, 2021, is named "SEQUENCE_LISTING_UVA0006PA" and is 4 KB bytes in size.

FIELD

The present disclosure generally relates to novel self-assembling pentapeptides and peptides containing such self-assembling pentapeptides, self-assembled hydrogels, and methods of making and using the same. The instantly-disclosed pentapeptides and peptides containing such self-assembling pentapeptides self-assemble under physiological conditions (e.g., in a physiological buffer under biologically acceptable conditions (e.g., pH of about 6-11, including pH≈7.4)) into long fibrils with sequence-dependent fibrillary morphologies. The instantly-disclosed hydrogels comprise one or more the instantly-disclosed pentapeptides and peptides containing such self-assembling pentapeptides, which make up the 3-dimensional nanofibrous network of the hydrogel structure. The instantly disclosed hydrogels are shear thinning hydrogels that have high storage moduli and high rates of recovery after destruction. These hydrogels are useful in various applications, including but not limited to, scaffolds for tissue engineering, 2-dimensional (2-D) and 3-dimensional (3-D) cell cultures, drug delivery and encapsulation of therapeutic agents (cells, molecules, drugs, compounds), injectables (including those that gel in situ, such as hemostatic compositions), hemostatic agents, wound dressings, pharmaceutical carriers or vehicles, cell transplantation, cell storage, virus culture, and virus storage.

BACKGROUND

An attractive approach to tissue regeneration relies on biomaterials that can mimic features of the native extracellular matrix (ECM), including proteolytic remodeling, cell-adhesion, and mechanical properties, while providing suitable induction for specific differentiation. Tissue engineering using biologically relevant hydrogel culture systems may improve regeneration as they have a broad range of structural flexibility, biological activity, and similar mechanics to native tissue, leading to more physiologically relevant cell behavior. However, an appropriate microenvironment that retains relevant biological and structural functions remains to be developed.

Hydrogels are a promising class of biomaterials composed of water-swollen polymeric networks that mimic several biological and mechanical properties of the naturally compliant human brain tissue. Despite the many technological advances in recreating the cellular and matrix microenvironments found in vivo, few materials exist that capture the highly dynamical and adaptable nature of the native ECM. Furthermore, even fewer materials have been designed that 1) are simple and inexpensive to synthesize, 2) gel in response to cytocompatible stimuli such as small shifts in pH or temperature, and 3) support and regulate cell function as a substitute for their normal physiological microenvironment. Transplanting cells, such as stem cells, may improve behavioral recovery following an injury or insult, or during chronic or degenerative diseases. Further, recent developments in neural tissue regeneration applications require direct injection of cells to the stroke region. However, transplant cell viability is known to be poor, and this is at least in part due to negative effects of damage done during the process of injection where cells undergo stresses such as non-physiological elongational flow and superphysiological shear forces. And thus, fabricating injectable and self-healing hydrogels to serve as cell carriers for transplantation therapies will increase the percentage of live cells post-injection into ischemic tissue for therapeutic repair.

Self-assembling oligopeptides are attractive candidates for biocompatible three-dimensional scaffolds that can support and regulate cell function as a substitute for their normal physiological microenvironment. In particular, peptide-based hydrogel materials are generally cytocompatible, and are inherently more physiologically relevant as they allow for cellular remodeling and can promote cell viability. However, there are several challenges that currently limits the expansion and applications of these short peptides in tissue engineering and regenerative medicine. First, there are relatively few examples of these oligopeptides that exist beyond the derivation or analogs of the well-established diphenylalanine peptide sequence. While these dipeptides are able to form robust hydrogel systems, the inherent hydrophobicity of the sequence limits their solubility and thereby, extension of their application. Second, the relatively few oligopeptides which have been studied are derived by sequence mapping onto relevant biological systems that have already been known to self-assemble into a variety of nanostructures. Thus, there exists an ongoing need for self-assembling oligopeptides that can form biocompatible three-dimensional scaffolds that address these problems.

SUMMARY

Accordingly, the present disclosure is directed to a novel class of self-assembling pentapeptides and peptides containing such self-assembling pentapeptides capable of forming robust nanofiber hydrogels upon mixing under physiological conditions. These supramolecular assembly-based hydrogels can serve as cell-delivery vehicles and are cost-effective and simple to synthesize. The instantly disclosed hydrogels, which are referred to as rapidly assembling pentapeptides for injectable delivery (RAPID) hydrogels, can mitigate the damaging effects of extensional flow during syringe injections.

As such, in aspects, the present disclosure provides novel self-assembling pentapeptides and peptides containing such self-assembling pentapeptides, self-assembled hydrogels, and methods of making and using the same. The instantly-disclosed pentapeptides, as well as longer peptides containing such self-assembling pentapeptides, self-assemble under physiological conditions (e.g., in a physiological buffer under biologically acceptable conditions (pH≈7.4)) into long fibrils with sequence-dependent fibrillary morphologies. The instantly-disclosed RAPID hydrogels comprise one or more the instantly-disclosed pentapeptides, and/or peptides containing such self-assembling pentapeptides, which make up the 3-dimensional nanofibrous network of the hydrogel structure. Importantly, these hydrogels are characterized by a "reversible" hydrogel matrix, which means that the 3-dimensional nanofibrous matrix is shear thinning (i.e., the viscosity decreases with an increase in the rate of shear stress applied to the gel), but recovers quickly after gel destruction. As such, these hydrogels are useful in various applications, including but not limited to, scaffolds for tissue engineering, 2-dimensional (2-D) and 3-dimensional (3-D) cell cultures, drug delivery and encapsulation of therapeutic agents (cells, molecules, drugs, compounds), injectables (including those that gel in situ, such as hemostatic compositions), hemostatic agents, wound dressings, pharmaceutical carriers or vehicles, cell transplantation, cell storage, virus culture, and virus storage.

In aspects, the present disclosure is directed to a peptide comprising an amino acid sequence $(X_1\text{-}X_2\text{-}F\text{-}X_3\text{-}L)_a$, wherein $X_1$ is a positively charged or an aliphatic amino acid, $X_2$ is an aliphatic or an aromatic amino acid, $X_3$ is a hydrophobic amino acid, and a is 1 or 2. In aspects, the present disclosure is directed to a 6-mer, 7-mer, 8-mer, 9-mer, or 10-mer peptide comprising an amino acid sequence comprising $X_1\text{-}X_2\text{-}F\text{-}X_3\text{-}L$, wherein $X_1$ is a positively charged or an aliphatic amino acid, $X_2$ is an aliphatic or an aromatic amino acid, and $X_3$ is a hydrophobic amino acid. In aspects of the above-referenced peptides, $X_1$ is an amino acid residue selected from the group consisting of K, A, and V, $X_2$ is an amino acid residue selected from the group consisting of Y and A, and $X_3$ is an amino acid residue selected from I and A. In aspects, $X_1$ is an amino acid residue selected from the group consisting of K and A, $X_2$ is an amino acid residue selected from the group consisting of Y and A, and $X_3$ is an amino acid residue selected from I and A. In aspects of the above-referenced peptides, the peptide has an uncharged C-terminus. In aspects of the above-referenced peptides, the peptide is C-terminally amidated. In aspects of the above-referenced peptides, the peptide is capable of self-assembling and forming robust nanofiber hydrogels (e.g., in aspects, upon mixing under physiological conditions as described herein). In aspects, the present disclosure is directed to a nucleic acid sequence (e.g., DNA or RNA) encoding one or more peptides of the present disclosure.

In aspects, the present disclosure is directed to a peptide comprising an amino acid sequence set forth in SEQ ID NO: 1 (KYFIL), SEQ ID NO: 2 (AYFIL), SEQ ID NO: 3 (KYFAL), SEQ ID NO: 4 (KAFIL), SEQ ID NO: 5 (KYAIL), SEQ ID NO: 6 (KYFIA), SEQ ID NO: 7 (KYFIV), SEQ ID NO: 8 (VYFIL), SEQ ID NO: 9 (RYFIL), SEQ ID NO: 10 (KYFILKYFIL), SEQ ID NO: 11 (AYFILAYFIL), SEQ ID NO: 12 (KYFALKYFAL), SEQ ID NO: 13 (KAFILKAFIL), SEQ ID NO: 14 (KYAILKYAIL), SEQ ID NO: 15 (KYFIAKYFAI), SEQ ID NO: 16 (KYFIVKYFIV), SEQ ID NO: 17 (VYFILVYFIL) or SEQ ID NO: 18 (RYFILRYFIL). In aspects, the present disclosure is directed to a 6-mer, 7-mer, 8-mer, 9-mer, or 10-mer peptide having an amino acid sequence comprising SEQ ID NO: 1 (KYFIL), SEQ ID NO: 2 (AYFIL), SEQ ID NO: 3 (KYFAL), SEQ ID NO: 4 (KAFIL), SEQ ID NO: 5 (KYAIL), SEQ ID NO: 6 (KYFIA), SEQ ID NO: 7 (KYFIV), SEQ ID NO: 8 (VYFIL) or SEQ ID NO: 9 (RYFIL). In aspects of the above-referenced peptides, the peptide has an uncharged C-terminus. In aspects of the above-referenced peptides, the peptide is C-terminally amidated. In aspects of the above-referenced peptides, the peptide is capable of self-assembling and forming robust nanofiber hydrogels (e.g., in aspects, upon mixing under physiological conditions as described herein). In aspects, the present disclosure is directed to a nucleic acid sequence (e.g., DNA or RNA) encoding one or more peptides of the present disclosure.

In additional aspects, the present disclosure is directed to a hydrogel composition comprising: an aqueous dispersion phase comprising an aqueous dispersion medium; and at least one peptide according to the present disclosure, wherein the hydrogel is formed by self-assembly of said at least one peptide in said aqueous dispersion phase. In aspects, the aqueous dispersion medium is physiologically acceptable. In further aspects, the aqueous dispersion medium comprises one or more salts. In even further aspects, the aqueous dispersion medium comprises one or more salts selected from the group consisting of $(NH_4)_2SO_4$, $Na_2SO_4$, NaCl, KCl and $CH_3COONH_4$. In aspects of the above-referenced hydrogel compositions, the hydrogel has a pH from about 7 to about 11, from about 7 to about 8, or about 7.4. In aspects of the above-referenced hydrogel compositions, the at least one peptide is present in said hydrogel at a level of from about 0.1% by weight to about 5% by weight, based upon the total weight of the hydrogel. In aspects of the above-referenced hydrogel compositions, the at least one peptide is present in said hydrogel at a level of from about 1.5% by weight to about 3% by weight, based upon the total weight of the hydrogel. In aspects of the above-referenced hydrogel compositions, the hydrogel has a storage modulus of at least 50 Pa. In aspects of the above-referenced hydrogel compositions, the hydrogel has a storage modulus of from about 50 Pa to about 17,000 Pa. In aspects of the above-referenced hydrogel compositions, the hydrogel has a % recovery of at least 80% within 1 min. In aspects of the above-referenced hydrogel compositions, the hydrogel is a shear-thinning hydrogel. In aspects of the above-referenced hydrogel compositions, the hydrogel comprises peptide nanofibers, said nanofibers comprising said at least one peptide. In aspects of the above-referenced hydrogel compositions, the hydrogel further comprises an active agent. In aspects of the above-referenced hydrogel compositions, the hydrogel further comprises a cell.

In aspects, the present disclosure is directed to a method of preparing the instantly-disclosed hydrogel compositions, the method comprising the steps of: (i) preparing an aqueous solution of said at least one peptide; and (ii) adjusting the pH of said aqueous solution such that hydrogel formation occurs. In aspects, the pH is adjusted to about 7-11. In aspects, the pH is adjusted to about 7-8. In aspects, the pH is adjusted to about 7.4. In aspects, the least one peptide is present in said solution at a level of from about 0.1% by weight to about 5% by weight, based upon the total weight of the solution. In aspects, least one peptide is present in said solution at a level of from about 1.5% by weight to about 3.0% by weight, based upon the total weight of the solution.

In other aspects, the present disclosure is directed to a liquid hydrogel precursor composition comprising: an aqueous dispersion phase comprising an aqueous dispersion medium; and at least one peptide as disclosed herein, wherein said composition is capable of being induced to form a hydrogel by self-assembly of said at least one peptide in said aqueous dispersion phase.

In additional aspects, the present disclosure is directed to a pharmaceutical composition comprising a hydrogel as disclosed herein and a pharmaceutically acceptable vehicle.

In aspects, the present disclosure is directed to a cell-supporting medium comprising a hydrogel composition as disclosed herein and at least one cell In further aspects, the present disclosure is directed to a method of treating an individual suffering from a medical condition characterized by tissue loss/damage, the method comprising forming a hydrogel as disclosed herein, wherein said forming is conducted (a) at a treatment site of an individual in need of such treatment, or (b) in vitro followed by transferring said hydrogel to said treatment site.

In aspects, the present disclosure is directed to a method of preparing a cell supporting medium as disclosed herein, the method comprising the steps of: (i) contacting a hydrogel as disclosed herein with at least one cell; and (iv) exposing the hydrogel to conditions such that the at least one cell is supported on and/or in the hydrogel, thereby forming a cell-supporting medium.

In additional aspects, the present disclosure is directed to a method of delivering an active agent to an individual, said method comprising administering a hydrogel composition according to some aspects, wherein the active agent is encapsulated in the hydrogel.

These and additional embodiments and features of the presently-disclosed subject matter will be clarified by reference to the figures and detailed description set forth herein.

It is understood that both the preceding summary and the following detailed description are exemplary and are intended to provide further explanation of the disclosure as claimed. Neither the summary nor the description that follows is intended to define or limit the scope of the disclosure to the particular features mentioned in the summary or description.

BRIEF DESCRIPTION OF THE DRAWINGS

FIGS. 1A-C are directed to pentapeptide sequences investigated in this study. FIG. 1A shows each sequence examined (KYFIL (SEQ ID NO: 1), AYFIL (SEQ ID NO: 2), KYFAL (SEQ ID NO: 3), KAFIL (SEQ ID NO: 4), KYAIL (SEQ ID NO: 5), KYFIA (SEQ ID NO: 6), and KYFIV (SEQ ID NO: 7)), along with its theoretical isoelectric point (pI). In aspects, all peptides are C-terminally amidated. FIG. 1B depicts a sequence logo that highlights the order and predominance of amino acids within pentapeptide analogs that gel under any pH condition. The sequence profiling suggests that Phe (F) and Leu (L) must be conserved for gelation. FIG. 1C shows images demonstrating that when peptides are dissolved in PBS at pH 7.4 and 1.5 wt %, the KYFIL, AYFIL, and KYFAL pentapeptides form hydrogels, whereas other sequences do not gel under these conditions; note that KAFIL can gel at pH>10.

FIG. 3A depicts representative structures of the simulated pentapeptide sequence, KYFIL. Spatiotemporal evolution of peptide assembly is demonstrated from the simulation trajectory of the peptides at 50 ns intervals as the molecules assemble into large clusters on the time scale of 200 ns. FIG. 3B shows density functions representing the clustering propensity of different pentapeptide systems over time. At the end of the 200 ns simulation, KYFIL has the least number of distinct clusters and largest number of peptides per cluster, versus other peptide sequences (insets). Representative snapshots of the peptides near 200 ns.

FIG. 4A shows histograms that depict the predominant conformations exhibited by the polypeptide are β-turns and "other" structures. For all sequences, there is an absence of α-helical structures, consistent with our experimental results. In addition, β-turn structures are prevalent with β-strand and bridge structures. A significant shift from strand to bridge occurs in the character of the β structure in the nongelling sequence, KYFIV. FIG. 4B shows representative snapshots taken at 180 and 177 ns for KYFIL and KYFIV, respectively, illustrating sequence-dependent conformational states of the pentapeptides. The peptides can be seen to be a mixture of helices and coils; the secondary structures are labeled in this view with α-helices colored purple, 310 helices blue, β-strands yellow, the β-turn motif cyan, and irregular coil regions white. These trajectory frames illustrate the formation of β-sheet regions within the two peptide systems, with more pronounced populations of β-sheet conformations present in KYFIL versus KYFIV.

FIG. 6A shows storage and loss moduli as determined from the linear viscoelastic region (LVE) taken from strain sweeps at a constant frequency of 1 hz of 1.5 and 3 wt % hydrogels at pH 7.4. Hydrogels were formed in situ in an epitube and then pipetted onto the rheometer platform. Hydrogel stiffness can be tuned by concentration and peptide sequence variation. The inset is a magnification of the G' and G" for KAFIL and KYFAL hydrogels. FIG. 6B depicts Storage moduli taken from the LVE from strain sweeps at a constant frequency of 1 hz of 1.5 wt % hydrogels at different pH conditions of 4.6, 7.4, and 10.6. The mechanical properties of the hydrogel are dependent on pH, where all peptide sequences are very weak gels (G'<80 Pa) in acidic conditions and form robust hydrogels at pHs of about 7 to about 11 (e.g., pH 7.4 and 10.6). FIG. 6C depicts the results of evaluation of hydrogel forming sequences under shear flow to determine their shear-thinning properties. The apparent viscosity of each sample decreased with increasing shear rate demonstrating that these hydrogels are capable of shear-thinning. FIG. 6D depicts the results of 1.5 wt % KYFIL hydrogels (n=3) that were subjected to five step strain sweeps of 100% strain (50 s), followed by a 100 s recovery period (0.1% strain). The hydrogel recovers 70-80% of its initial G' within several seconds. Even after multiple high strain cycles, the hydrogel is able to repeatedly retain its mechanical strength.

FIG. 7A shows images of amorphous peptide aggregates in nongelling conditions (pH 4.6). There is no distinct fiber formation within peptide solutions. FIG. 7B shows images of individual twisted ribbon molecular assemblies present within the hydrogel at pH 7.4. These twisted ribbons have ca. 40 nm width and ca. 132 nm pitch. FIG. 7C shows TEM images of bulk fibers within the hydrogel. Both "classical" fibrous bundles that are commonly observed in other reported self-assembling peptides and the twisted ribbon morphology are present within this hydrogel system. FIG. 7D shows cryo-EM images of 1.5 wt % KYFIL hydrogel. Twisted ribbon morphologies are present within the hydrogel.

FIG. 7E shows lower magnification of the KYFIL peptide, demonstrating that twisted ribbon morphologies are present in mass throughout the hydrogel volume. FIG. 7F is a graph depicting quantification of the pitch and diameter of the twisted ribbons is consistent and reproducible. In FIG. 7F, A and B refer to different synthetic batches.

FIG. 9A shows live/dead images of viable (green, GFP+) and membrane damaged (red, ethidium homodimer-1) cells postejection in PBS or 1.5 wt % AYFIL hydrogels. Each sample of cells encapsulated in RAPID and PBS, respectively, contained at least 140 total cells. FIG. 9B is a graph showing the percent cell viability with injection in PBS or hydrogels. Error bars represent standard error of the mean (SEM) from three separate syringe ejections (n=3), *p<0.05.

FIG. 10A demonstrates that OPCs remained viable after encapsulation for at least 4 days, as determined by the increase of ATP over time. FIG. 10B shows a graphical representation of the increase in DNA concentration, suggesting that cells proliferate over the course of 4 days. Error bars represent standard error of the mean (SEM, n=3). FIG. 10C shows live/dead (green/red staining) images taken at day 1 of the experiment, demonstrating that the majority of cells remained viable following encapsulation. The image is a maximum projection of a 132 μm thick z-stack.

FIG. 10D shows the maximum projection (23 μm thick z-stack) of OPCs encapsulated in AYFIL hydrogels after 2 days of culture. Process extension of OPCs are observed, suggesting that these hydrogel systems are suitable for neural cell culture: GFP (green), actin (red), DAPI (blue).

FIG. 13A shows a magnified view of the ATR-FTIR spectrum of peptides dissolved at 3 wt. % in PBS and pH 7.4. All gelling peptides (solid lines) exhibit an Amide I absorbance at 1629 $cm^{-1}$, indicative of β-sheet hydrogen bonding. A peak at 1679 $cm^{-1}$ to 1683 $cm^{-1}$ indicates that the β-sheet is in anti-parallel conformation. FIG. 13B shows that non-gelling peptides (dashed lines) exhibit much weaker, less intense peaks at the same wavenumbers. All spectra are baseline corrected, normalized, and offset for clarity.

FIG. 15A shows a Ramachandran plot for KYFIL; FIG. 15B shows a Ramachandran plot for AYFIL; FIG. 15C shows a Ramachandran plot for KYFAL; FIG. 15D shows a Ramachandran plot for KAFIL; and FIG. 15E shows a Ramachandran plot for KYFIV. The torsion angles for each type of amino acid, barring the N- and C-termini indicate significant structural heterogeneity within the peptide systems. The Phe for all pentapeptide analogs, adopts higher populations of β-turn type-II (ϕ=−60°, ψ=120° and antiparallel β-sheet structures (ϕ=−140°, ψ=135°. For both the KYFAL and KAFIL sequence, the Ala preferentially adopts a polyproline type-II helix (ϕ=−75°, ψ=145° and decreased propensity for β-sheet structures. Note that the residue at the N- and C-terminus does not have a Phi or Psi angle since the dihedral angle requires a plane comprised of C'—N—Cα—C' and N—Cα—C'—N for Phi and Psi angles, respectively.

FIG. 17A shows strain sweeps for KYFIL; FIG. 17B shows strain sweeps for AYFIL; FIG. 17C shows strain sweeps for KAFIL; and FIG. 17D shows strain sweeps for KYFAL. For all sequences, G' decreases significantly in acidic conditions. Higher concentrations of peptides exhibit increased G'. For KAFIL hydrogels, the G' increases significantly in basic conditions.

FIG. 18A shows frequency sweeps for KYFIL; FIG. 18B shows frequency sweeps for AYFIL; FIG. 18C shows frequency sweeps for KAFIL; and FIG. 18D shows frequency sweeps for KYFAL. For all sequences, G' decreases significantly in acidic conditions. Higher concentrations of peptides exhibit increased G'. For KAFIL hydrogels, the G' increases significantly in basic conditions.

FIG. 20A shows measurements for KYFIL; FIG. 20B shows measurements for AYFIL; FIG. 20C shows measurements for KAFIL; and FIG. 20D shows measurements for KYFAL. All hydrogels displayed shear-thinning behavior, in which the viscosity of each sample decreases with increasing shear rate.

(FIGS. 30C-D) Apparent viscosity versus shear rate measurements demonstrate that RGDKYFIL displays shear-thinning behavior.

DETAILED DESCRIPTION

Figure 2:
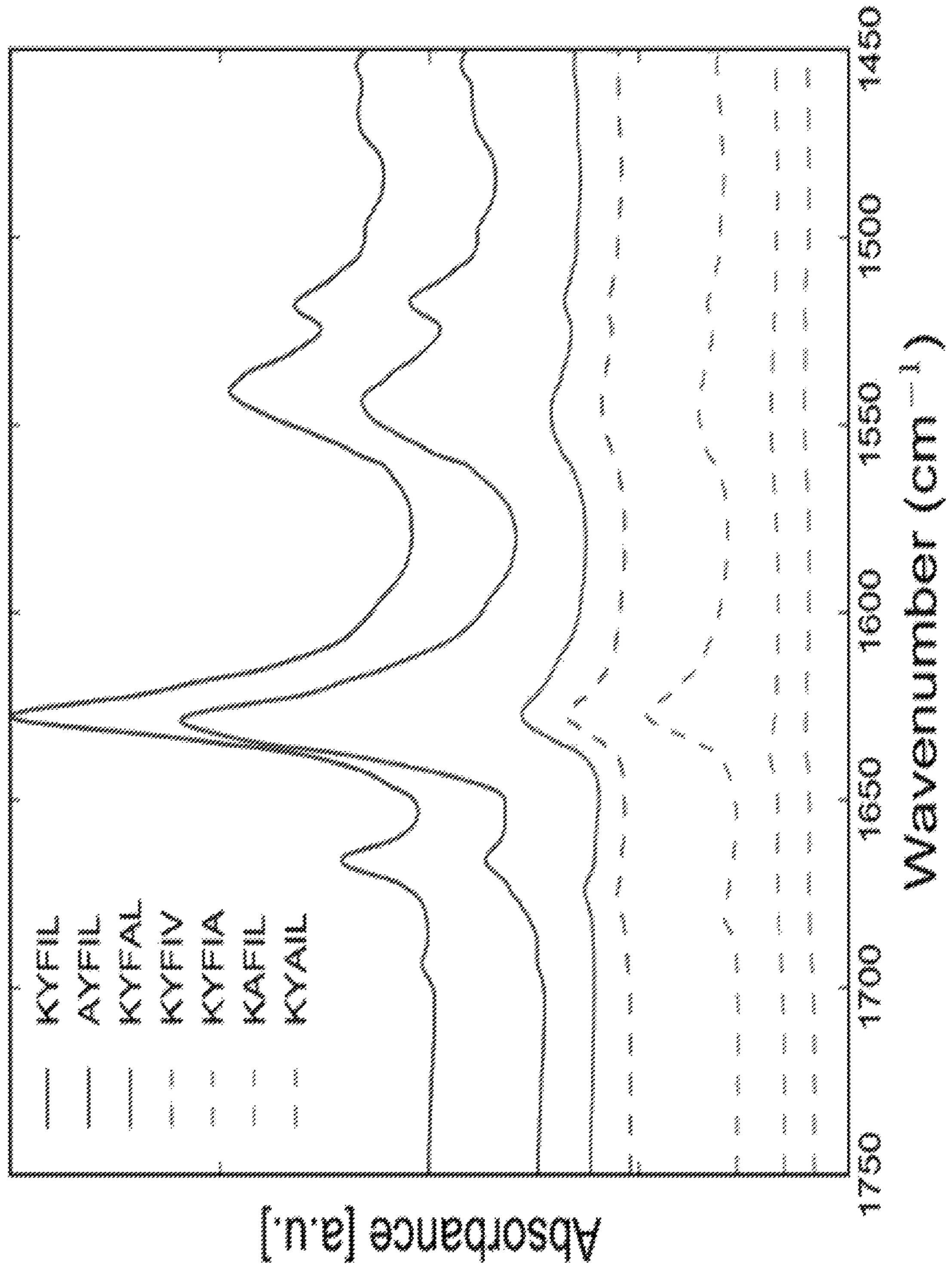
FIG. 2 is a graphical depiction showing that peptides exhibit characteristic secondary structures via ATR-FTIR. Peptides dissolved at 3 wt % in PBS and pH 7.4 were examined. All gelling peptides (solid lines) exhibit an amide I absorbance at 1629 $cm^{-1}$, indicative of β-sheet hydrogen bonding. A peak near 1679-1683 $cm^{-1}$ suggests antiparallel β-sheet conformation. Nongelling peptides (dashed lines) exhibit much weaker, less intense peaks at the same wavenumbers. All spectra are baseline corrected, normalized, and vertically offset for clarity.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes and compositions are described as using specific a specific order of individual steps or specific materials, it is appreciated that steps or materials may be interchangeable such that the description of the invention may include multiple steps or parts arranged in many ways as is readily appreciated by one of skill in the art.

The terminology used herein is for describing particular embodiments/aspects only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It is to be further understood that where descriptions of various embodiments use the term "comprising,", "including", and/or "having" those skilled in the art would understand that in instances, an embodiment can be alternatively described using language "consisting essentially of" or "consisting of." The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The presently-disclosed data relates to a new class of short, pentapeptides and peptides containing such self-assembling pentapeptides that form hydrogels with nanofiber structures. Using rheology and spectroscopy, the data demonstrates how sequence variations, pH, and peptide concentration may be used to alter the mechanical properties of the instantly-disclosed hydrogels. The data demonstrates that the instantly-disclosed unmodified peptides form robust hydrogels (e.g., in aspects from about 0.2 to about 20 kPa) at low weight percent (e.g., in aspects, equal to or less than 3 wt %) in physiological conditions (e.g., in aspects, in a physiological buffer under biologically acceptable conditions (pH=7.4)) and undergo shear-thinning and rapid self-healing. The peptides self-assemble into long fibrils with sequence-dependent fibrillary morphologies. These fibrils exhibit a unique twisted ribbon shape, as visualized by transmission electron microscopy (TEM) and Cryo-EM imaging, with diameters in the low tens of nanometers and periodicities similar to amyloid fibrils. Experimental gelation behavior corroborates the molecular dynamics simulations, which demonstrate peptide assembly behavior, an increase in β-sheet content, and patterns of variation in solvent accessibility. These hydrogels, which may be referred to herein as rapidly assembling pentapeptides for injectable delivery (RAPID) hydrogels are syringe-injectable and support cytocompatible encapsulation of cells, including oligodendrocyte progenitor cells (OPCs), as well as their proliferation and three-dimensional process extension. Furthermore, the data demonstrates that the instantly-disclosed RAPID hydrogels protect cells from mechanical membrane disruption and acute loss of viability when ejected from a syringe needle, highlighting the protective capability of these hydrogels as potential cell carriers for transplantation therapies. Importantly, the tunable mechanical and structural properties of these supramolecular assemblies are shown to be permissive to cell expansion and remodeling, making the instantly-disclosed hydrogel systems suitable as injectable material for cell delivery and tissue engineering applications. Therefore, as these RAPID hydrogels formed from instantly-disclosed self-assembling pentapeptides are stable under biologically acceptable, tissue culture conditions, are of similar dimensions to fibrous components of the extracellular matrix (i.e., nano-sized fibers), and are capable of supporting cell culture in both 2-D and in 3-D, these hydrogels find use in a wide range of medical applications.

Pentapeptides and Nucleic Acids

In aspects, the present disclosure provides a novel class of self-assembling pentapeptides and peptides containing such self-assembling pentapeptides capable of forming robust nanofiber hydrogels upon mixing under physiological conditions as described herein, as well as nucleic acids (e.g., DNA or RNA) encoding one or more peptides of the present disclosure.

In aspects, the present disclosure is directed to a peptide having an amino acid sequence $(X_1\text{-}X_2\text{-F-}X_3\text{-L})_a$, or variants and fragments thereof, wherein $X_1$ is a positively charged or an aliphatic amino acid, $X_2$ is an aliphatic or an aromatic amino acid, $X_3$ is a hydrophobic amino acid, and a is 1 or 2. In aspects, the present disclosure is directed to a peptide comprising an amino acid sequence having at least 60%, 70%, 80%, or 90% homology to a peptide having an amino acid sequence $(X_1\text{-}X_2\text{-F-}X_3\text{-L})_a$, or variants and fragments thereof, wherein $X_1$ is a positively charged or an aliphatic amino acid, $X_2$ is an aliphatic or an aromatic amino acid, $X_3$ is a hydrophobic amino acid, and a is 1 or 2, said peptide capable of self-assembling and forming robust nanofiber hydrogels upon mixing under physiological conditions as described herein. In aspects, the present disclosure is directed to a 6-mer, 7-mer, 8-mer, 9-mer, or 10-mer peptide having an amino acid sequence comprising $(X_1\text{-}X_2\text{-F-}X_3\text{-L})_a$, or variants and fragments thereof, wherein $X_1$ is a positively charged or an aliphatic amino acid, $X_2$ is an aliphatic or an aromatic amino acid, $X_3$ is a hydrophobic amino acid, and a is 1 or 2. In aspects of the above-referenced peptides, $X_1$ is an amino acid residue selected from the group consisting of K, A, and V, $X_2$ is an amino acid residue selected from the group consisting of Y and A, and $X_3$ is an amino acid residue selected from I and A. In aspects of the above-referenced peptides, $X_1$ is an amino acid residue selected from the group consisting of K and A, $X_2$ is an amino acid residue selected from the group consisting of Y and A, and $X_3$ is an amino acid residue selected from I and A. In aspects of the above-referenced peptides, the peptide has an uncharged C-terminus. In aspects of the above-referenced peptides, the peptide is C-terminally amidated. In aspects of the above-referenced peptides, the peptide is capable of self-assembling and forming robust nanofiber hydrogels (e.g., in aspects, upon mixing under physiological conditions as described herein). In aspects, the present disclosure is directed to a nucleic acid sequence (e.g., DNA or RNA) encoding one or more peptides of the present disclosure.

As used herein, a "positively charged amino acid" includes lysine (K), arginine (R), and histidine (H). As used herein, an "aliphatic amino acid" includes alanine (A), isoleucine (I), proline (P), and valine (V). As used herein, an "aromatic amino acid" includes phenylalanine (F), tryptophan (W), tyrosine (Y), and histidine (H). As used herein, a "hydrophobic amino acid" includes glycine (G), alanine (A), valine (V), leucine (L), isoleucine (I), proline (P), phenylalanine (F), methionine (M), and tryptophan (W).

In aspects, the present disclosure is directed to a peptide having an amino acid sequence set forth in SEQ ID NO: 1 (KYFIL), SEQ ID NO: 2 (AYFIL), SEQ ID NO: 3 (KYFAL), SEQ ID NO: 4 (KAFIL), SEQ ID NO: 5 (KYAIL), SEQ ID NO: 6 (KYFIA), SEQ ID NO: 7 (KYFIV), SEQ ID NO: 8 (VYFIL), SEQ ID NO: 9 (RYFIL), SEQ ID NO: 10 (KYFILKYFIL), SEQ ID NO: 11 (AYFILAYFIL), SEQ ID NO: 12 (KYFALKYFAL), SEQ ID NO: 13 (KAFILKAFIL), SEQ ID NO: 14 (KYAILKYAIL), SEQ ID NO: 15 (KYFIAKYFAI), SEQ ID NO: 16 (KYFIVKYFIV), SEQ ID NO: 17 (VYFILVYFIL) or SEQ ID NO: 18 (RYFILRYFIL), and fragments and variants thereof. In aspects, the present disclosure is directed to a peptide comprising an amino acid sequence having at least 60%, 70%, 80% or 90% homology to a peptide having an amino acid sequence set forth in SEQ ID NO: 1 (KYFIL), SEQ ID NO: 2 (AYFIL), SEQ ID NO: 3 (KYFAL), SEQ ID NO: 4 (KAFIL), SEQ ID NO: 5 (KYAIL), SEQ ID NO: 6 (KYFIA), SEQ ID NO: 7 (KYFIV), SEQ ID NO: 8 (VYFIL), SEQ ID NO: 9 (RYFIL), SEQ ID NO: 10 (KYFILKYFIL), SEQ ID NO: 11 (AYFILAYFIL), SEQ ID NO: 12 (KYFALKYFAL), SEQ ID NO: 13 (KAFILKAFIL), SEQ ID NO: 14 (KYAILKYAIL), SEQ ID NO: 15 (KYFIAKYFAI), SEQ ID NO: 16 (KYFIVKYFIV), SEQ ID NO: 17 (VYFILVYFIL) or SEQ ID NO: 18 (RYFILRYFIL), and fragments and variants thereof, said peptide capable of self-assembling and forming robust nanofiber hydrogels (e.g., in aspects, upon mixing under physiological conditions as described herein). In aspects of the above-referenced peptides, the peptide has an uncharged C-terminus. In aspects of the above-referenced peptides, the peptide is C-terminally amidated. In aspects of the above-referenced peptides, the peptides may be isolated, synthetic, or recombinant. In aspects of the above-referenced peptides, the peptide is capable of self-assembling and forming robust nanofiber hydrogels (e.g., in aspects, upon mixing under physiological conditions as described herein). In aspects, the present disclosure is directed to a nucleic acid sequence (e.g., DNA or RNA) encoding one or more peptides of the present disclosure. In aspects of the instantly-disclosed polynucleotides, the nucleic acid sequences may be isolated, synthetic, or recombinant.

The terms "peptide" is herein to refer to a polymer of amino acid residues. The term may apply to amino acid polymers in which one or more amino acid residues is an artificial chemical analogue of a corresponding naturally occurring amino acid, as well as to naturally occurring amino acid polymers.

The term "nucleic acid sequence" is used interchangeably to refer to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides. The term "nucleic acid sequence" is not intended to limit the present invention to nucleic acid sequence s comprising DNA. Those of ordinary skill in the art will recognize that nucleic acid sequences can comprise ribonucleotides and combinations of ribonucleotides and deoxyribonucleotides. Such deoxyribonucleotides and ribonucleotides include both naturally occurring molecules and synthetic analogues. The nucleic acid sequences of the invention also encompass all forms of sequences including, but not limited to, single-stranded forms, double-stranded forms, and the like. As used herein, the terms "encoding" or "encoded" when used in the context of a specified nucleic acid sequences mean that the nucleic acid sequence comprises the requisite information to direct translation of the nucleic acid sequence into a specified polypeptide. The information by which a polypeptide is encoded is specified by the use of codons. A nucleic acid sequence encoding a peptide may comprise non-translated sequences (e.g., introns) within translated regions of the nucleic acid or may lack such intervening non-translated sequences (e.g., as in cDNA).

As used herein, a peptide or nucleic acid sequence is said to be "isolated" or "purified" when it is substantially free of cellular material when it is isolated from recombinant and non-recombinant cells, or free of chemical precursors or other chemicals when it is chemically synthesized. As such, an isolated or purified peptide or nucleic acid sequence is substantially free of other cellular material, or culture medium when produced by recombinant techniques, or substantially free of chemical precursors or other chemicals when chemically synthesized. Optimally, an "isolated" n is free of sequences (optimally protein encoding sequences) that naturally flank the nucleic acid sequence (i.e., sequences located at the 5' and 3' ends of the nucleic acid sequence) in the genomic DNA of the organism from which the nucleic acid sequence is derived. For example, in various embodiments, the isolated nucleic acid sequence can contain less than about 5 kb, 4 kb, 3 kb, 2 kb, 1 kb, 0.5 kb, or 0.1 kb of nucleotide sequence that naturally flank the nucleic acid sequence in genomic DNA of the cell from which the nucleic acid sequence is derived. A peptide or nucleic acid sequence that is substantially free of cellular material includes preparations of peptides having less than about 30%, 20%, 10%, 5%, 1%, or any value or range therebetween (by dry weight) of other proteins (e.g., contaminating proteins). When the peptides of the invention are recombinantly produced, optimally culture medium represents less than about 30%, 20%, 10%, 5%, 1%, or any value or range therebetween (by dry weight) of chemical precursors or non-protein-of-interest chemicals that are involved in the peptide or nucleic acid sequence synthesis.

As used herein, two polypeptides (or a region of the proteins) are substantially homologous when the amino acid sequences have a certain percentage or more identity, e.g., at least about 60%, 80%, 85%, 90%, 91%, 92%, 93%, 94%, 95%, 96%, 97%, 98%, or 99% identity. Percent homology can be determined as is known in the art. For example, to determine the percent identity of two amino acid sequences, the sequences are aligned for optimal comparison purposes (e.g., gaps can be introduced in one or both of a first and a second amino acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). As is known in the art, the percent identity between the two sequences is a function of the number of identical positions shared by the sequences, taking into account the number of gaps, and the length of each gap, which need to be introduced for optimal alignment of the two sequences. Sequence homology for polypeptides is typically measured using sequence analysis software.

When homologous is used in reference to polypeptides, it is recognized that residue positions that are not identical can often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are known to those of skill in the art. The following six groups each contain amino acids that are conservative substitutions for one another: 1) Serine(S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

In embodiments, amino acid residues which are not believed to be essential for the functioning of the instantly-disclosed polypeptides may be substituted either conservatively or non-conservatively, and such amino acid substitutions would likely not significantly diminish the functional properties of the polypeptides.

Fragments and variants of the disclosed polypeptides and polynucleotides are also encompassed by the present invention. "Fragment" is intended to mean a portion of the polypeptide or polynucleotide. Fragments of a polypeptide or a nucleotide sequence as disclosed herein may encode polypeptide fragments that retain the biological activity of the polypeptides of the instant disclosure, and hence have antipathogenic activity, antifungal activity, antialgal activity, and/or enzymatic activity against chitin and/or polyglucuronic acid. In aspects, the present disclosure also encompasses fragments of the variants of the polypeptides and polynucleotides described herein.

"Variants" is intended to mean substantially similar sequences. A "variant" polypeptide is intended to mean a polypeptide derived from the instantly-disclosed polypeptides of the current invention by deletion or addition of one or more amino acids at one or more internal sites in the native protein and/or substitution of one or more amino acids at one or more sites in the native protein. Variant polypeptides encompassed by the present invention are biologically active, that is they continue to possess the desired biological activity the polypeptides of the instant-disclosure, that is, self-assembling pentapeptides capable of forming robust nanofiber hydrogels upon mixing under physiological conditions as described herein. Such variants may result from, for example, genetic polymorphism or from human manipulation. Biologically active variants will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the peptides of the invention as determined by sequence alignment programs and parameters described elsewhere herein.

A biologically active variant of a peptide of the instant disclosure may differ from that peptide by as few as even 1 amino acid residue. It is recognized that residue positions that are not identical can often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are known to those of skill in the art. The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

The peptides of the instant disclosure may be altered in various ways including amino acid substitutions, deletions, truncations, and insertions. Methods for such manipulations are generally known in the art. For example, amino acid sequence variants and fragments of the instantly-disclosed peptides can be prepared by mutations in the DNA. Methods for mutagenesis and nucleic acid sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the peptides of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found (Bowie J U et al., (1990), Science, 247 (4948): 130610, which is herein incorporated by reference in its entirety). For the purposes of the present disclosure, the instantly-disclosed peptides can include, for example, modified forms of naturally occurring amino acids such as D-stereoisomers, non-naturally occurring amino acids; amino acid analogs; and mimetics.

Peptides of the instant disclosure can be produced either from a nucleic acid sequence disclosed herein, or by the use of standard molecular biology techniques, such as recombinant techniques, mutagenesis, synthetic peptide production techniques, or other known means in the art. An isolated peptide can be purified from cells that naturally express it, purified from cells that have been altered to express it (recombinant), or synthesized using known protein synthesis techniques. In aspects, peptides of the instant disclosure are produced by recombinant DNA or RNA techniques. In aspects, a peptide of the invention can be produced by expression of a recombinant nucleic acid of the invention in an appropriate host cell. For example, a nucleic acid molecule encoding the peptide is cloned into an expression cassette or expression vector, the expression cassette or expression vector introduced into a host cell and the polypeptide expressed in the host cell. The peptide can then be isolated from the cells by an appropriate purification scheme using standard protein purification techniques. Alternatively a peptide can be produced by a combination of ex vivo procedures, such as protease digestion and purification. Further, peptides of the invention can be produced using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety).

For nucleic acid sequences, a "variant" comprises a deletion and/or addition of one or more nucleotides at one or more internal sites within the nucleic acid sequences of the instant disclosure and/or a substitution of one or more nucleotides at one or more sites in the nucleic acid sequences of the instant disclosure. One of skill in the art will recognize that variants of the nucleic acid sequences of the invention will be constructed such that the open reading frame is maintained. For nucleic acid sequences, conservative variants include those sequences that, because of the degeneracy of the genetic code, encode the amino acid sequence of one of the peptides of the invention. Naturally occurring allelic variants such as these can be identified with the use of well-known molecular biology techniques, as, for example, with polymerase chain reaction (PCR) and hybridization techniques as outlined below. Variant nucleic acid sequences also include synthetically derived nucleic acid sequences, such as those generated, for example, by using site-directed mutagenesis but which still encode a nucleic acid sequence having the desired activity of the invention (i.e., encoding a peptide that possesses the desired biological activity, that is, self-assembling pentapeptides capable of forming robust nanofiber hydrogels upon mixing under physiological conditions as described herein). Generally, variants of a particular nucleic acid sequence of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleic acid sequence as determined by sequence alignment programs and parameters described elsewhere herein.

Variants of a particular nucleic acid sequence of the invention (i.e., the reference nucleic acid sequence) can also be evaluated by comparison of the percent sequence identity between the peptide encoded by a variant nucleic acid sequence and the peptide encoded by the reference nucleic acid sequence. Thus, for example, an isolated nucleic acid sequence that encodes a peptide with a given percent sequence identity to the polypeptides of the instant disclosure are disclosed. Percent sequence identity between any two peptides can be calculated using sequence alignment programs and parameters described elsewhere herein. Where any given pair of nucleic acid sequences of the invention is evaluated by comparison of the percent sequence identity shared by the two peptides they encode, the percent sequence identity between the two encoded peptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The nucleic acid sequences provided herein (whether RNA, DNA, expression cassettes, vectors, viruses or hybrids thereof) that encode in whole or in part one or more peptides of the present disclosure can be isolated from a variety of sources, genetically engineered, amplified, synthetically produced, and/or expressed/generated recombinantly. Recombinant peptides generated from these nucleic acids can be individually isolated or cloned and tested for a desired activity. Any recombinant expression system can be used, including e.g. in vitro, bacterial, fungal, mammalian, yeast, insect or plant cell expression systems. In aspects nucleic acid sequences provided herein are synthesized in vitro by well-known chemical synthesis techniques (as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066, all of which are herein incorporated by reference in their entirety). Further, techniques for the manipulation of nucleic acid sequences provided herein, such as, e.g., subcloning, labeling probes (e.g., random-primer labeling using Klenow polymerase, nick translation, amplification), sequencing, hybridization and the like are well described in the scientific and patent literature (see, e.g., Sambrook, ed., Molecular Cloning: A Laboratory Manual (2ND ED.), Vols. 1-3, Cold Spring Harbor Laboratory, (1989); Current Protocols In Molecular Biology, Ausubel, ed. John Wiley & Sons, Inc., New York (1997); Laboratory Techniques In Biochemistry And Molecular Biology: Hybridization With Nucleic Acid Probes, Part I. Theory and Nucleic Acid Preparation, Tijssen, ed. Elsevier, N.Y. (1993), all of which are herein incorporated by reference in their entirety).

Hydrogel Compositions and Formulations

In aspects, the hydrogels of the present disclosure comprise one or more the instantly-disclosed pentapeptides which make up the 3-dimensional nanofibrous network of the hydrogel structure. The instantly disclosed hydrogels are shear-thinning hydrogels that have high storage moduli and high rates of recovery after destruction. These hydrogels are useful in various applications, including but not limited to, scaffolds for tissue engineering, 2-dimensional (2-D) and 3-dimensional (3-D) cell cultures, drug delivery and encapsulation of therapeutic agents (cells, molecules, drugs, compounds), injectables (including those that gel in situ, such as hemostatic compositions), hemostatic agents, wound dressings, pharmaceutical carriers or vehicles, cell transplantation, cell storage, virus culture, and virus storage.

In aspects, a hydrogel composition of the present disclosure comprises an aqueous dispersion phase comprising an aqueous dispersion medium and at least one peptide of the present disclosure as previously described. In aspects, the hydrogel is formed by self-assembly of said at least one peptide in said aqueous dispersion phase. In aspects, the hydrogel may comprise a plurality of identical peptides (e.g., a single peptide as disclosed herein), or a plurality of peptides that are different (e.g., one or more of the peptides as disclosed herein). One of skill in the art will understand that by choosing which of the instantly-disclosed peptides, or combination of peptides, used to form the instantly-disclosed hydrogels, it is possible to tailor the structural and functional characteristics of the resultant hydrogel formed under biologically acceptable conditions.

In aspects of the instantly-disclosed hydrogel, the aqueous dispersion medium is physiologically acceptable. In further aspects, the aqueous dispersion medium comprises one or more salts. In even further aspects, the aqueous dispersion medium comprises one or more salts selected from the group consisting of $(NH_4)_2SO_4$, $Na_2SO_4$, NaCl, KCl and $CH_3COONH_4$. In aspects, an aqueous dispersion medium may comprise phosphate buffered saline, DMEM and other appropriate aqueous medium as known to one skilled in the art. For example, OPC media (e.g., DMEM with high glucose, 4 mM L-glutamine, 1 mM sodium pyruvate (Life Technologies) with N2 and B27 supplement (Life Technologies), C2C12 media (e.g., DMEM with 10% Fetal Bovine Serum, and 1% penicillin-streptomycin), hMSC media (e.g., DMEM with 20% Fetal Bovine Serum, and 1% penicillin-streptomycin), MLF media (e.g., DMEM with high glucose, 4 mM L-glutamine, 1 mM sodium pyruvate (Life Technologies) and supplemented with 1% penicillin-streptomycin (Life Technologies) and 20% Fetal Bovine Serum), and iPSC-derived NSC media (DMEM/F12+Glutamax with N2, B27 without vitamin A, 1 ug/mL), or the like are all appropriate.

As used herein, a "hydrogel" refers to a gel in which water is the major dispersion medium. Preferably, the water disperses the components of the hydrogel, e.g., the peptides as disclosed herein. Preferably, the hydrogel comprises at least 80% (w/w) water, more preferably, at least 85% (w/w) water, and more preferably, at least 90% (w/w), even more preferably, at least 95% (w/w) water.

As used herein, the term "physiologically acceptable" in relation to the aqueous dispersion medium, refers to any suitable solution that is capable of conferring biologically acceptable conditions on the instantly-disclosed peptides such that are capable of self-assemble (i.e. with each other) resulting in gelation to form the hydrogel. Examples of suitable solutions will be known to the skilled technician, and may comprise a physiological buffer, such as saline or other buffered aqueous solutions.

As used herein, the term "biologically acceptable" means that the hydrogels of the instant disclosure is substantially stable under in vivo conditions, e.g., pH, temperature, and/or ionic strength as found in vivo. In aspects, the aqueous dispersion medium has a pH of a pH from about 6 to about 11, from about 7 to about 11, from about 7 to about 10, from about 9 to about 11, from about 10 to about 11, from about 6 to about 8, from about 7 to about 8, from about 7.3 to about 7.5, about 7.4, or about 10.6, including any values or ranges therebetween. In aspects, the hydrogel itself has a pH from about 6 to about 11, from about 7 to about 11, from about 7 to about 10, from about 9 to about 11, from about 10 to about 11, from about 10.4 to about 10.7, from about 6 to about 8, from about 7 to about 8, from about 7.3 to about 7.5, about 7.4, or about 10.6, including any values or ranges therebetween.

In aspects of a hydrogel of the present disclosure, the at least one peptide is present in said hydrogel at a level of from about 0.1% by weight to about 5% by weight, including every value and range therebetween based upon the total weight of the hydrogel. In aspects of a hydrogel of the present disclosure, the at least one peptide is present in said hydrogel at a level of from about 1.0% by weight to about 3.5% by weight, including every value and range therebetween based upon the total weight of the hydrogel. In aspects of a hydrogel of the present disclosure, the at least one peptide is present in said hydrogel at a level of from about 1.5% by weight to about 3.0% by weight, including every value and range therebetween based upon the total weight of the hydrogel.

In aspects of the hydrogels of the present disclosure, the hydrogel comprises peptide nanofibers of the instantly-disclosed peptides. As previously described, the instantly-disclosed pentapeptides make up the 3-dimensional nanofibrous network of the hydrogel structure. In aspects, the peptide nanofibers of the instantly-disclosed hydrogels may have an average diameter of from about 10 nm to about 40 nm, including every value and range therebetween. In aspects, the peptide nanofibers have a fiber length of up to about 100 μm. In aspects, the peptide nanofibers bundle into hierarchical nanostructures, including twisted fibrils and/or twisted, ribbon-like morphologies. In aspects, the peptide nanofibers form multistranded twisted ribbons.

In aspects of a hydrogel of the present disclosure, the hydrogels are characterized by having a "reversible" hydrogel matrix, which means that the 3-dimensional nanofibrous matrix is shear thinning (i.e., the viscosity decreases with an increase in the rate of shear stress applied to the gel), but recovers quickly after gel destruction. As such, in aspects the hydrogel is a shear-thinning hydrogel. In aspects of the instantly-disclosed hydrogels, after gel destruction by subjecting the gel to a sufficient mechanical force (e.g., shear thinning, by, e.g., injection through a needle), the hydrogels have a % recovery of at least about 60%, preferably at least about 80%, more preferably at least about 90%, and even more preferably about 100% in less than about 10, 9, 8, 7, 6, 5, 4, 3, 2, or 1 minutes (after removing the shear stress from the destroyed gel). In aspects, after 100% strain, the hydrogels recover gel behavior (G'>G") in less than about 1 minute, 30 seconds, or 15 seconds. As used herein, the "% recovery" of the hydrogel is the percentage of the original storage modulus (i.e., before gel destruction) achieved by the gel after destruction and re-hydrogelation. Thus, shear-thinning only temporarily destroys the gel structure or architecture. As is understood by a person of skill in the art, shear-thinning may be carried out using various mechanical forces that impose a shear strain or shear stress on the hydrogel, such as pipetting, centrifugation, vibration, injection, spraying, filtration, and the like. As noted above, reassembly of the gel or hydrogelation reoccurs quickly after shear thinning and destruction of the gel structure (i.e., after removal of or stopping the application of mechanical force to the destroyed gel). In aspects, this recovery property also persists even after destroying the gel structure multiple times. In aspects, the destroyed matrix after shear thinning can also be diluted with solvent to a substantially liquid solution (i.e., G'<0.2 Pa) to stop the recovery process.

In aspects of a hydrogel of the present disclosure, the hydrogels have a shear storage moduli (G') of at least about 50 Pa. In aspects of a hydrogel of the present disclosure, the hydrogels have a shear storage moduli (G') from about 50 Pa to about 20,000 Pa, including every value and range therebetween. In aspects of a hydrogel of the present disclosure, the hydrogels have a shear storage moduli (G') from about 50 Pa to about 17,000 Pa, including every value and range therebetween. In aspects, the shear storage moduli of the instantly-disclosed hydrogels may be tuned to a desired application of the hydrogel by adjusting the peptide concentrations. By way of example, for an injectable hydrogel, the hydrogel matrix may have a storage moduli of from about 50 Pa to about 3,000 Pa and preferably from about 70 Pa to about 1,000 Pa. In aspects in which a very strong hydrogel is desired, such as for scaffolding, a hydrogel of the instant disclosure may have a storage moduli of at least about 500 Pa, preferably from about 100 Pa to about 10,000 Pa, and even more preferably from about 3,000 Pa to about 20,000 Pa. In aspects, these gel strengths are based upon a neutral pH (about 7-about 7.4) and a temperature of about room temperature (aka "ambient temperature" or about 20-25° C.).

In aspects, the hydrogels of the instant disclosure are water-soluble. As used herein, "water-soluble" means the gels can be diluted with water or an aqueous polar solution (e.g., PBS, DMEM media, or the like) after formation. In aspects, the hydrogel becomes "softer", e.g., demonstrate lower storage and loss modulus after dilution. In aspects, the hydrogels of the instant disclosure are temperature stable up to about 60° C., 70° C., 80° C. or 90° C., with "temperature stable" meaning that the hydrogel is not denatured at temperatures ranging from about 1° C. to about 60° C., 70° C., 80° C. or 90° C.

In aspects of the above-referenced hydrogel compositions, the hydrogel further comprises an active agent, including therapeutics, such as small molecule drugs and/or biologics (e.g., enzymes and other proteins and peptide, and DNA and RNA fragments). In aspects of the above-referenced hydrogel compositions, the hydrogel further comprises a cell.

In other aspects, the present disclosure is directed to a liquid hydrogel precursor composition comprising: an aqueous dispersion phase comprising an aqueous dispersion medium; and at least one peptide as disclosed herein, wherein said composition is capable of being induced to form a hydrogel by self-assembly of said at least one peptide in said aqueous dispersion phase.

In additional aspects, the present disclosure is directed to a pharmaceutical composition comprising a hydrogel as disclosed herein and a pharmaceutically acceptable vehicle. As used herein, a "pharmaceutically acceptable vehicle" as referred to herein is any physiological vehicle known to those of ordinary skill in the art useful in formulating pharmaceutical compositions. The pharmaceutically acceptable vehicle may be a liquid, and the pharmaceutical composition is in the form of a solution. In a further preferred embodiment, the pharmaceutical vehicle is a gel or hydrogel, and the composition is in the form of a cream or the like. In both cases, the composition may be applied to the treatment site. In aspects, the pharmaceutical composition comprises an effective amount of the hydrogel. As used herein, A "therapeutically effective amount" is any amount which, when administered to a subject provides prevention and/or treatment of a specific medical condition.

In aspects, the present disclosure is directed to a cell-supporting medium comprising a hydrogel composition as disclosed herein and at least one cell. The cell may be of any cell type and is not particularly limited, and may include, e.g., epithelial cells, neurons, endothelial cells, osteoblasts, chondrocytes, fibroblasts, smooth muscle cells, osteoclasts, keratinocytes, nerve progenitor cells, stem cells, macrophages and other immune cells, and/or islet cells.

In aspects of the instantly disclosed hydrogel compositions, liquid hydrogel precursor compositions, pharmaceutical compositions, or cell-supporting medium, the compositions may comprise one or more substances, which may also act as lubricants, solubilizers, suspending agents, fillers, glidants, compression aids, or binders. It can also be an encapsulating material. Liquid vehicles are used in preparing solutions, suspensions, emulsions, syrups, elixirs and pressurized compositions. The hydrogel compositions, liquid hydrogel precursor compositions, or pharmaceutical compositions may be dissolved or suspended in a pharmaceutically acceptable liquid vehicle such as water, an organic solvent, a mixture of both or pharmaceutically acceptable oils or fats. The liquid vehicle may contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral and parenteral administration and implants include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

Methods of Forming Hydrogels

In aspects, the present disclosure is directed to a method of preparing the instantly-disclosed hydrogel compositions, the method comprising the steps of: (i) preparing an aqueous solution of said at least one peptide of the instant disclosure and as described above; and (ii) adjusting the pH of said aqueous solution such that hydrogel formation occurs. In aspects, hydrogel formation occurs one G' (storage modulus) is greater than G" (storage loss). In aspects, the pH is adjusted to about 7-11. In aspects, the pH is adjusted to a pH from about 6 to about 11, from about 7 to about 11, from about 7 to about 10, from about 9 to about 11, from about 10 to about 11, from about 6 to about 8, from about 7 to about 8, from about 7.3 to about 7.5, about 7.4, or about 10.6, including any values or ranges therebetween. In aspects, the pH may be adjusted by adding an acid, e.g., an acid selected from the group consisting of HCl, formic acid (HCOOH), acetic acid ($CH_3COOH$), HBr, and nitric acid ($HNO_3$) until such pH is achieved. Further, as the hydrogels of the instant disclosure are substantially stable under in vivo conditions, e.g., pH, temperature, and/or ionic strength as found in vivo, the hydrogel may be formed at a treatment site of an individual (e.g., a mammal, such as, but not limited to a human). For example, a liquid hydrogel precursor composition may be delivered to a treatment site of an individual, where due to the pH of the treatment site (e.g., pH≈7.4), the liquid hydrogel precursor composition will form a hydrogel.

In aspects, the least one peptide is present in said solution at a level of from about 0.1% by weight to about 5% by weight, including every value and range therebetween, based upon the total weight of the solution. In aspects, least one peptide is present in said solution at a level of from about 1.0% by weight to about 3.5% by weight, including every value and range therebetween, based upon the total weight of the solution. In aspects, least one peptide is present in said solution at a level of from about 1.5% by weight to about 3.0% by weight, including every value and range therebetween, based upon the total weight of the solution.

Methods of Use

As previously described, the instantly-disclosed hydrogels and related compositions as described herein are useful in various applications, including but not limited to, scaffolds for tissue engineering, 2-dimensional (2-D) and 3-dimensional (3-D) cell cultures, drug delivery and encapsulation of therapeutic agents (cells, molecules, drugs, compounds), injectables (including those that gel in situ, such as hemostatic compositions), hemostatic agents, wound dressings, pharmaceutical carriers or vehicles, cell transplantation, cell storage, in vitro toxicity testing, virus culture, and virus storage.

In aspects, the present disclosure is directed to a method of treating an individual suffering from a medical condition characterized by tissue loss/damage, the method comprising forming a hydrogel as disclosed herein, wherein said forming is conducted (a) at a treatment site of an individual in need of such treatment, or (b) in vitro followed by transferring said hydrogel to said treatment site. Medical conditions characterized by tissue loss/damage include, but are not limited to, the treatment of wounds and tissue degenerative disorders (including neurodegenerative disorders, intervertebral disorders, muscle atrophy, kidney disorders, or cartilage or bone disorders.

In aspects of a method of treating an individual suffering from a medical condition characterized by tissue loss/damage, the hydrogel or related composition as disclosed herein includes a cell. The cell may be of any cell type and is not particularly limited, and may include, e.g., epithelial cells, neurons, endothelial cells, osteoblasts, chondrocytes, fibroblasts, smooth muscle cells, osteoclasts, keratinocytes, nerve progenitor cells, stem cells, macrophages and other immune cells, and/or islet cells. As is understood by a person of skill in the art, the type of cell(s) included will depend on the type of tissue being repaired/regenerated.

In aspects of a method of treating an individual suffering from a medical condition characterized by tissue loss/damage, forming a hydrogel comprises adjusting the pH of said aqueous solution such that hydrogel formation occurs. In aspects, hydrogel formation occurs one G' (storage modulus) is greater than G" (storage loss). In aspects, the pH is adjusted to about 7-11. In aspects, the pH is adjusted to a pH from about 6 to about 11, from about 7 to about 11, from about 7 to about 10, from about 9 to about 11, from about 10 to about 11, from about 6 to about 8, from about 7 to about 8, from about 7.3 to about 7.5, about 7.4, or about 10.6, including any values or ranges therebetween. In aspects, the pH may be adjusted by adding an acid, e.g., an acid selected from the group consisting of HCl, formic acid (HCOOH), acetic acid ($CH_3COOH$), HBr, and nitric acid ($HNO_3$) until such pH is achieved. Further, as the hydrogels of the instant disclosure are substantially stable under in vivo conditions, e.g., pH, temperature, and/or ionic strength as found in vivo, the hydrogel may be formed at a treatment site of an individual (e.g., a mammal, such as, but not limited to a human). For example, a liquid hydrogel precursor composition may be delivered to a treatment site of an individual, where due to the pH of the treatment site (e.g., pH≈7.4 or lower pH in the case of a tumorogenic and/or ischemic environments, e.g., about 6 to about 7.4), the liquid hydrogel precursor composition will form a hydrogel.

In additional aspects, the present disclosure is directed to a method of delivering an active agent to an individual, said method comprising administering a hydrogel of the instant disclosure to said individual, wherein the active agent is encapsulated in the hydrogel. As previously described, an active agent includes therapeutics, such as small molecule drugs and/or biologics (e.g., enzymes and other proteins and peptide, and DNA and RNA fragments).

In aspects of the above-methods, the hydrogel and related compositions of the present disclosure may be administered by injection into the individual, e.g., by injection into the wound areas. In aspects, injections may be intravenous (bolus or infusion) or subcutaneous (bolus or infusion). Further, in aspects, the instantly-disclosed hydrogel and related compositions of the present disclosure may also be incorporated within a slow or delayed release device. In aspects, such devices may, for example, be positioned on or adjacent the area to be treated, for example by implantation, and the hydrogel and related compositions of the present disclosure (and/or active agent associated therewith) may be released over weeks or even months. As is understood by a person of skill in the art, such devices may be particularly advantageous when long-term treatment with the medicament is required and which would normally require frequent administration (e.g. at least daily injection or implant).

In aspects, the amount of the instantly-disclosed hydrogel or related compositions (and/or active agent associated therewith) required will be determined by its biological activity and bioavailability, which in turn depends on the mode of administration, the physicochemical properties of the medicament employed, and whether the hydrogel, compositions, cell-supporting medium, or medicament is being used as a monotherapy or in a combined therapy. The frequency of administration will also be influenced by the above-mentioned factors and particularly the half-life of the medicament within the subject being treated. Optimal dosages of the instantly-disclosed hydrogel or related compositions (and/or active agent associated therewith) to be administered may be determined by those skilled in the art, and will vary with the particular hydrogel, related composition, and/or active agent in use, the strength of the preparation, the mode of administration, and the advancement of the disease condition. As is understood in the art, additional factors depending on the particular subject being treated will result in a need to adjust dosages, including subject age, weight, gender, diet, and time of administration.

In further aspects, the instantly-disclosed hydrogels and related compositions are capable of forming a hydrogel scaffold structure which is adapted to support cell growth. In aspects, the present disclosure is directed to a method of preparing a cell supporting medium as disclosed herein, the method comprising the steps of: (i) contacting a hydrogel and/or liquid hydrogel precursor composition as disclosed herein with at least one cell; and (ii) exposing the hydrogel to conditions such that the at least one cell is supported on and/or in the hydrogel, thereby forming a cell-supporting medium. In aspects, step (ii) comprises adjusting the pH of said comprises adjusting the pH of said aqueous solution such that hydrogel formation occurs, as previously described in detail. One of skill in the art understands how to culture various cell types with the hydrogel or liquid hydrogel precursor. As such, the methodologies (culture time, temperatures, growth media etc.) used will depend on the type of cell involved, and the final use of the cell-supporting medium (i.e., the hydrogen scaffold). In aspects, cells are able to infiltrate the hydrogel, e.g., at a treatment site in an individual, and therefor form a 3D cell-supporting medium. Thus, the cell-supporting medium can serve to replace and/or repair damaged or lost tissue at the treatment site.

All of the features described herein (including any accompanying claims, abstract and drawings), and/or all of the steps of any method or process so disclosed, may be combined with any of the above aspects in any combination, except combinations where at least some of such features and/or steps are mutually exclusive.

EXAMPLES

The following examples are given by way of illustration and are in no way intended to limit the scope of the present invention.

Example 1

Materials and Methods

Unless specified otherwise, the following experimental techniques were used in the Examples.

Peptide Synthesis

All peptides were synthesized by solid-phase chemistry in 0.1 mmol batches on a Tribute peptide synthesizer (Gyros Protein Technologies, AZ). A TentaGel R Rink Amide Resin was used which results in a C-terminal amide. Solvents and Fmoc (fluorenylmethoxycarbonyl)-protected AAs were purchased from Gyros Protein echnologies. Reagents were made with 5 equiv. moles of amino acid and 5 equiv. moles of HBTU (2-(1Hbenzotriazol-1-yl)-1,1,3,3-tetramethyluronium hexafluorophosphate), and subsequently dissolved in DMF (dimethylformamide). Amino acid coupling cycles were 60 min in length. Protecting groups were removed with treatments of 20/80 v/v piperidine/DMF for 10 minutes. After the coupling reaction was complete, the resin was washed three times with DCM (dichloromethane) before running the cleavage step. Cleavage of the peptides were accomplished by shaking the resin with 10 mL of TFA (trifluoroacetic acid)/triisopropylsilane/H2O (95:2.5:2.5 volume ratios) for 2 h at room temperature. The peptide solution was collected, and the peptide precipitated by the addition of cold diethyl ether followed by two washes with cold ether after centrifugation. The peptides were dried overnight, redissolved in deionized water and dialyzed with 10 water exchanges over 5 days using molecular weight cutoff of 100-500 Da (Spectra/Por, Spectrum Laboratories Inc., Rancho Dominguez, CA). Lyophilized peptides were stored at −20° C. and protected from light. MALDI-TOF (matrix assisted laser desorption ionization time-of-flight) analysis was used to characterize the mass of the final products. See FIGS. 17A-D-FIG. 23 for spectra.

Attenuated Total Reflection-Fourier Transform Infrared Spectroscopy (ATR-FTIR)

IR measurements were obtained for 3 wt. % peptides in PBS on a PerkinElmer 400 FT-IR spectrometer equipped with an ATR accessory. Aliquots of the peptide were deposited on a "Golden Gate" diamond ATR (PerkinElmer, USA). PBS was used as a background spectrum. Collected spectra were normalized by dividing all the absorbance values in the spectrum within the Amide I band by the largest absorbance value (Yang, H. Y., et al. Obtaining information about protein secondary structures in aqueous solution using Fourier transform IR spectroscopy. *Nat Protoc* 2015, 10 (3), herein incorporated by reference in its entirety), baseline corrected, and vertically offset for ease of comparison.

Molecular Dynamics Simulations of Pentapeptides

KYFIL, KYFAL, KAFIL and KYFIV peptides were constructed using the peptide builder tool in the program Avogadro (Hanwell, M. D., et al. Avogadro: an advanced semantic chemical editor, visualization, and analysis platform. *J Cheminformatics* 2012, 4, herein incorporated by reference in its entirety). A custom Tcl script was used to amidate the C-termini in VMD3 using the CHARMM36 forcefield4. Eighteen individual pentapeptides were solvated in a cube of explicit TIP3P water molecules, using VMD's solvation box extension; a 4-Å padding between the solute and nearest box face was used along with periodic boundary conditions. The pentapeptides were staggered 8 Å apart (as measured by their geometric centers) and rotated randomly so as to prevent orientational bias in the starting structures. The final simulation cell contains approximately 15,000 atoms (and varies with peptide sequences) with a rectangular parallelepiped box of water measuring 67 Å×71 Å×49 Å. Physiological concentrations (150 nM) of Na+ ions, including sufficient Cl-ions to neutralize the solute's charge, were added to the solvated system using VMD's ionize plugin. The internal energy was minimized for 10,000 steps, and the system was then equilibrated for 10 ns (with a 2-fs integration step) in the isothermal-isobaric ensemble (NPT) ensemble. Temperature (300 K) and pressure (1 atm) were regulated via Langevin dynamics for all non-hydrogen atoms and a hybrid Nosé-Hoover Langevin piston. Simulations were performed in NAMD 2.105, with final production trajectories extended to 200 ns. Trajectories were processed and further analyzed using in-house scripts written in the Python (Rossum, G. *Python reference manual*; CWI (Centre for Mathematics and Computer Science): 1995, herein incorporated by reference in its entirety) and D (Bright, W., The D programming language. *Dr Dobbs J* 2002, 27 (2), 36-40, herein incorporated by reference in its entirety) programming languages, as well as VMD. Secondary structures were assigned using STRIDE (Frishman, D.; Argos, P., Knowledge-based protein secondary structure assignment. *Proteins* 1995, 23 (4), 566-579; and Heinig, M.; Frishman, D., STRIDE: a web server for secondary structure assignment from known atomic coordinates of proteins. *Nucleic Acids Res* 2004, 32, W500-W502, herein both incorporated by reference in their entireties). Peptide structures were characterized via the SURF calculation (surface areas), with the solvent probe radius set to 1.4-Å and applied to all peptides; in this way, clusters were then defined as any peptides that have overlapping molecular surfaces, within 1.4-Å of each other. Density function plots were determined using a univariate kernel density estimate from the Python Seaborn package. Table 1 summarizes the peptide MD simulation systems. Grand average hydropathicity (GRAVY) values are computed from Kyte-Doolittle (KD) hydrophobicity (Kyte, J.; Doolittle, R. F., A Simple Method for Displaying the Hydropathic Character of a Protein. *J Mol Biol* 1982, 157 (1), 105-132, herein incorporated by reference in its entirety) indices averaged over the amino acid sequence for each peptide.

TABLE 1

Summary of MD simulation systems of the pentapeptide systems

| System Name | Trajectory Duration (ns) |
|---|---|
| KYFIL, KAFIL, KYFAL, AYFIL, KYFIV | Solvation, Minimization |
| KYFIL, KAFIL, KYFAL, AYFIL, KYFIV | Equilibration 10 ns |
| KYFIL, KAFIL, KYFAL, AYFIL, KYFIV | 200 |

Hydrogel Formation and Rheological Properties

Lyophilized peptides were dissolved in PBS to a final concentration of 1.5 or 3 wt. %. The pH of the peptide solutions was adjusted by drop-wise addition of minute amounts of HCl or NaOH. Rheological tests were performed on 50 μL hydrogels 30 minutes after induction of gelation (Anton Par, P25S 25 mm parallel steel plates) with a measuring gap of 250 μm. Storage (G') and loss (G") moduli were measured as a function of strain (%) ranging from 0.01 to 100% with a constant frequency of 10 rad/s. Frequency sweeps were performed at angular frequencies ranging from 1 to 100 rad/s at 0.1% strain. For recovery experiments, a step-time procedure was utilized with a series of applied strains at a fixed oscillation frequency of 10 rad/s. Initially, samples were applied with 0.01% strain for 100 s followed immediately by a 100% strain for 50 s, and cycled 5 times.

Transmission Electron Microscopy 3.5 μL of peptide hydrogel was placed on a holey carbon grid (Protochips, Inc.). Three washes of deionized water, and three washes of 2% uranyl acetate staining solutions with 2 s blotting between each step was performed. Samples were analyzed on a Tecnai F20 equipped with a 4k×4k UltraScan CCD camera. Pitch and length were determined using Fiji (Schindelin, J. et al., Fiji: an open-source platform for biological-image analysis. *Nat Methods* 2012, 9 (7), 676-682, herein incorporated by reference in its entirety) and the FiberApp software package (Usov, I.; Mezzenga, R., FiberApp: An Open-Source Software for Tracking and Analyzing Polymers, Filaments, Biomacromolecules, and Fibrous Objects. Macromolecules 2015, 48 (5), 1269-1280, herein incorporated by reference in its entirety) was used to compute autocorrelation functions of intensity profiles.

Cell Culture

GFP+ MADM OPC lines (Liu, C. et al, Mosaic Analysis with Double Markers Reveals Tumor Cell of Origin in Glioma. *Cell* 2011, 146 (2), 209-221, herein incorporated by reference in its entirety) were expanded in vitro on T75 tissue culture plates treated with poly-ornithine. OPCs were cultured in DMEM with high glucose, 4 mM L-glutamine, 1 mM sodium pyruvate (Life Technologies) with N2 and B27 supplement (Life Technologies), 1% penicillin-streptomycin (Life Technologies), 10 ng/ml mouse PDGFA-AA (eBioscience), and 50 ng/mL human NT3 (Peprotech). Cell media was changed every 2 days, and cells were grown to 90% confluency and passaged using 0.25% trypsin in Dulbecco's phosphate buffered saline (PBS). Cells were cultured in 5% $CO_2$ atmosphere, and 21% $O_2$ at 37° C.

Hydrogel Cell Encapsulation and Analysis

Hydrogels for cell encapsulation were made using 1.5 wt % AYFIL peptide in PBS. 25 μL hydrogels with $5\times10^6$ cells/mL were made by mixing cells and peptides and then transferred to a cell incubator for 10 minutes at 37° C. at 100% humidity. OPC proliferation media was then added to the hydrogels, and changed every 2 days. Hydrogels were stored at −80° C. in lysis buffer before running ATP or DNA quantification assays. For quantification, gels were homogenized in lysis buffer using a hand grinder and were measured using the CellTiter-Glo luminescent Cell Viability Assay (Promega, United States) and the QuantiT PicoGreen dsDNA assay (ThermoFisher) according to manufacturer protocols.

Syringe Needle Flow Viability Assay

OPCs were resuspended at a cell density of $1\times10^5$ cells/mL in either PBS or 1.5 wt. % AYFIL hydrogels, and loaded into a 1-mL syringe with an 18-gauge needle, mounted onto the syringe pump, and ejected onto a 24 well plate at a constant volumetric flow rate of 1000 μL/min. Cell viability was assessed with a dead stain assay (Invitrogen). Briefly, hydrogels were rinsed for 10 minutes in PBS plus glucose (PBSG), and stained with 4 μM ethidium homodimer-1 for 40 minutes in PBSG, and rinsed in PBSG prior to imaging. GFP+/dead images were collected using a Zeiss LSM 510 confocal microscope. 150 μm z-stack images were collected with a frame distance of 1 μm. For image analysis, channels for live cells in the green channel and dead cells in the red channel were split and analyzed separately, and converted to 8-bit to allow for thresholding based on the intensity. The Find Maxima plugin was used for each channel to count the number of dead or live cells. Using the point selection tool, the Noise Tolerance values were adjusted by increments of 5 until background staining was excluded (the Noise Tolerance value was 50 for all images). The number of points for each channel were recorded, and were used to calculate the percentage of live and dead cells. Total cell count was between 146 and 287 for each image (n=3 samples per condition). Statistical significance was determined using the Student's t-test with $p<0.05$.

Immunostaining

After 2 days of culture, gels were fixed in 4% paraformaldehyde for 20 minutes at 4° C. and rinsed with PBS before permeabilizing overnight with 0.3% triton-X in PBS. Hydrogels were rinsed in PBS, and then incubated with 10 μg/mL stock solution of Alexa Fluor 568 Phalloidin (ThermoFisher) in 1% BSA in PBS overnight. 4',6-diamidino-2-phenylindole (DAPI) was added to stain cell nuclei during the last 20 minutes of incubation. Gels were then washed 4×20 min in PBS and imaged with a Zeiss LSM 780 confocal microscope. 100 μm z-stack images were collected with a z-spacing distance of 1 μm.

Example 2

Results and Discussion

The instantly-disclosed and designed pentapeptides, in aspects based on a KYFIL-$NH_2$ sequence (FIGS. 1A-1C) hereafter referred to simply as "KYFIL", can self-assemble into β-sheet-forming nanofibers. The sequence KYFIL was chosen based on previously published results on aromatic-rich tripeptides that could gel under certain experimental conditions (such as a change in pH or ionic strength). In particular, we chose Lys as the headgroup to improve solubility in aqueous solution, while the overall sequence design was guided by the goal of increasing the hydrophobicity of amino acid residues so as to increase the amphiphilicity of the peptides. In initial screens, we assayed several peptide designs by performing an alanine scan. Displaying the results as a sequence logo revealed that the central phenylalanine (F), as well as preservation of the amphiphilicity of the sequence, are two key elements that facilitate hydrogel formation (FIGS. 1A-C and FIG. 2). Interestingly, the carboxyl-terminated variant KYFIL-$CO_2H$ (i.e., with "natural" peptide end-chemistry) did not readily form hydrogels at pH 7.4. Because the carboxylic acid moiety is deprotonated at neutral pH, this finding suggests that an uncharged C-terminus may be required for gelation of the peptide. By examining the peptide's secondary structural conformation via ATR-FTIR spectroscopy and MD simulations, we detected that structural transitions occur when a pentapeptide self-assembles under gelling conditions.

Secondary Structure Analysis Via FTIR Spectroscopy

The secondary structural content of pentapeptide specimens was probed by ATR-FTIR spectroscopy. Samples of the pentapeptides of interest were generated via solid-phase peptide synthesis methods. An alanine (Ala) scan of KYFIL was used to assess each AA's contribution to gelation, wherein individual amino acids (AAs) were sequentially exchanged with Ala or Val. Ala and Val were the substituted residues of choice, as they either eliminate a side-chain beyond the CB atom (Ala) or otherwise would be expected to minimally alter the main-chain conformation (Val). As uncharged and relatively compact residues, Ala and Val would not be expected to introduce (confounding) electrostatic or steric effects. All pentapeptides were dissolved in phosphate-buffered saline (PBS) at a concentration of 1.5% or 3% (weight/volume) and adjusted to a pH of 7.4. Gelling peptides (solid lines, FIG. 2) display a strong amide I absorbance at ≈1629 $cm^{-1}$, arising from vibrational modes of the amide group; these vibrations, in the region of 1700→1600 $cm^{-1}$, correspond to stretching of the C═O and C—N bonds, as well as bending of the N—H. This region of the IR spectrum is particularly sensitive to variations in secondary structural conformation and, in the case of our pentapeptide samples, is indicative of β-sheet hydrogen bonding (FIG. 2, FIG. 12, and FIGS. 13A-B). A secondary peak near 1679-1683 $cm^{-1}$, in some of the specimens, indicates that the β-sheet is antiparallel. This can be inferred because the amide I region of parallel β-sheets harbors a single predominant signature (near 1630 $cm^{-1}$), while antiparallel sheets generally feature a second (minor) peak near ≈1680-1690 $cm^{-1}$. Peptide variants which do not form gels at the same concentration and pH (dashed lines, FIG. 2) exhibit less intense peaks, suggesting a lack of significantly structured hydrogen bonding networks in those solutions. By correlating our IR observations with variations in AA sequence, it appears that amphiphilicity and a capacity for π-system interactions (e.g., π •••π stacking and π ••• cation interactions with the benzyl side-chain of the central Phe) play a key role in self-assembly and hydrogel formation (FIG. 2).

Probing the Conformational Space and Interaction Events Via MD Simulations

MD simulations were used to examine the atomically detailed molecular interactions underlying peptide self-assembly processes. MD simulations offer a powerful approach to examine the structural properties and conformational dynamics of engineered peptides and can yield experimentally inaccessible insight about the dynamical basis of self-assembly. Simulations can help guide adjustments to the peptide sequence in order to optimize the system's properties toward a target goal. Using MD simulations, one can study a peptide system's aggregation propensity by simulating multiple peptides together in a single system. While other work has focused on the diffusional association of protein molecules within a solvated system or detailed the biomolecular recognition events (i.e., conformational rearrangement and binding/unbinding events), few examples exist of using computational approaches to design functional peptide scaffolds for tissue regeneration applications. In this study, we used MD simulations to study the emergence of structural features in a peptide system and provide an atomistic view of the self-assembly process of nanostructures.

Figures 3A, 3B:
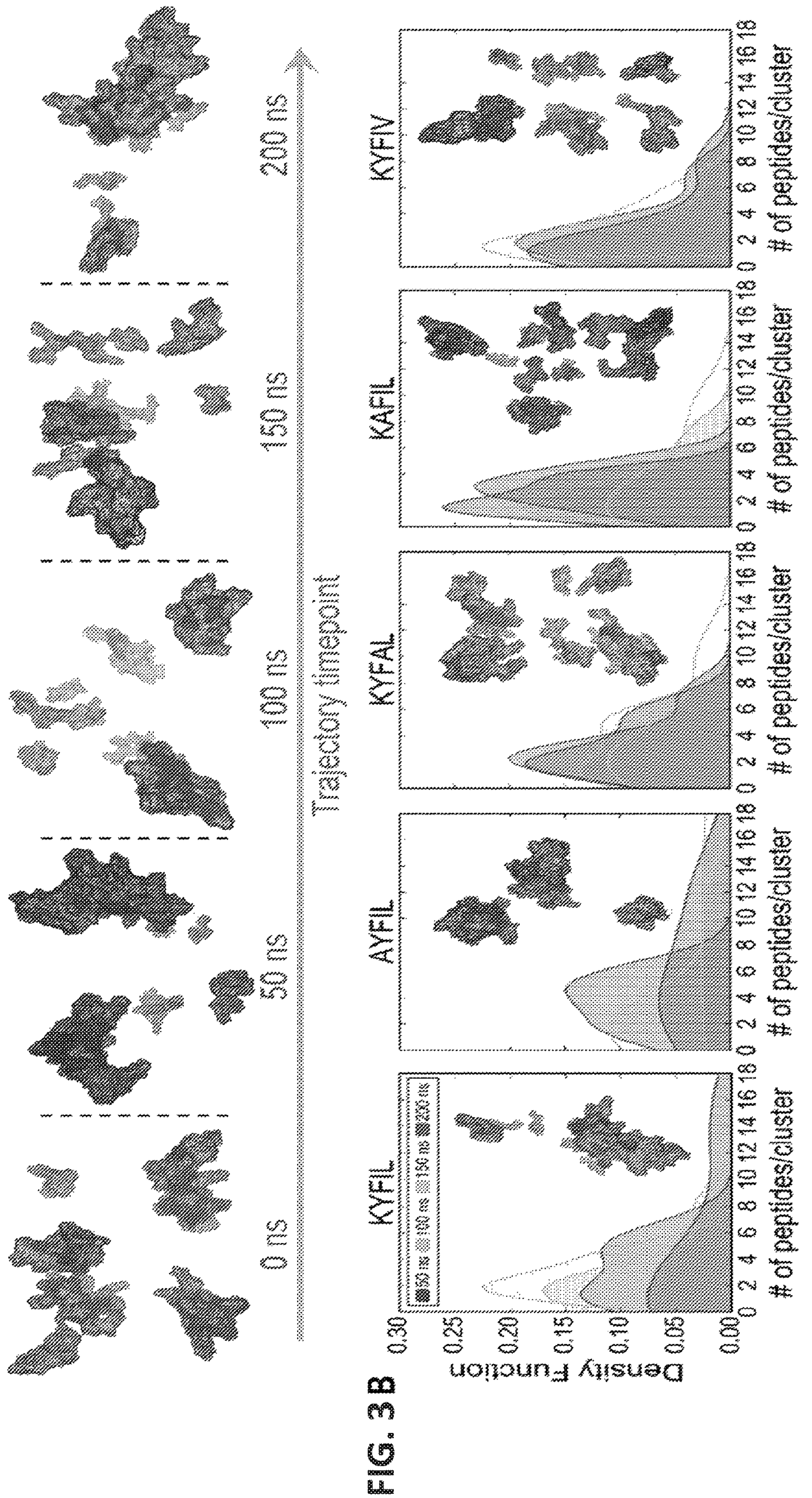
FIGS. 3A-B demonstrate that KYFIL peptide molecules simulated in explicit solvent assemble into multimeric structures.
Figure 11:
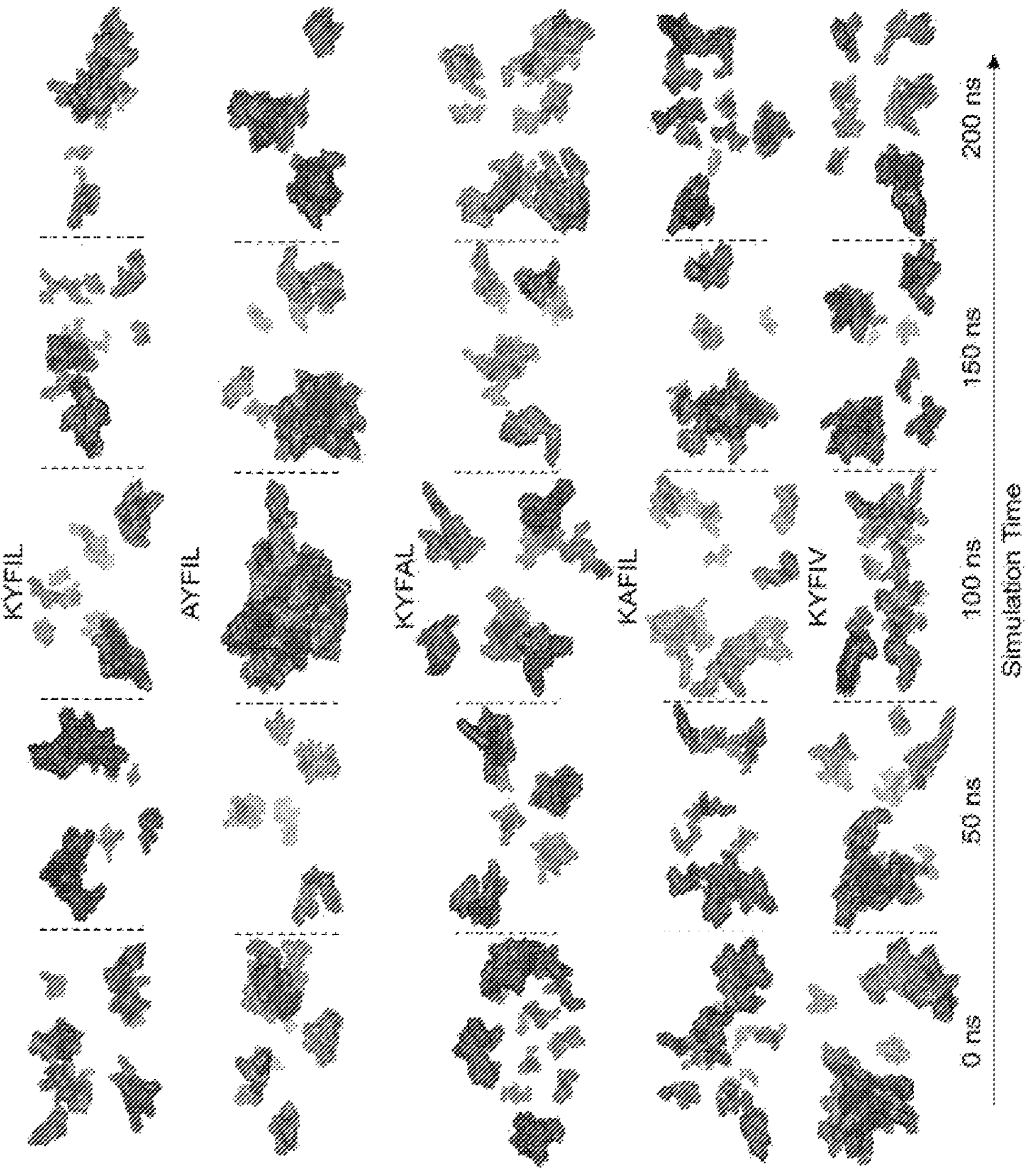
FIG. 11 depicts representative snapshots of KYFIL, KYFAL, KAFIL, and KYFIV peptide systems at increasing time points following minimization and equilibration. Snapshots were taken after minimization for 10,000 steps, and equilibration for 10 ns. MD simulations were conducted for 200 ns, and peptide systems were simulated with an explicit water solvent (TIP3 solvent model). For experimentally-determined gelling peptides (KYFIL, AYFIL, KYFAL, KAFIL) the number of peptide clusters decreases as the simulation progresses, highlighting their aggregation propensity.
Figure 12:
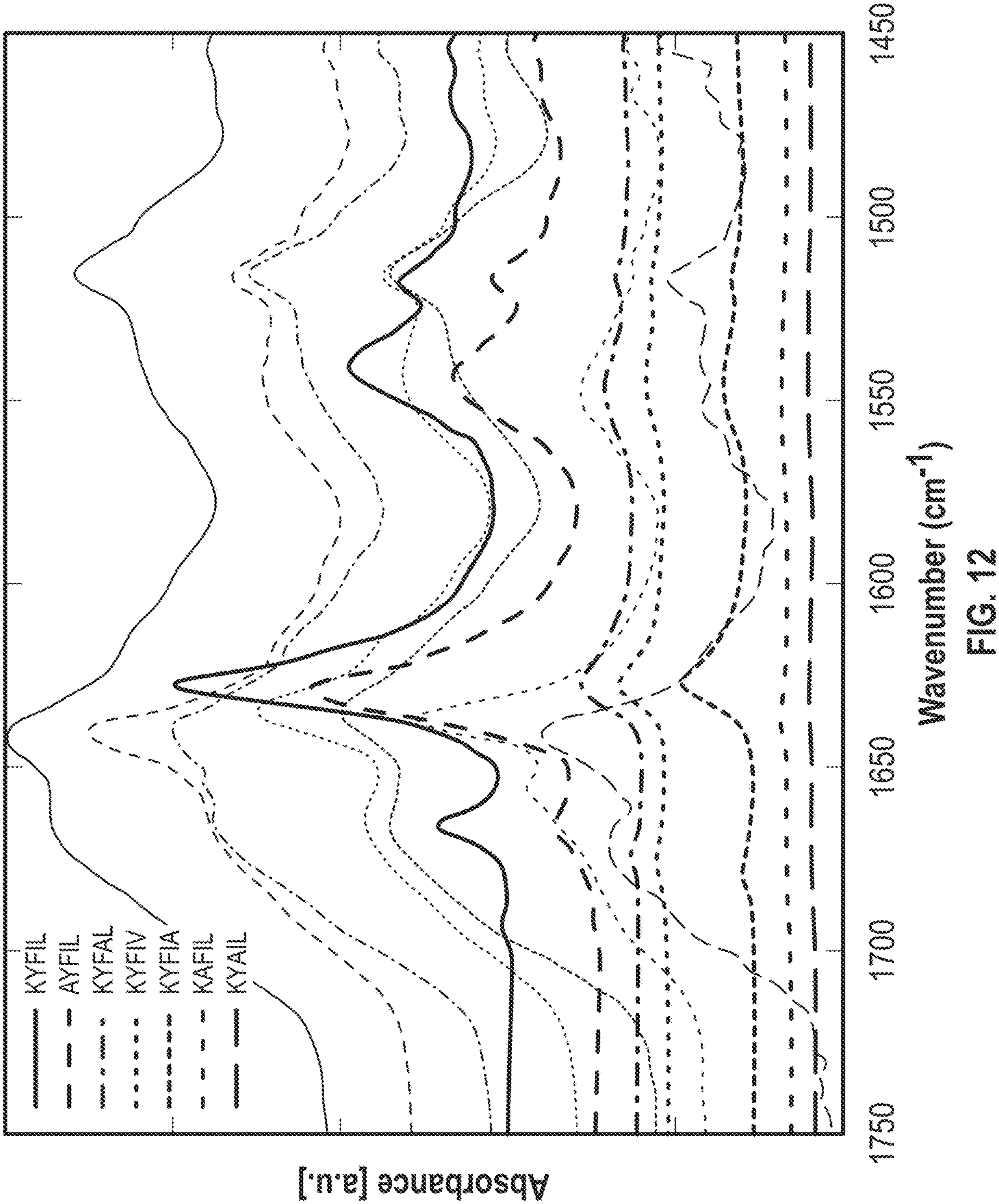
FIG. 12 depicts the ATR-FTIR spectrum of peptides in PBS (thick lines) and freeze-dried peptides (thin, transparent lines). All peptides that are able to gel at pH 7.4 (solid lines) exhibit an Amide I absorbance at 1629-1645 cm-1, indicative of β-sheet hydrogen bonding. Non-gelling peptides in the same conditions (dashed lines) exhibit much weaker, less intense peaks at the same wavenumbers. All spectra are baseline corrected, normalized, and offset for clarity.

To elucidate the molecular-scale events associated with self-assembly, after having experimentally established pentapeptide sequences that can assemble in aqueous media, we conducted MD simulations of select peptide candidates (FIGS. 3A-B). These extended (200 ns), all-atom simulations were performed in explicit solvent using the CHARMM (Ogata, S. et al. Concurrent coupling of electronicdensity-functional, molecular dynamics, and coarse-grained particles schemes for multiscale simulation of nanostructured materials. Mater. Sci. Forum 2005, 502, 33-38, herein incorporated by reference in its entirety) force-field. Such force-fields represent the physicochemical properties of each amino acid (including partial charges, atomic interaction (Lennard-Jones) potentials, and other parameters) via a classical, molecular mechanics-based approach, as described in various primers (Mura, C. et al. An introduction to biomolecular simulations and docking. Mol. Simul. 2014, 40 (10-11), 732-764, herein incorporated by reference in its entirety). In practice, CHARMM is a state-of-the-art force-field that can be applied to many types of biomolecular systems, as illustrated for instance by the analysis of disordered regions of the protein desmoplakin (McAnany, C. E. et al. Disorder, and Conformational Dynamics of the C-Terminal Region of Human Desmoplakin. J. Phys. Chem. B 2016, 120 (33), 8654-8667, herein incorporated by reference in its entirety). Our simulations show that the assembly propensity of RAPID peptides correlates with the diffusional association of individual peptides. The peptides primarily adopt irregular conformations, with some transiently stable β-turns "flickering" into existence. Within ≈50 ns, individual KYFIL peptides assemble into six discrete groups of peptides, as can be seen by visual inspection of trajectories, with some β-sheet secondary structure (FIG. 11 and FIG. 3A). Extending the simulation further yields peptides that have assembled into two large clusters by ≈200 ns (FIG. 3A).

Figure 14:
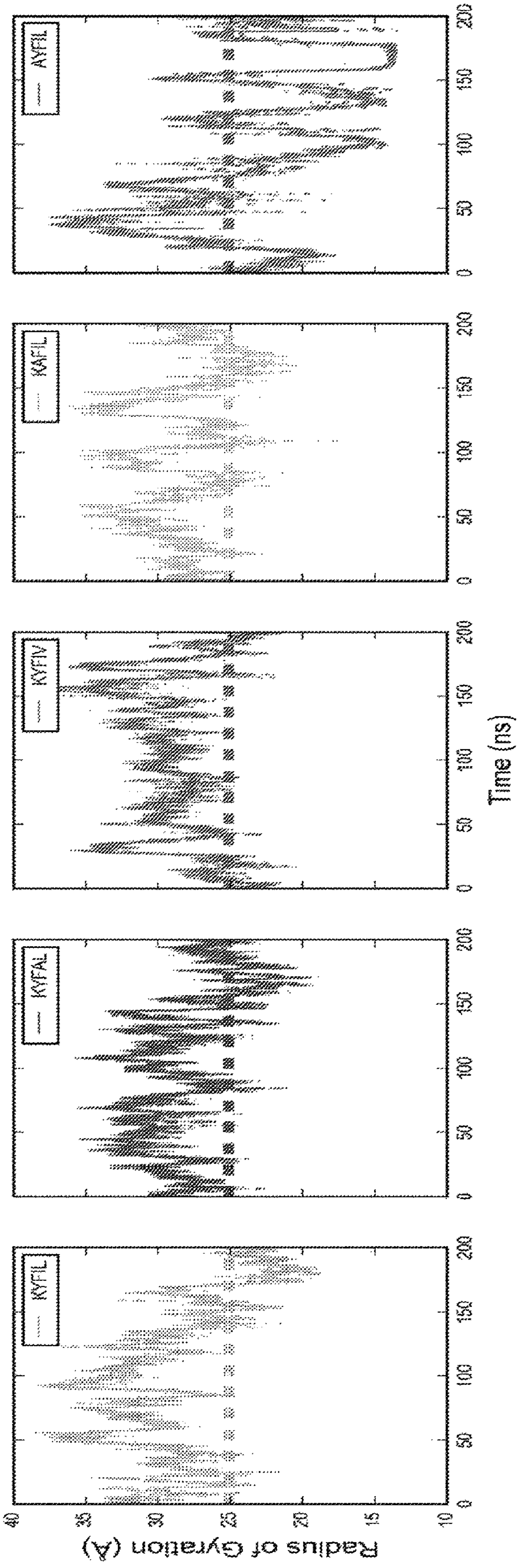
FIG. 14 shows sequence dependence of the radius of gyration ($R_g$). The $R_g$ was measured for an ensemble of 18 peptides of different sequences (KYFIL, KYFAL, KYFIV, KAFIL, and AYFIL) after equilibration of 10 ns. All peptides incur hydrophobically-driven collapse (relative to initial starting structure). Dashed line indicates initial $R_g$ before equilibration. Towards the end of the simulation, the $R_g$ for KYFIL and AYFIL decreases relative to the beginning of the trajectory, highlighting their aggregation propensity.
Figure 15A:
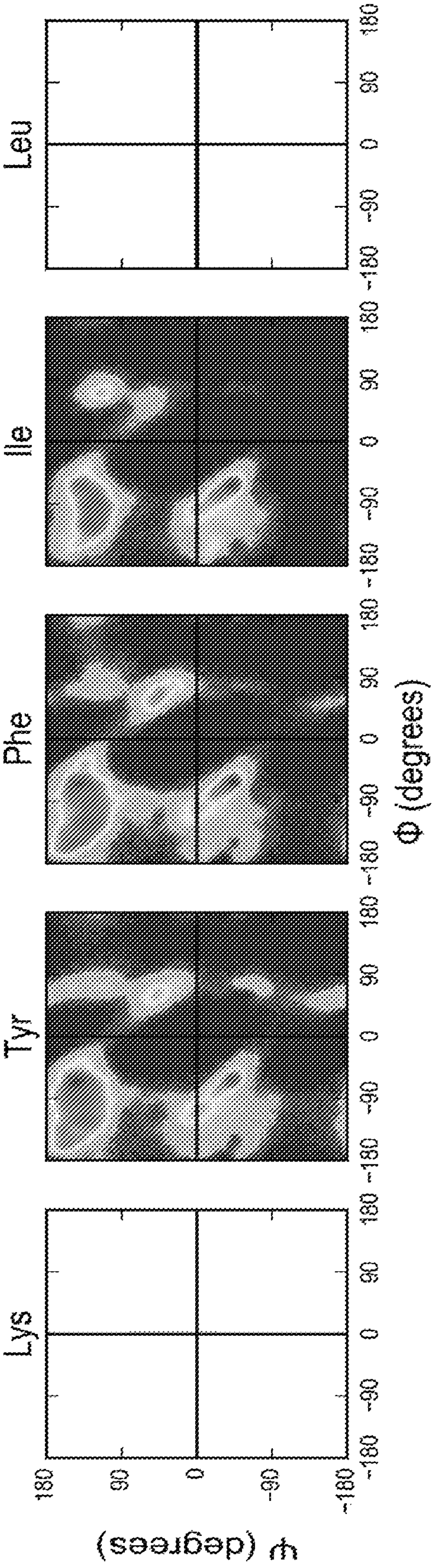
FIGS. 15A-E show a Ramachandran plot (ϕ, ψ distributions) for each residue in a pentapeptide sequence.
Figure 15B:
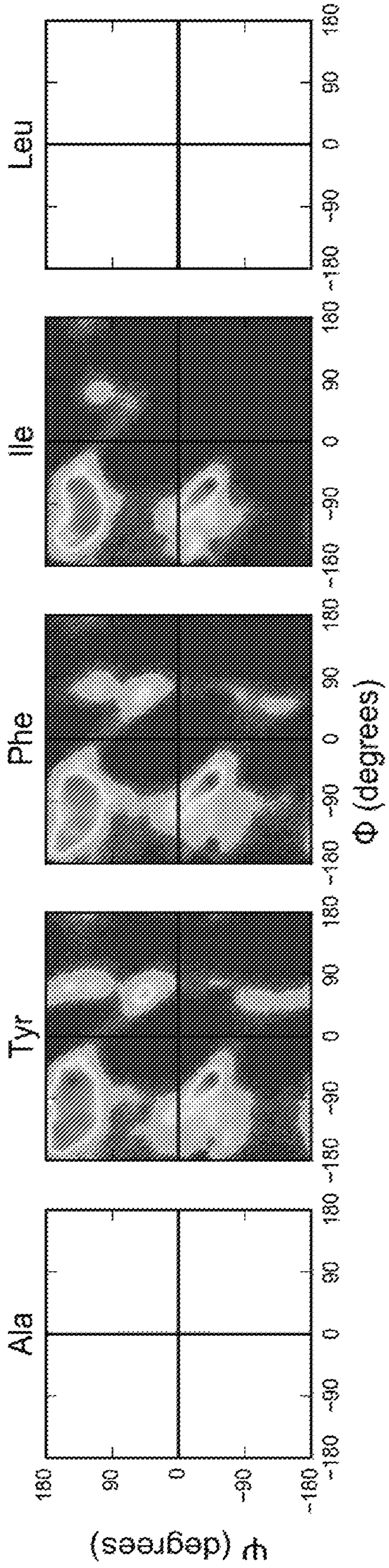
Figure 15C:
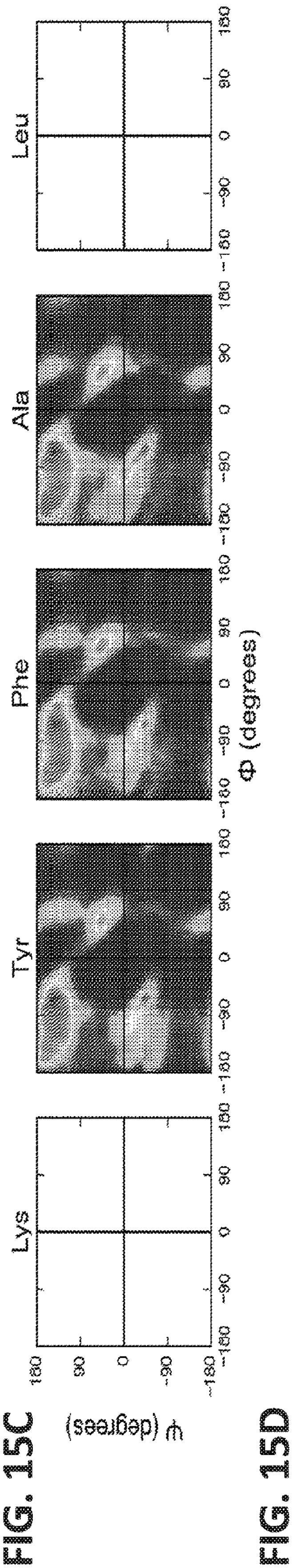
Figure 15D:
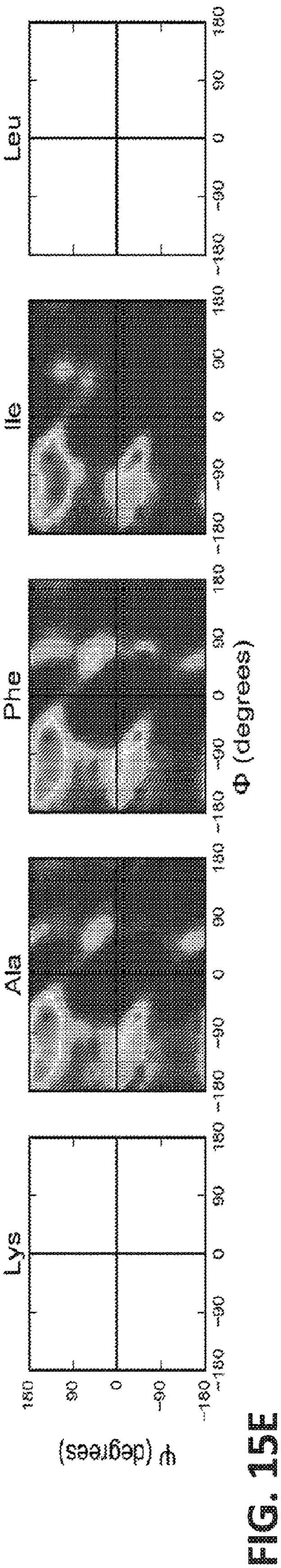
Figure 15E:
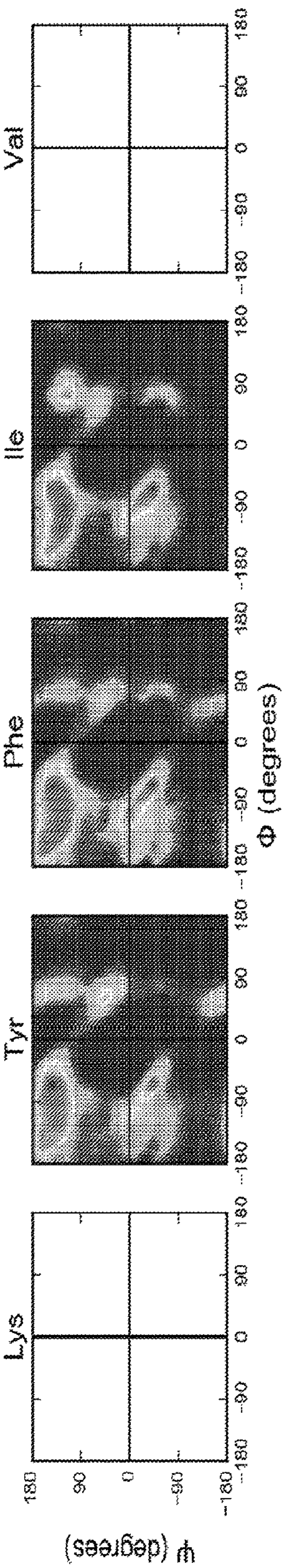
Figure 16B:
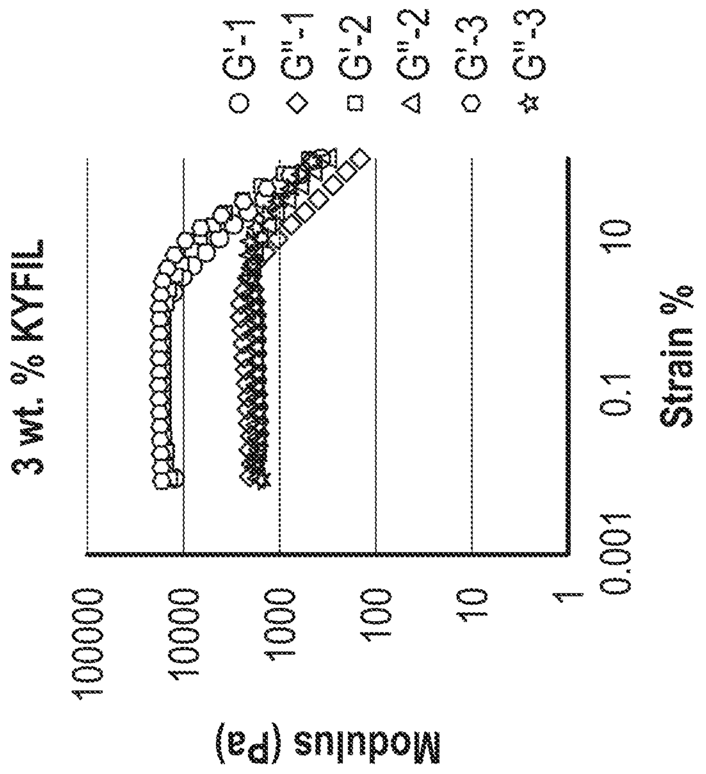
FIG. 16A-B depict strain sweeps of gelling KYFIL sequences at constant frequency of 1 hz. Measurements are carried out at 3 wt. % (FIG. 16A) and 1.5 wt % (FIG. 16B). For all sequences, G' decreases significantly in acidic conditions. Higher concentrations of peptides exhibit increased G'. Legend indicates 3 sample replicates.
Figure 16A:
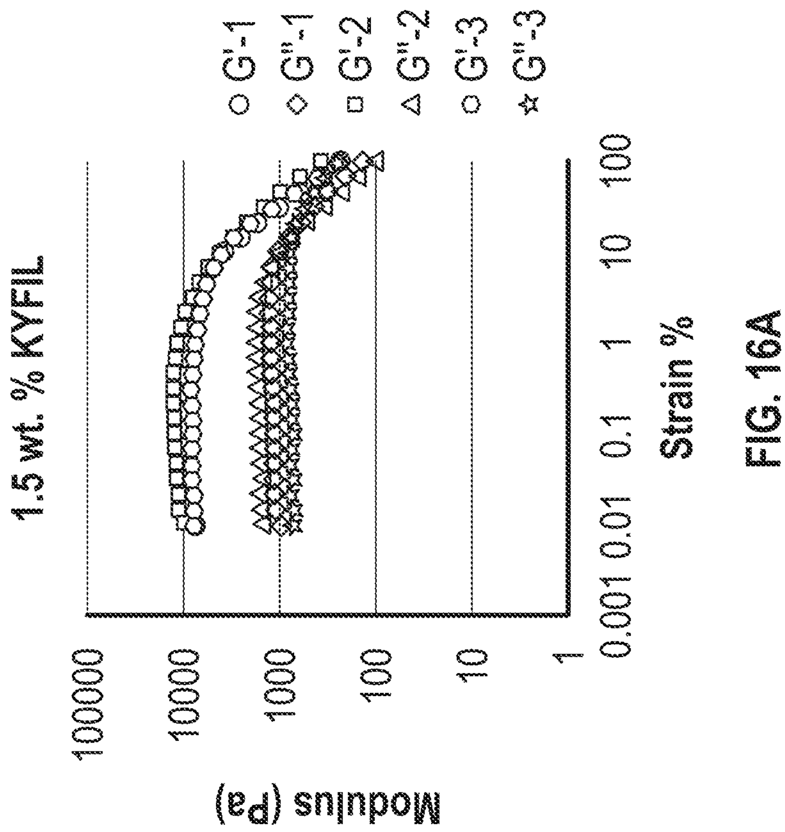
Figure 17A:
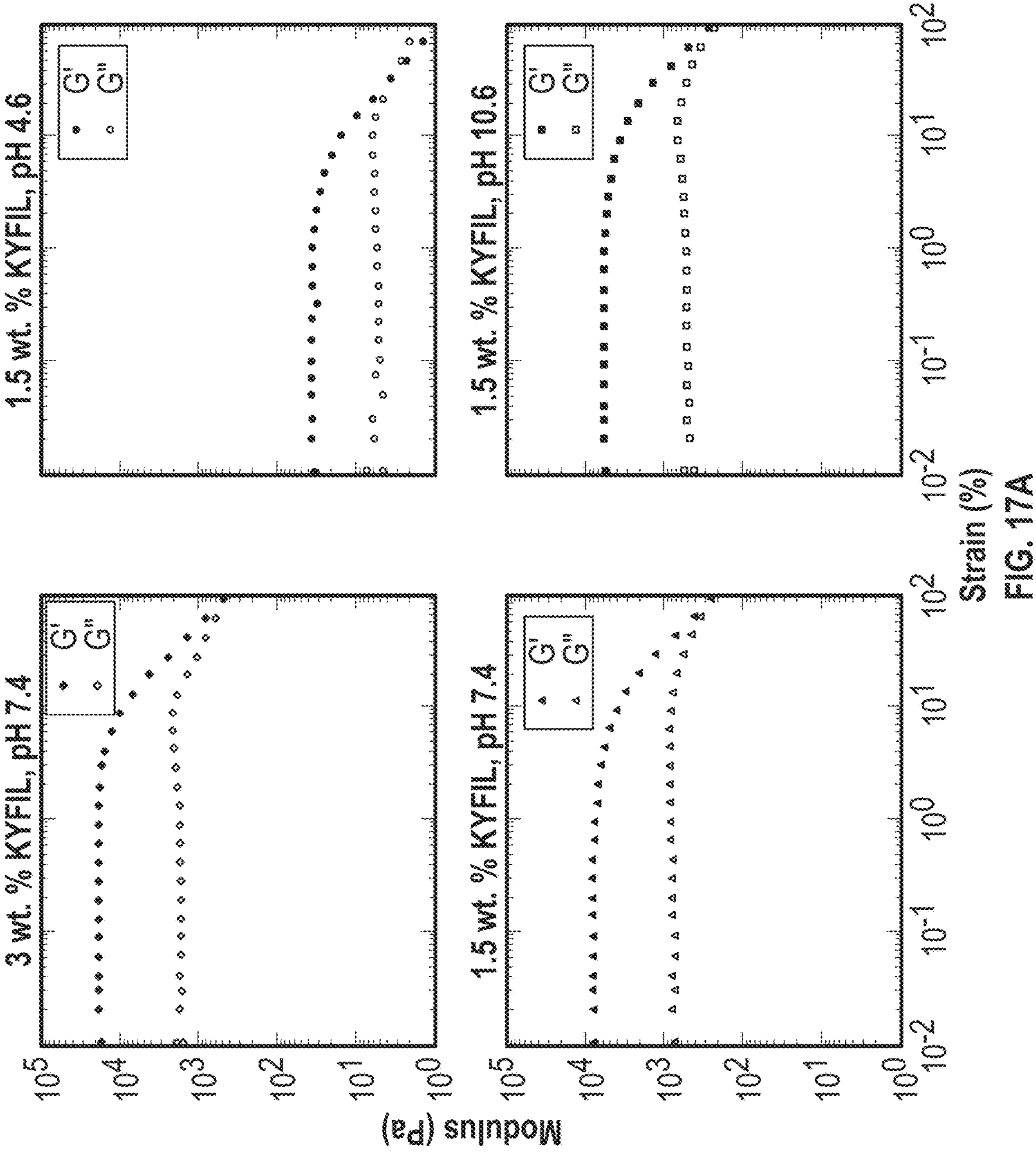
FIGS. 17A-D depict strain sweeps of gelling pentapeptide sequences at constant frequency of 1 hz. Measurements are carried out at 3 wt. % and 1.5 wt. %, and different pH conditions (4.6, 7.4, 10.6).
Figure 17B:
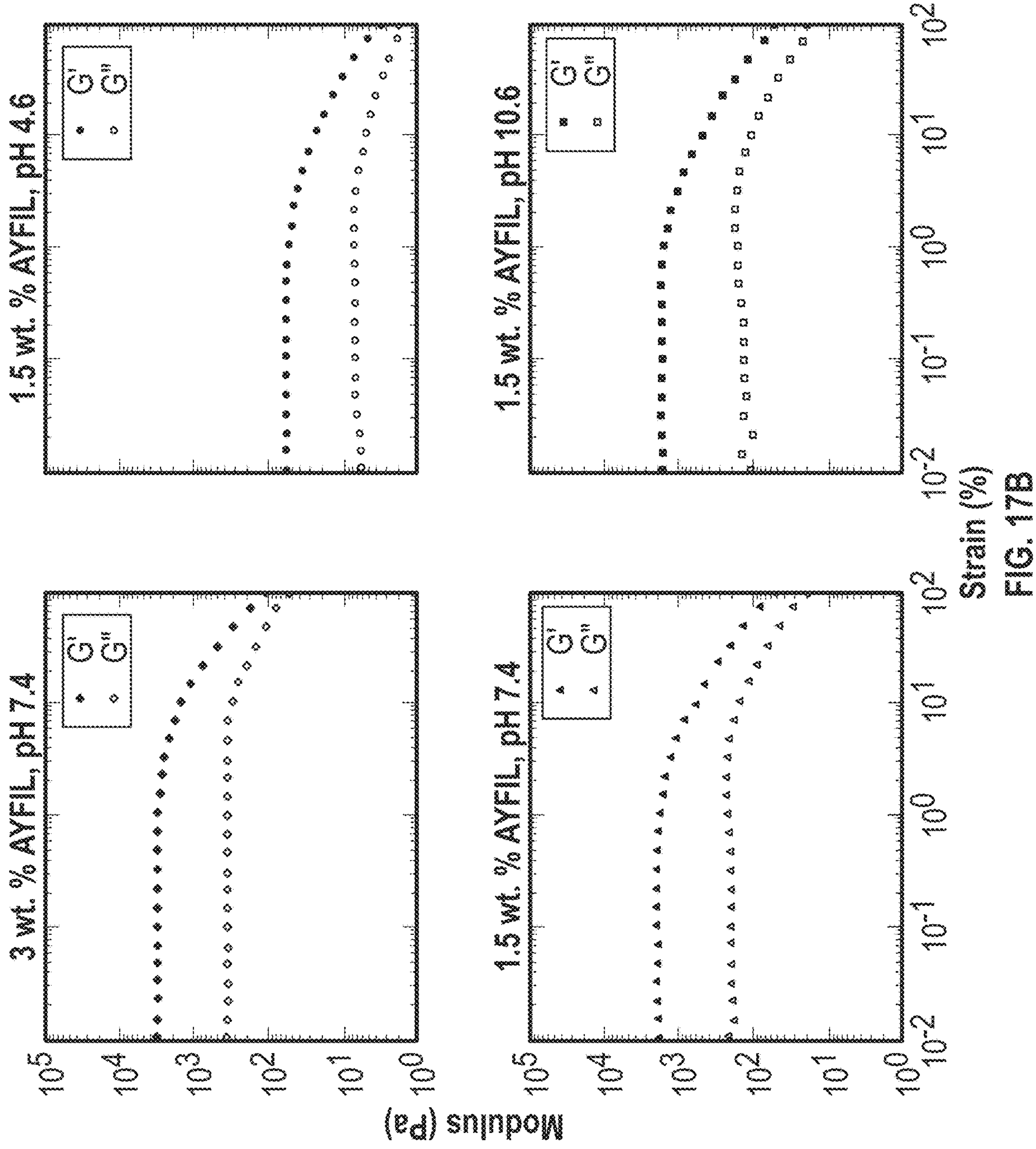
Figure 17C:
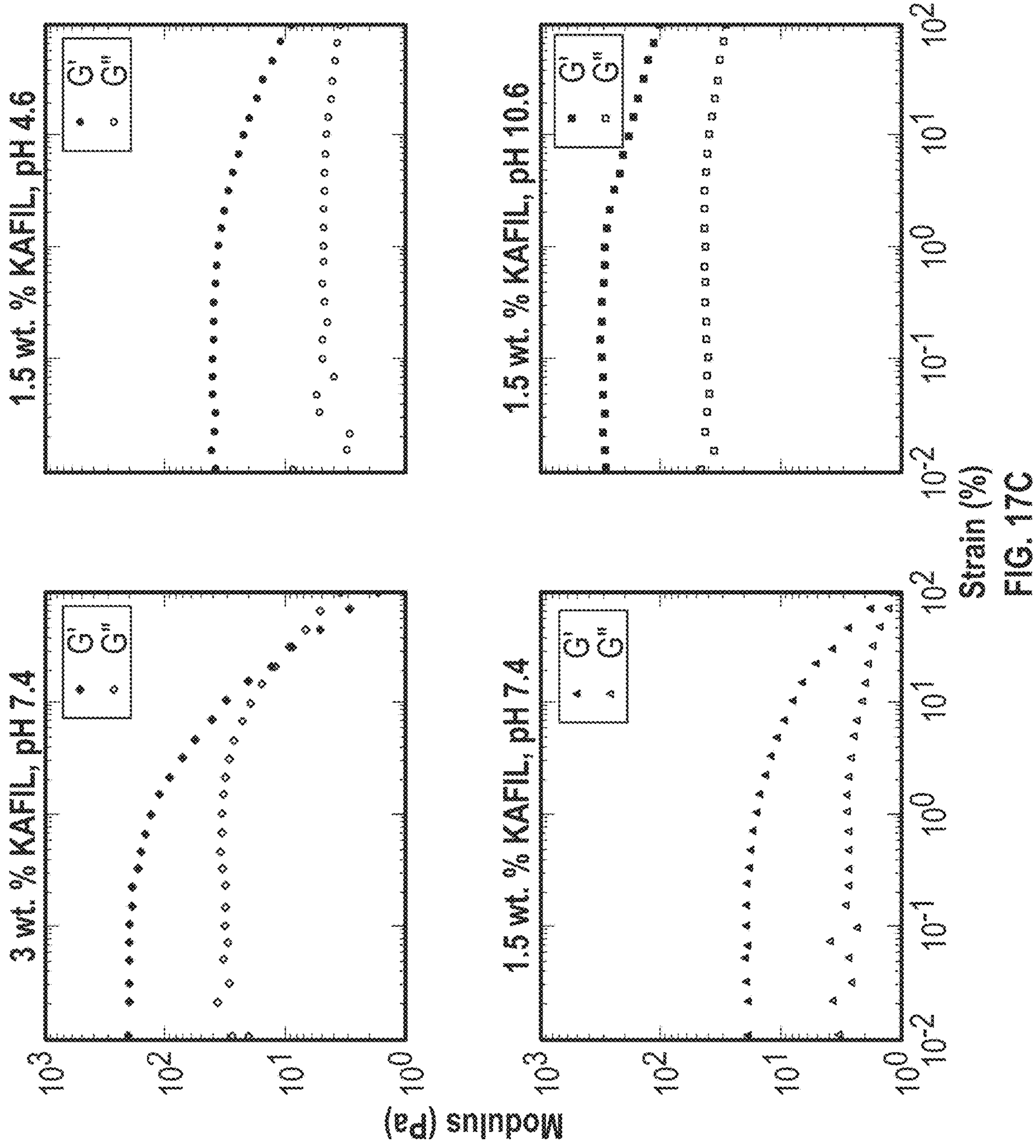
Figure 17D:
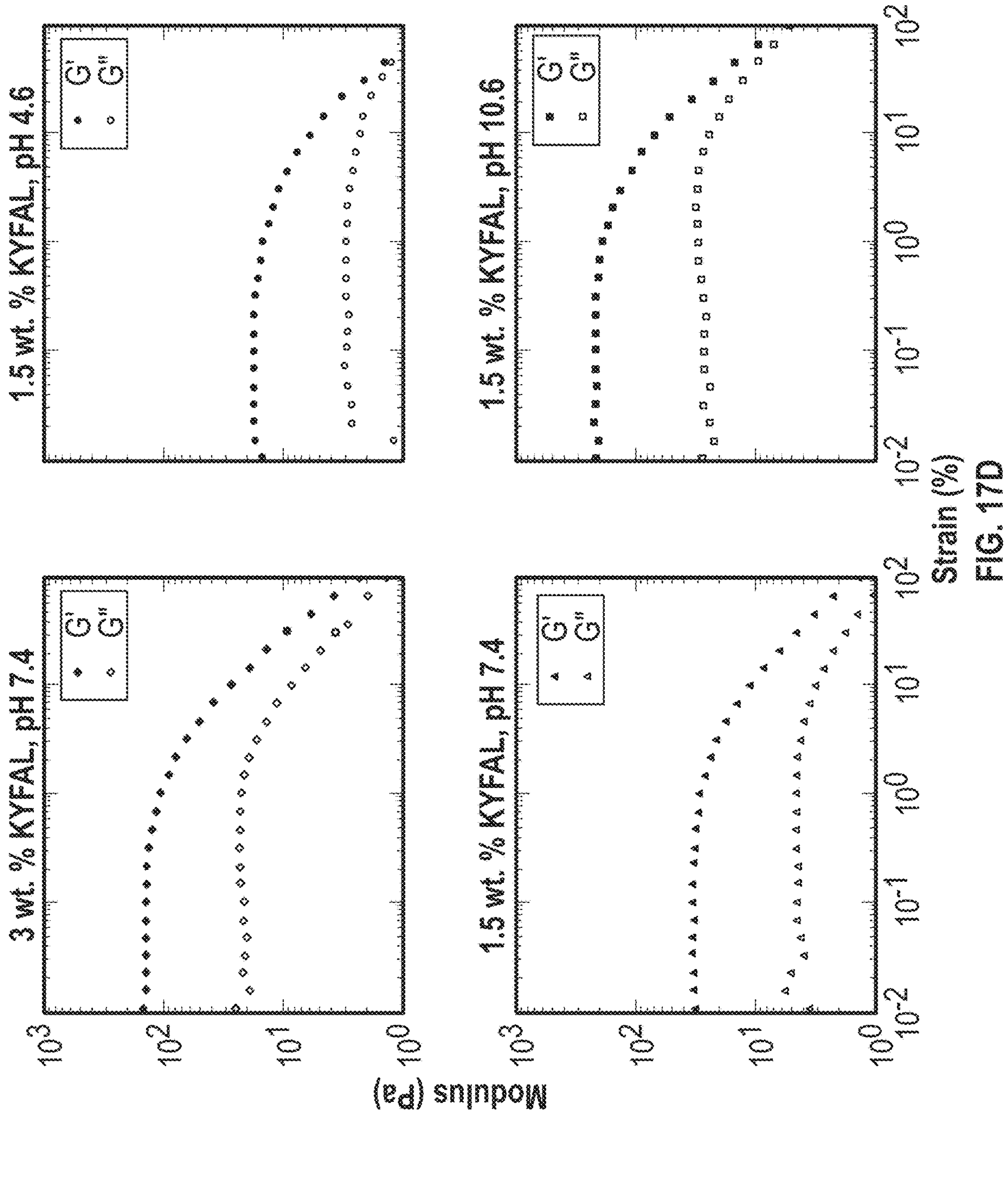
Figure 18A:
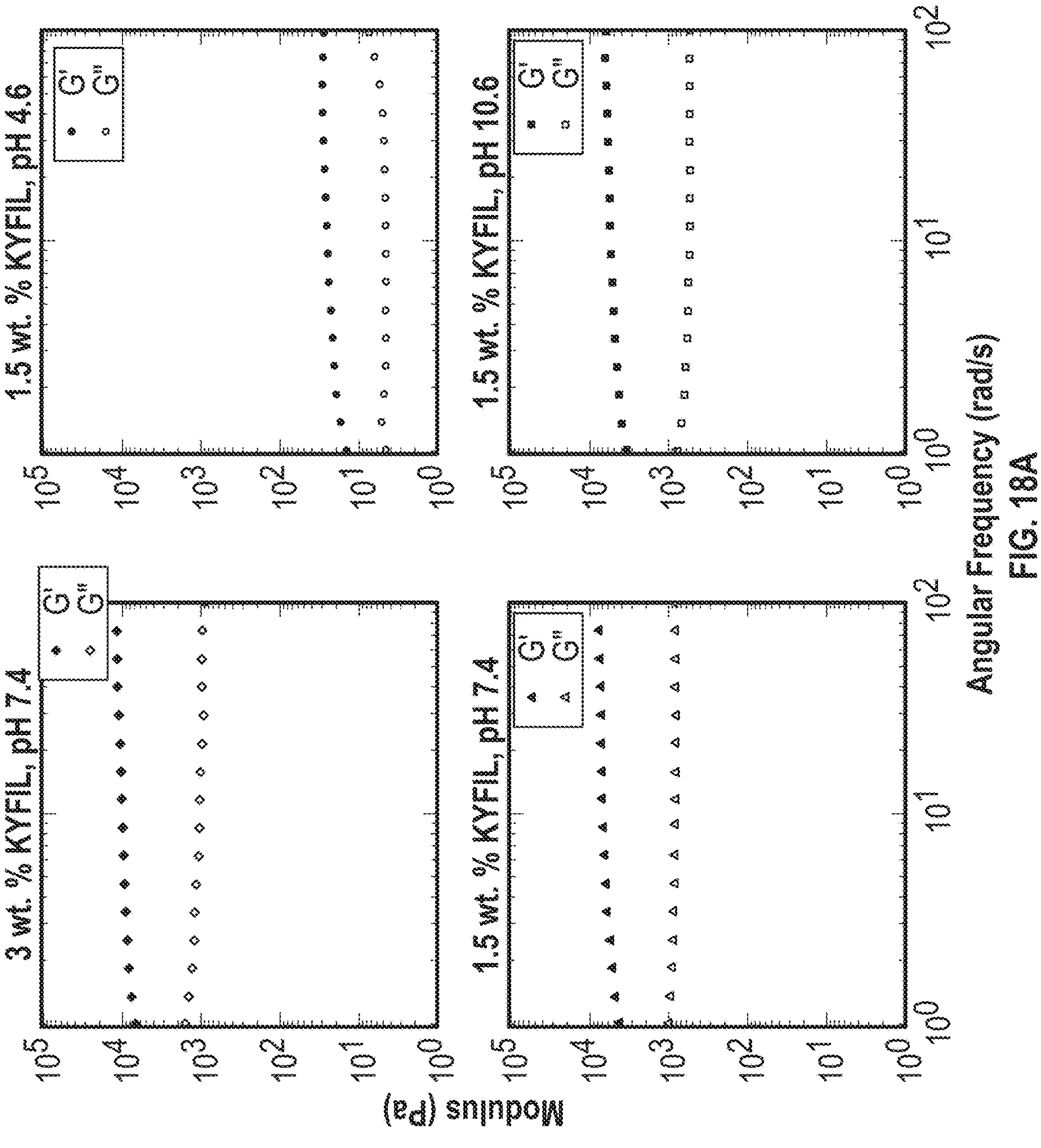
FIGS. 18A-D depict frequency sweeps of gelling pentapeptide sequences at constant strain at 0.1%. Measurements are carried out at 3 wt. % and 1.5 wt. %, and different pH conditions (4.6, 7.4, 10.6).
Figure 18B:
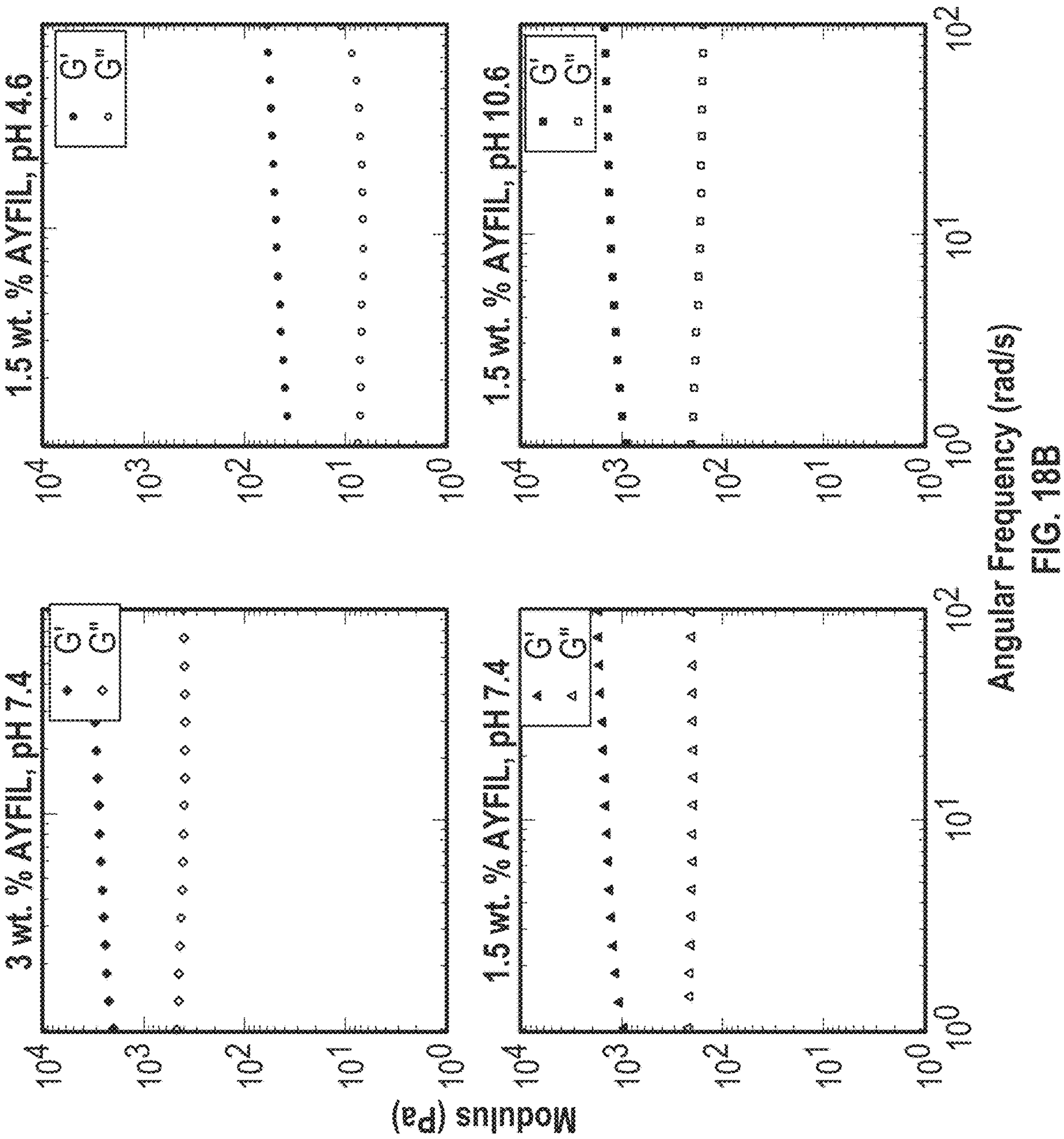
Figure 18C:
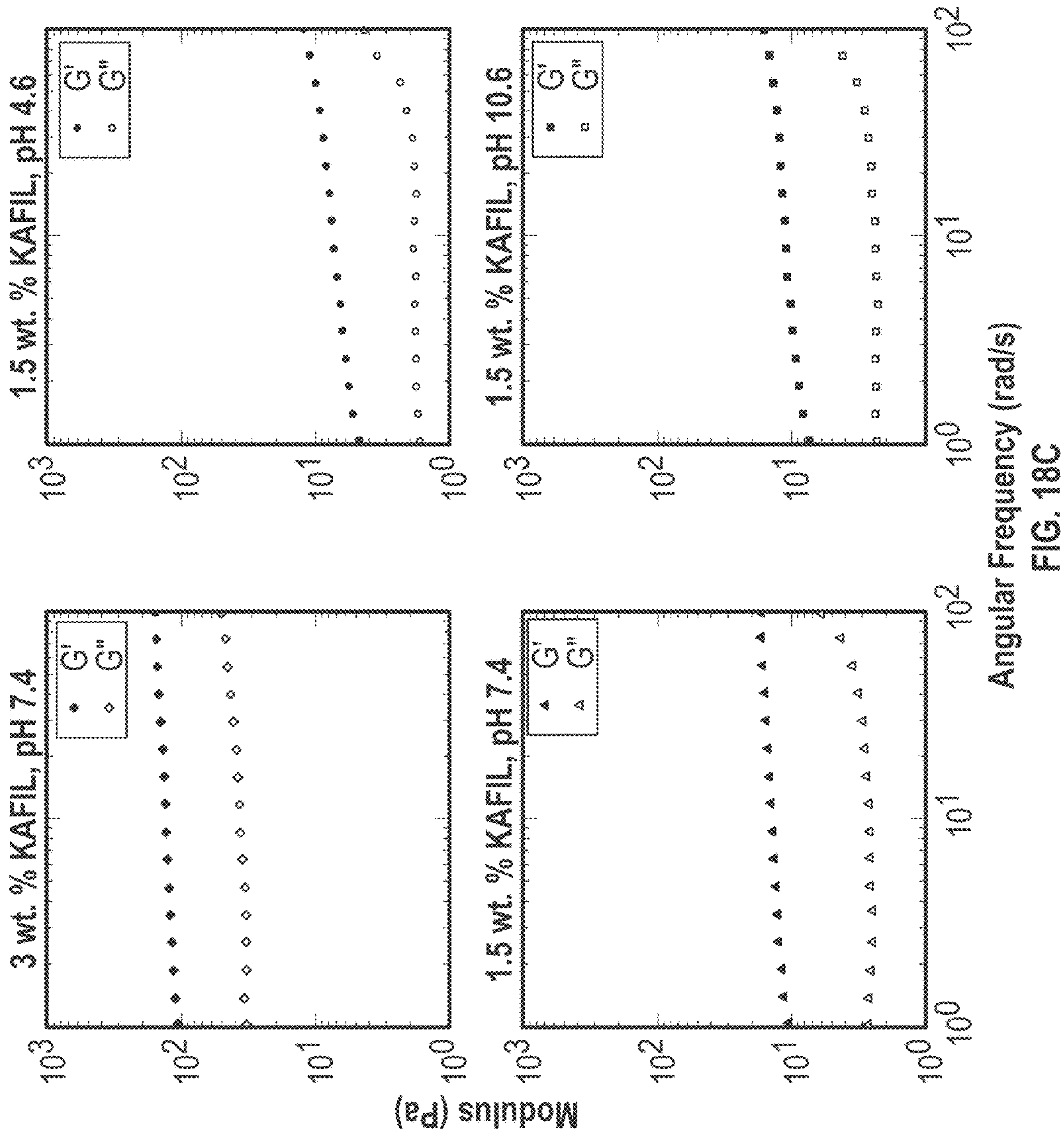
Figure 18D:
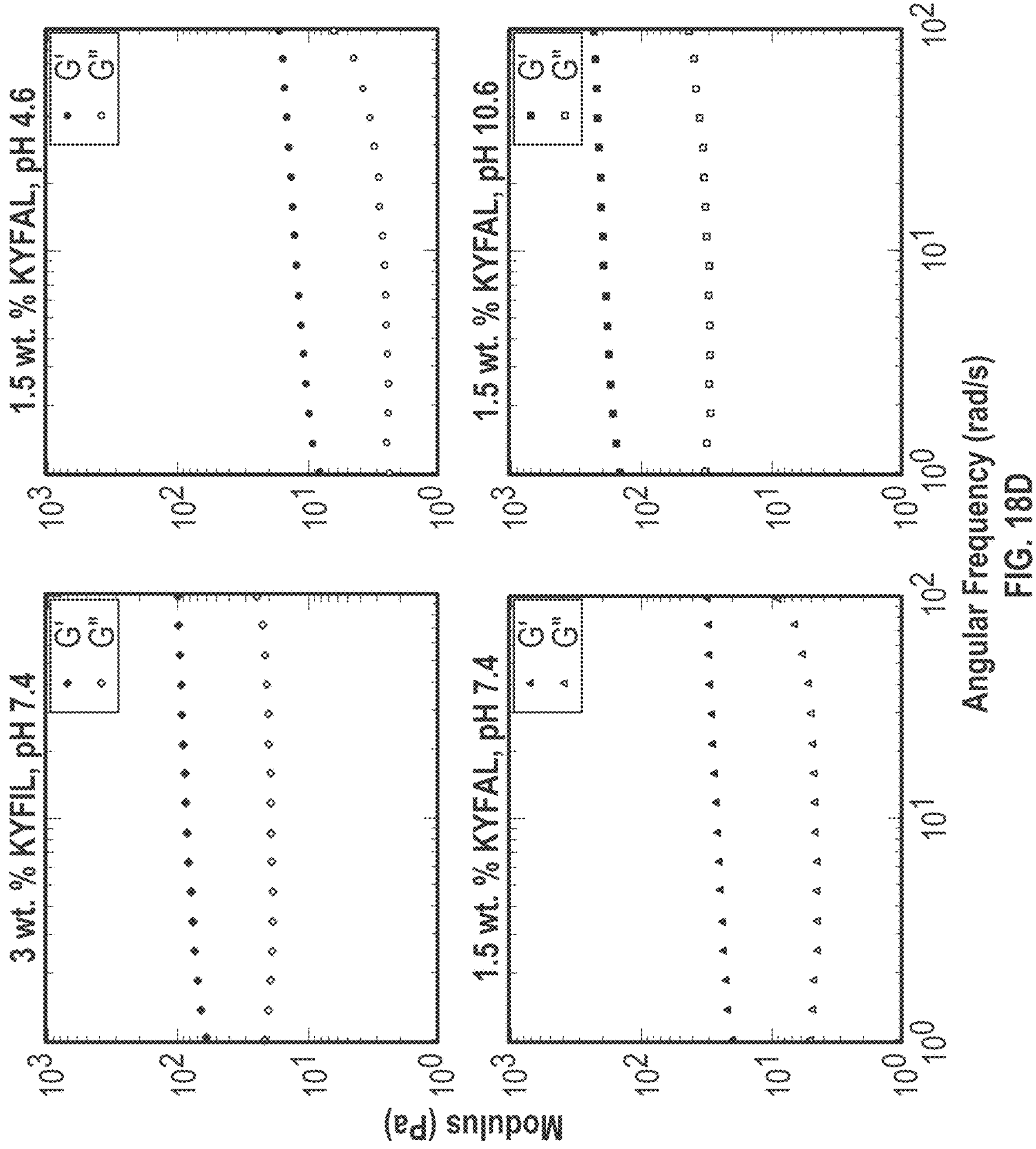
Figure 19:
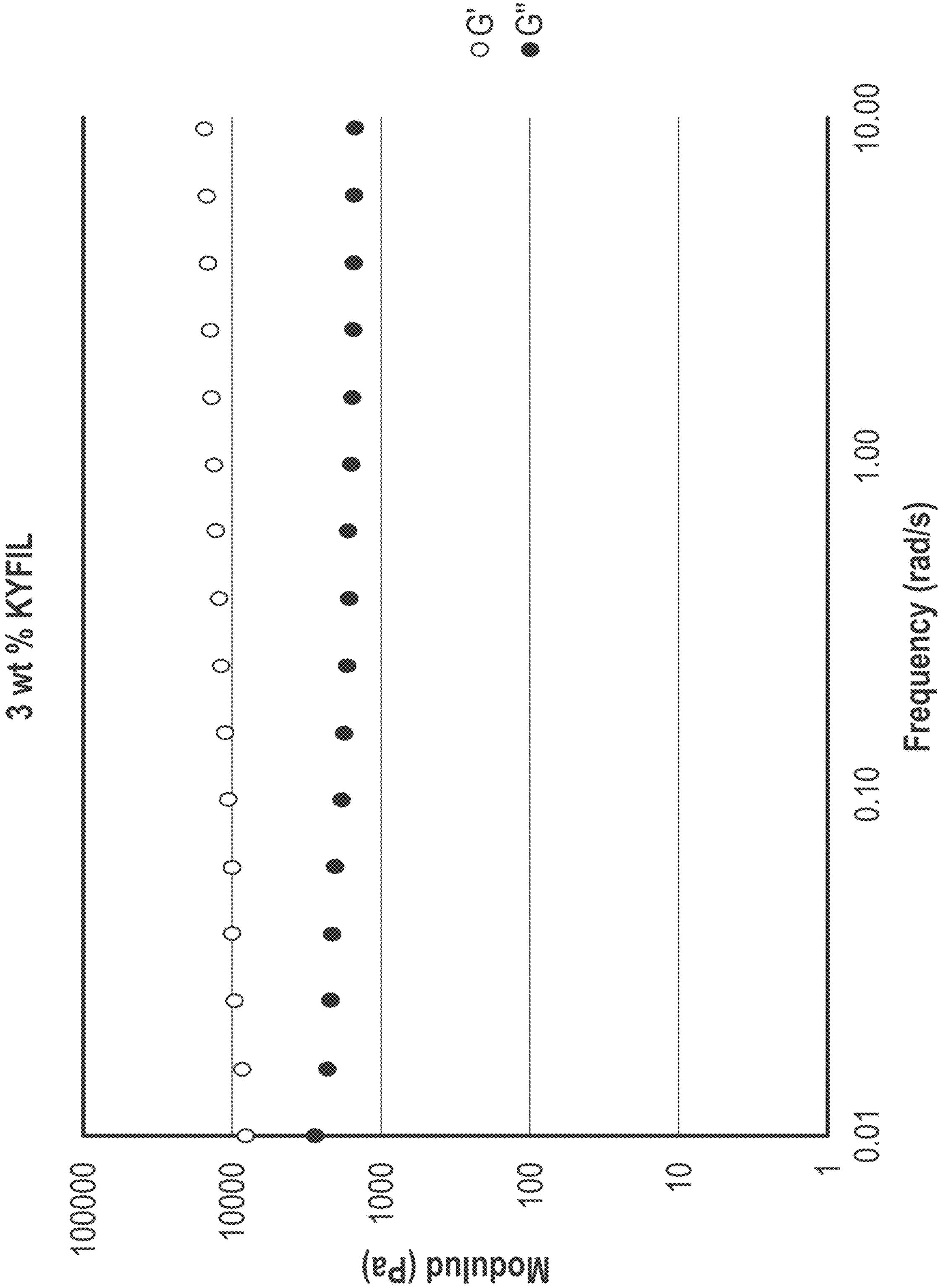
FIG. 19 depicts frequency sweeps of gelling pentapeptide sequence KYFIL at constant strain at 0.1%. Measurements are carried out at 3 wt. % from 0.01 to 10 rad/s to investigate the inherent dynamics of the hydrogel network.
Figure 20A:
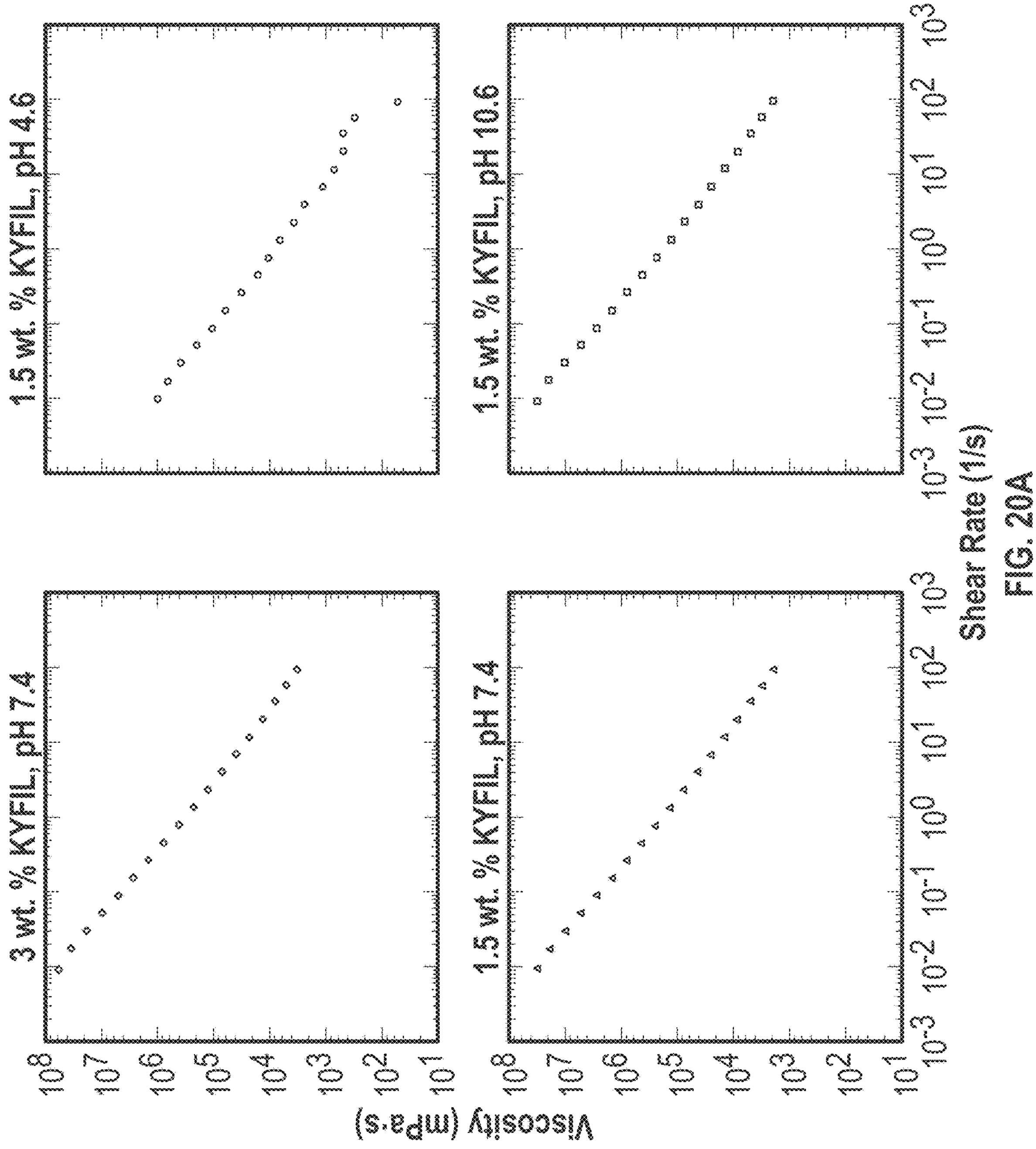
FIGS. 20A-D depict apparent viscosity versus shear rate measurements of gelling peptide sequences at different wt. % and pH conditions.
Figure 20B:
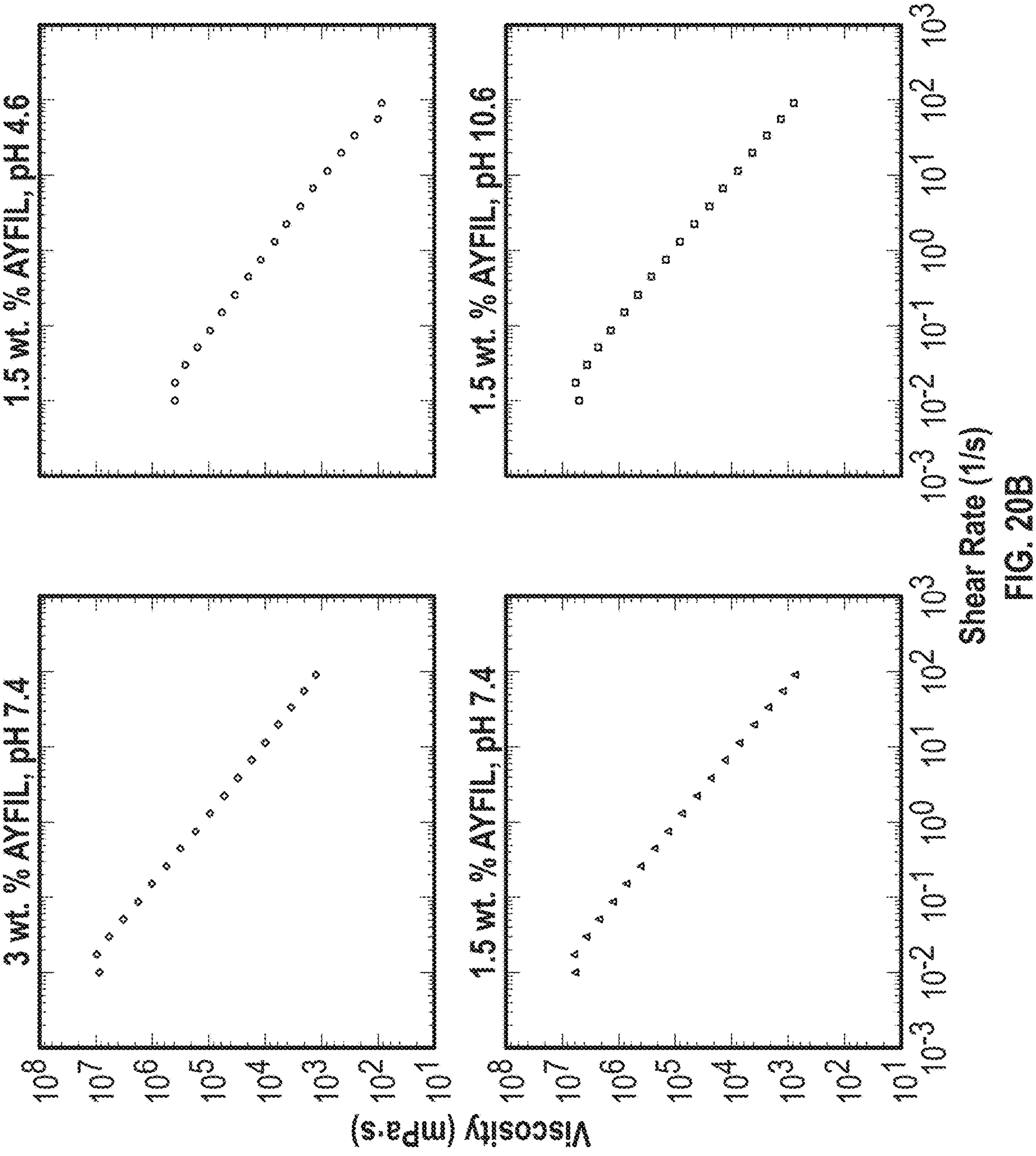
Figure 20C:
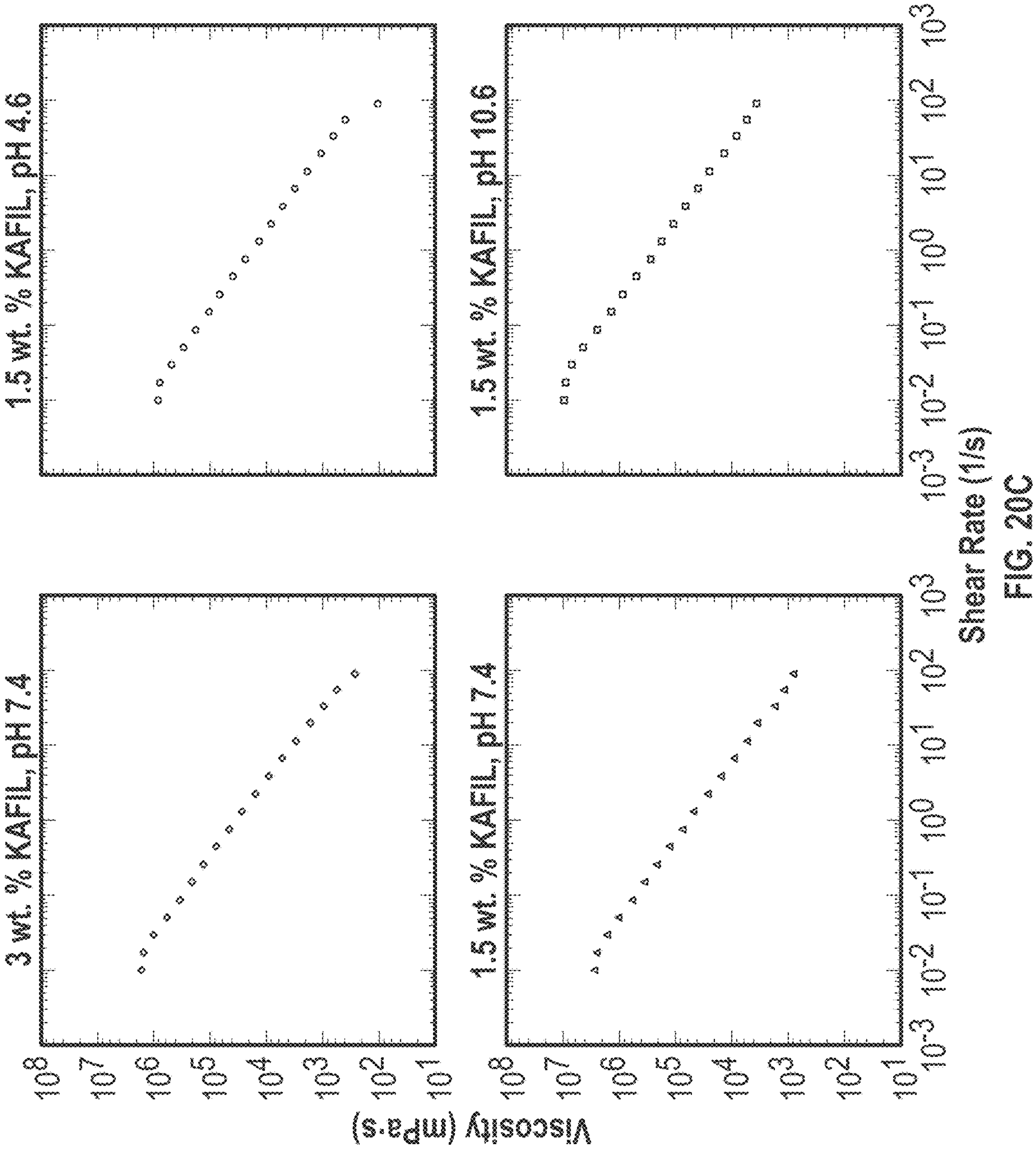
Figure 20D:
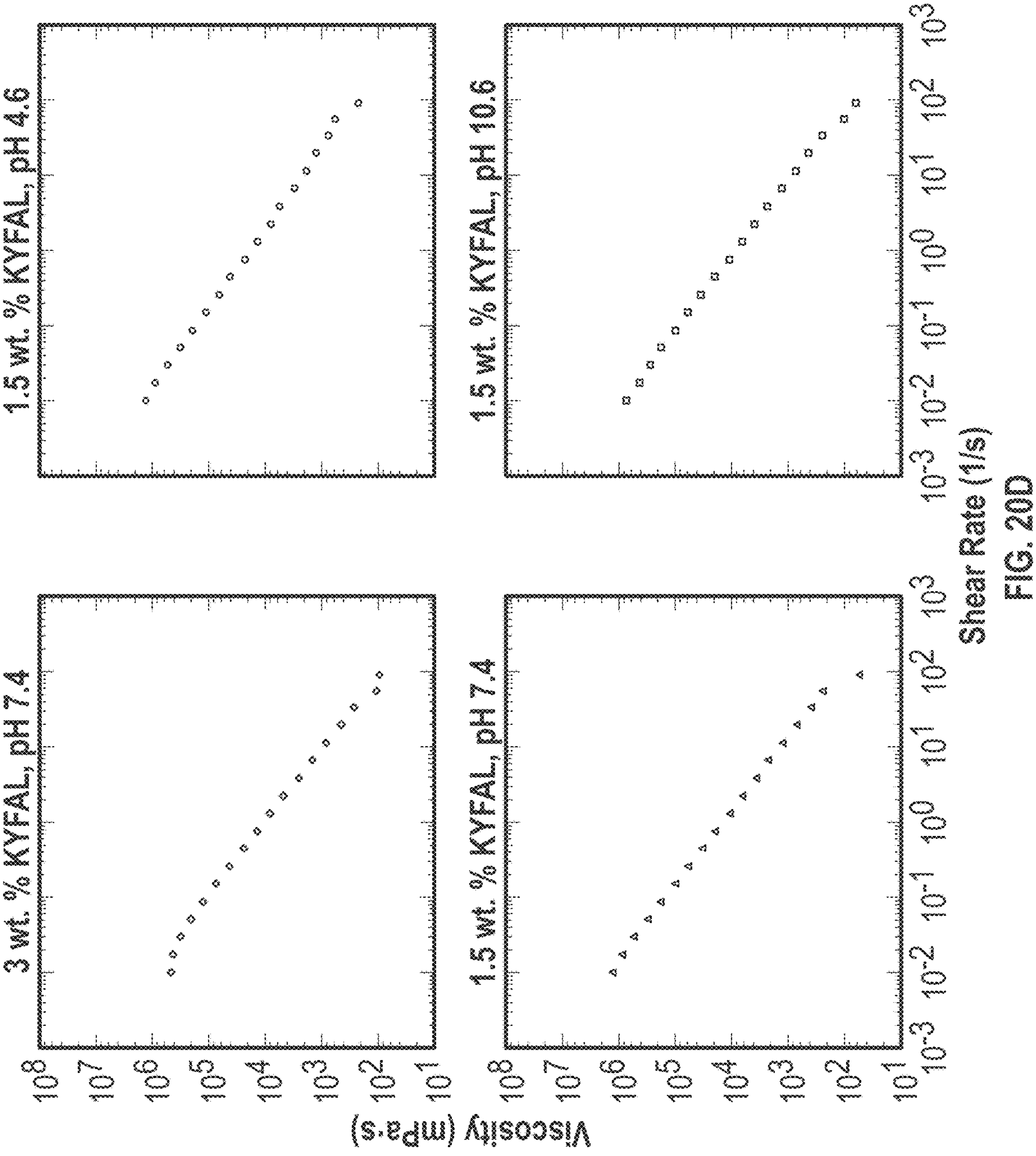

We used a discrete number-density function (a measure of the local concentration) to quantify the aggregation propensity of the four different peptides along their respective trajectories. Those sequences which were found to gel in experiments (KYFIL, AYFIL, KYFAL, and KAFIL at pH 10) exhibited a higher propensity to aggregate; those peptides which formed gels also tended to exhibit greater variation in the number of peptides per cluster at 200 ns, consistent with a higher propensity to assemble, even non-specifically into heterogeneous aggregates (FIG. 3B). In addition, the time-evolution of the radius of gyration ($R_g$) of the peptide systems ($R_g$ computed system wide across all peptides, not per-peptide) reveals a gross structural rearrangement, from mostly diffuse peptides to closely associated molecular interactions, as indicated by the net decrease in $R_g$ for pentapeptide sequences (FIG. 14) relative to the initial trajectory, except for KAFIL, KYFAL, and KYFIV. These data are consistent with the FTIR spectra (FIG. 2), as KAFIL, KYFAL, and KYFIV have lower β-sheet peak intensities, suggesting lower assembly propensity. For KYFIL, a detectable, and presumably hydrophobically driven, "collapse" of the system appears to be more kinetically allowed, versus other sequences; i.e. transitions between secondary structures occur frequently, implying relatively low activation barriers. Visual inspection of trajectories shows a sharp structural reorganization early on (<100 ns) in most of the simulations.

Figure 4A:
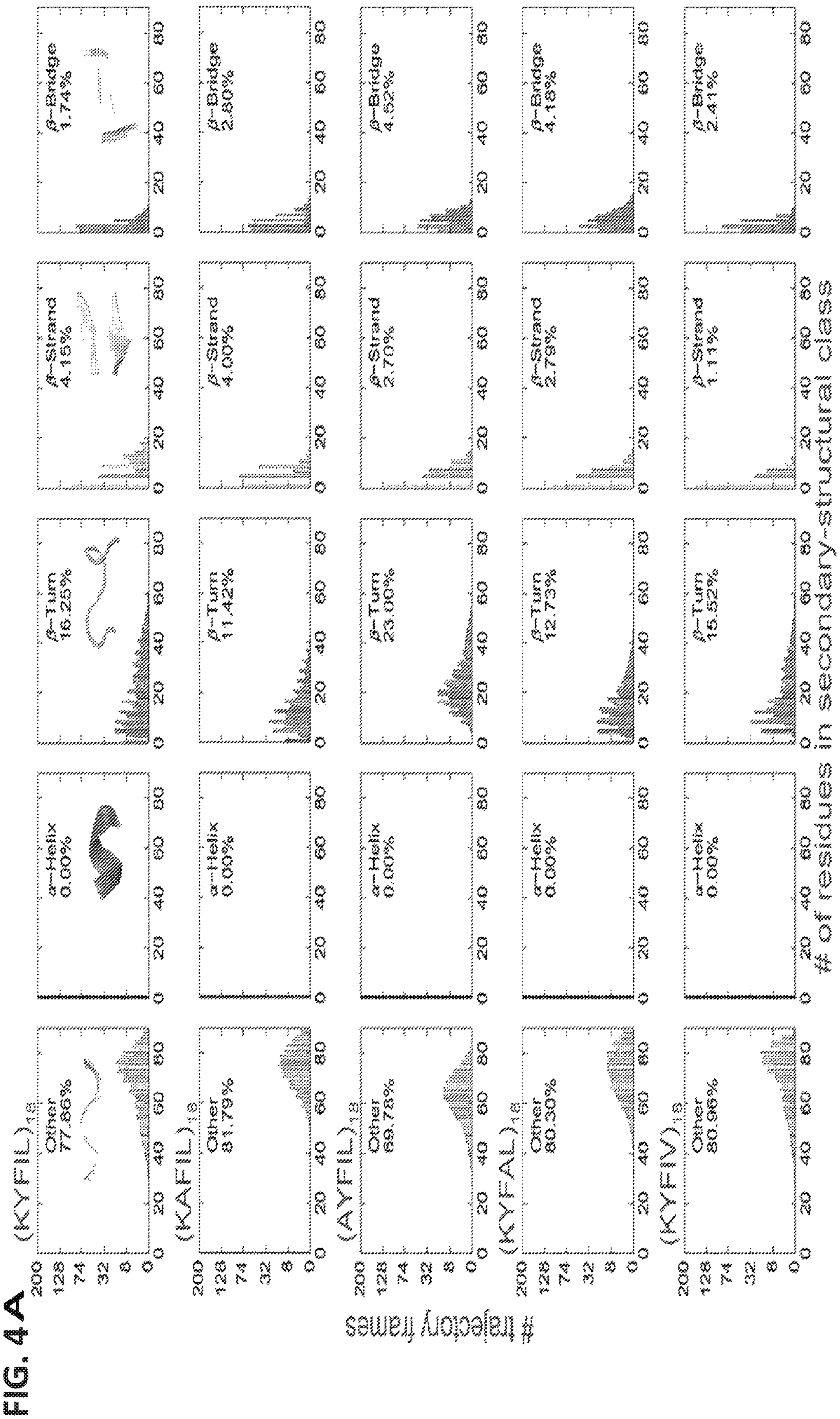
FIGS. 4A-B depicts the secondary structural content of the simulated KYFIL, KAFIL, AYFIL, KYFAL, and KYFIV systems. Numbers within a plot represent the population of the secondary structure observed in the simulation over all possible secondary structure conformations. Secondary structure cartoon representations in the thumbnails displayed in the first row match the colors in the histogram.
Figure 4B:
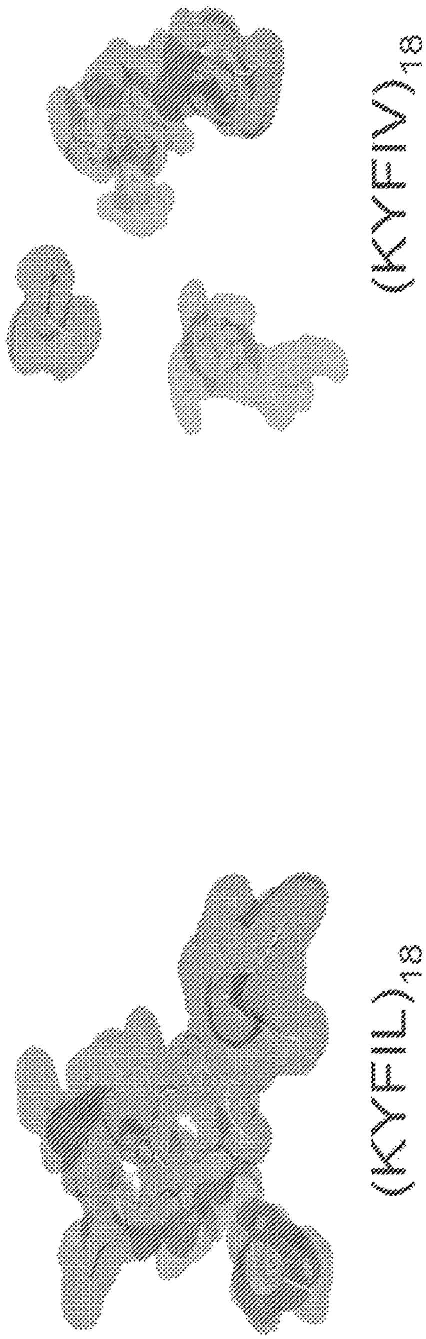
Figure 13A:
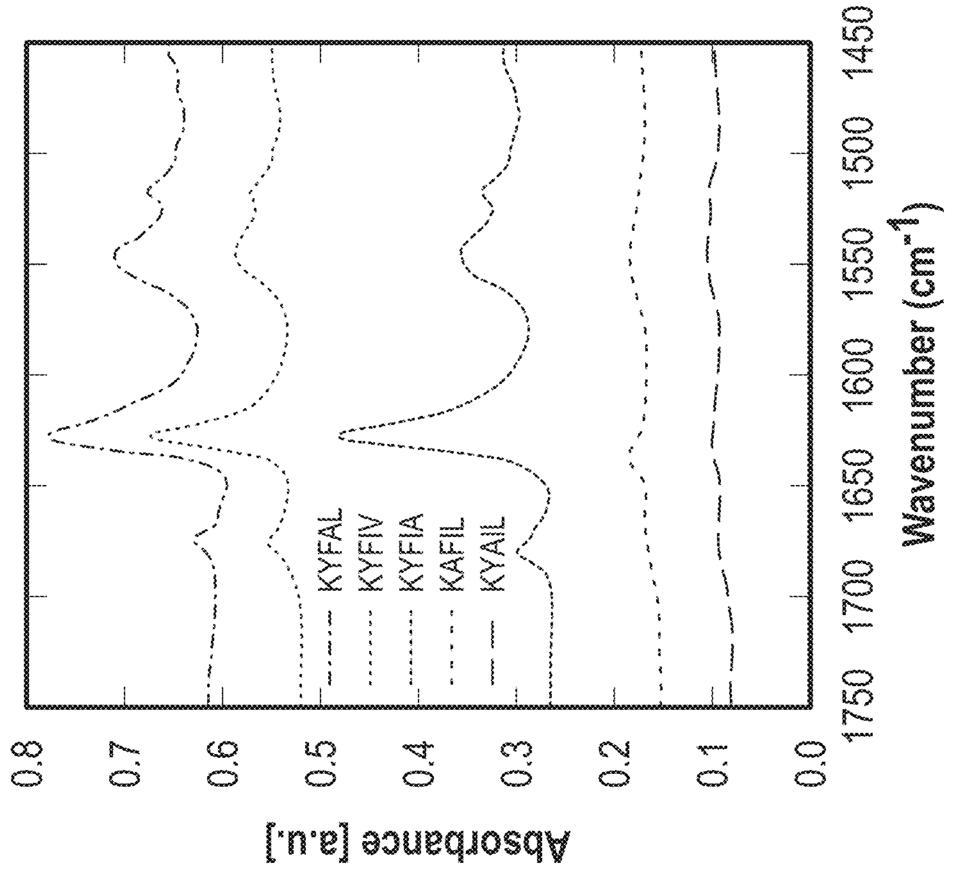
FIGS. 13A-B show ATR-FTIR spectrum of the instantly-disclosed peptides.
Figure 13B:
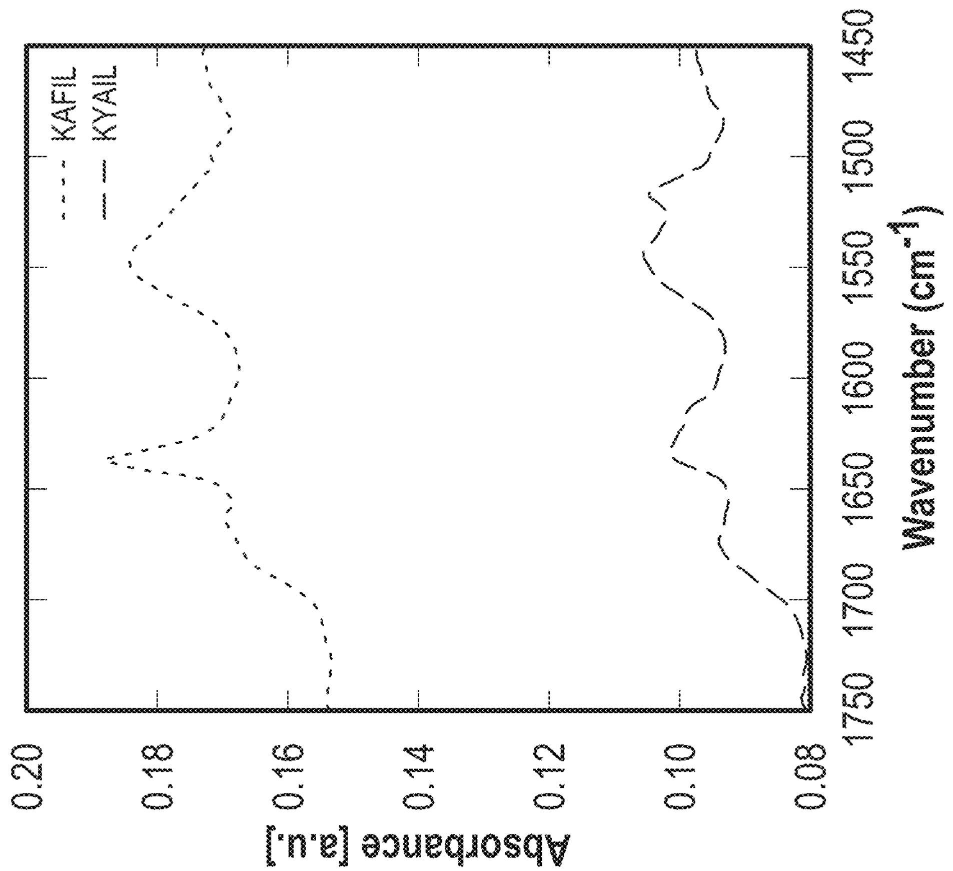

We also examined the structural transitions from the initial peptide system (postequilibration) to the final conformational ensemble. For all simulated peptide sequences, there was a notable dearth of α-helicity (FIG. 4A), consistent with the experimental FTIR data (FIG. 2 and FIGS. 13A-B). All pentapeptides preferentially sampled β-type structures (FIG. 4A), and the gelling peptide sequences (KYFIL, AYFIL, KYFAL, and KAFIL) exhibited a nominally greater fraction of β-strand character over the course of the 200 ns trajectory, versus a nongelling sequence, KYFIV (FIG. 4B). The domain swapping mode of β-rich association can be induced by intermolecular β ••• β-strand/bridge contacts, via directional hydrogen bonding between the backbones of aromatic residues and β-branched amino acids (e.g., isoleucine). Consequently, the structural rearrangement of peptides can reduce conformational strain, as the formation of such β-strand structures are enthalpically favorable, driving the folding of β-sheets. The torsion angles for each type of amino acid, barring the N- and C-termini (FIGS. 15A-E), indicate significant structural heterogeneity for each peptide system. These results suggest that, in general, the middle Phe in each pentapeptide often adopts a type-II β-turn conformation (φ=−60°, ϕ=120° or an antiparallel β-sheet structure (φ=−140°, ϕ=135°; this is consistent with our aforementioned FTIR results. For the KYFAL and KAFIL sequences, the Ala preferentially samples a polyproline type-II helix (φ=−75°, ϕ=145°), with a decreased β-sheet propensity. This result is unsurprising, as the peptide backbone near an Ala (versus Tyr) residue encounters less steric hindrance, given the absence of the phenol side-chain. The most densely populated regions of conformational space for Ile, in all pentapeptide sequences (FIGS. 15A-E), highlights this amino acid's propensity to adopt β-sheet conformations. In this context, Phe ••• Ile intermolecular interactions (steric occlusion, as well as London dispersion forces and other van der Waals forces) are particularly relevant, as they would facilitate the hydrophobic aggregation of these peptide regions and indirectly enable the formation of hydrogen-bond networks between the local backbones; this model is also consistent with both MD simulations and FTIR spectroscopic data (FIG. 2).

In addition to internal (intrapeptide) and external (interpeptide) interactions, the conformational dynamics of a peptide system are governed by peptide ••• solvent interactions. By quantifying peptide ••• water contacts, one can discern hydrophobic side-chain contributions to the energetics of peptide assembly and also study a peptide's solvation dynamics. Thus, the solvent-accessible surface area (SASA) of individual residues in each pentapeptide were evaluated, averaged over entire 200 ns trajectories. In computing the relative SASA of a peptide system (via Rost and Sander's method, Rost, B.; Sander, C. Conservation and Prediction of Solvent Accessibility in Protein Families. Proteins: Struct., Funct., Genet. 1994, 20 (3), 216-226, herein incorporated by reference in its entirety), we consider the ordinary accessibility of a residue in a structure normalized by the maximal value possible for that residue type (i.e., that amino acid side-chain). Unsurprisingly, for each pentapeptide sequence the N-terminal Lys was the most solvent-exposed (FIG. 5) and the central tripeptide (••• Tyr/Ala-Phe-Ile/Ala •••) was the most consistently buried throughout the simulation. The significant changes in relative accessibility of the C-terminal residue (position 5) indicate the system's structural rearrangement in the context of side-chain functional groups. Our findings are consistent with patterns in Kyte-Doolittle hydropathicities (GRAVY values in FIG. 5) as well as prior experimental results regarding the hydration structure of ABA triblock copolymeric systems, wherein the termini were found to be exposed to aqueous solvent molecules and dehydration of nonpolar side-chains biases the middle block of the amphiphilic pentapeptide to preferentially adopt compact 3-D structures (β-strands, turns, etc.) that occlude solvent.

Hierarchical Self-Assembly: Evaluating Hydrogel Rheological Properties

Figure 6B:
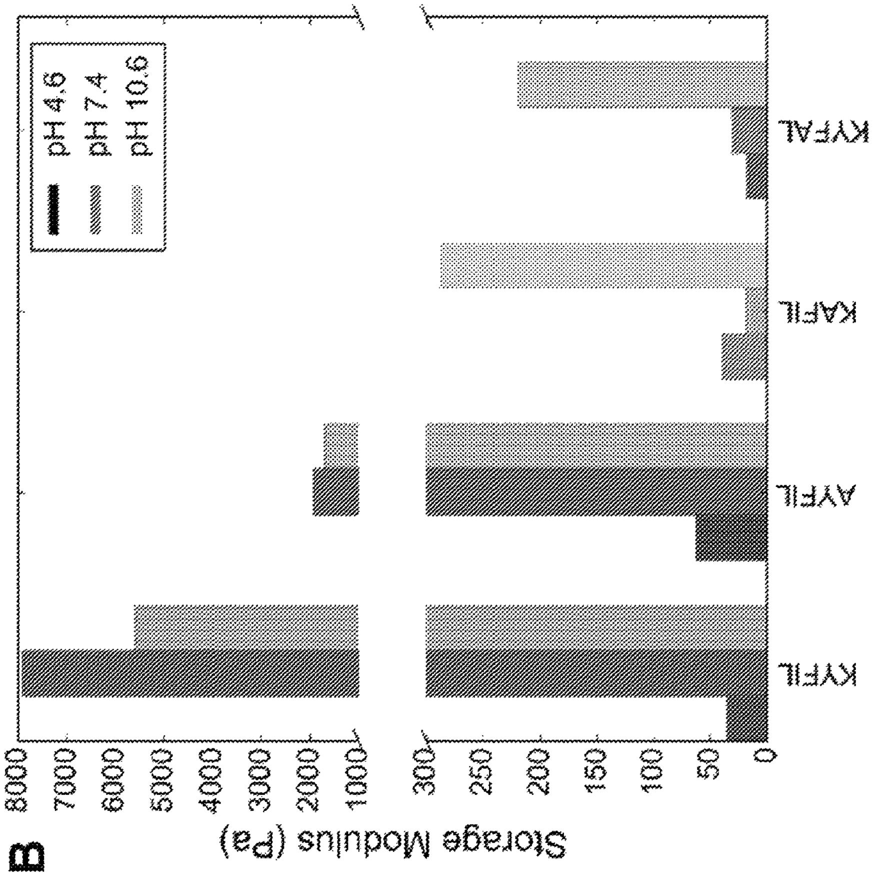
FIGS. 6A-D depict rheological properties of self-assembling pentapeptides at different concentrations and pH conditions.
Figure 6A:
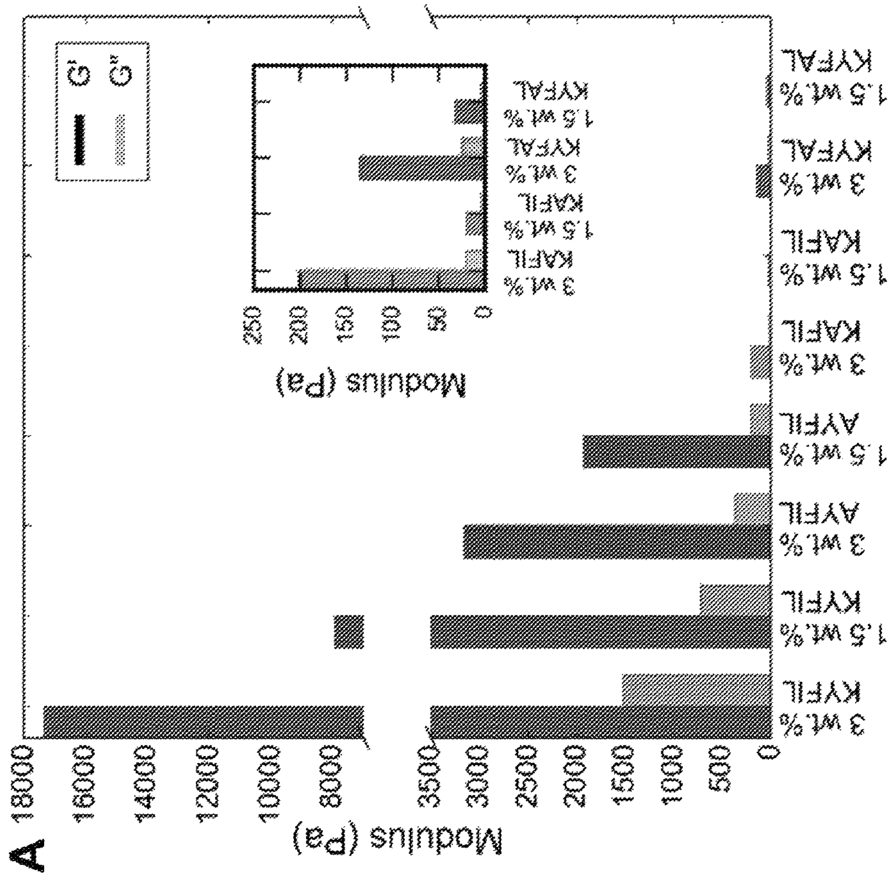
Figure 6:
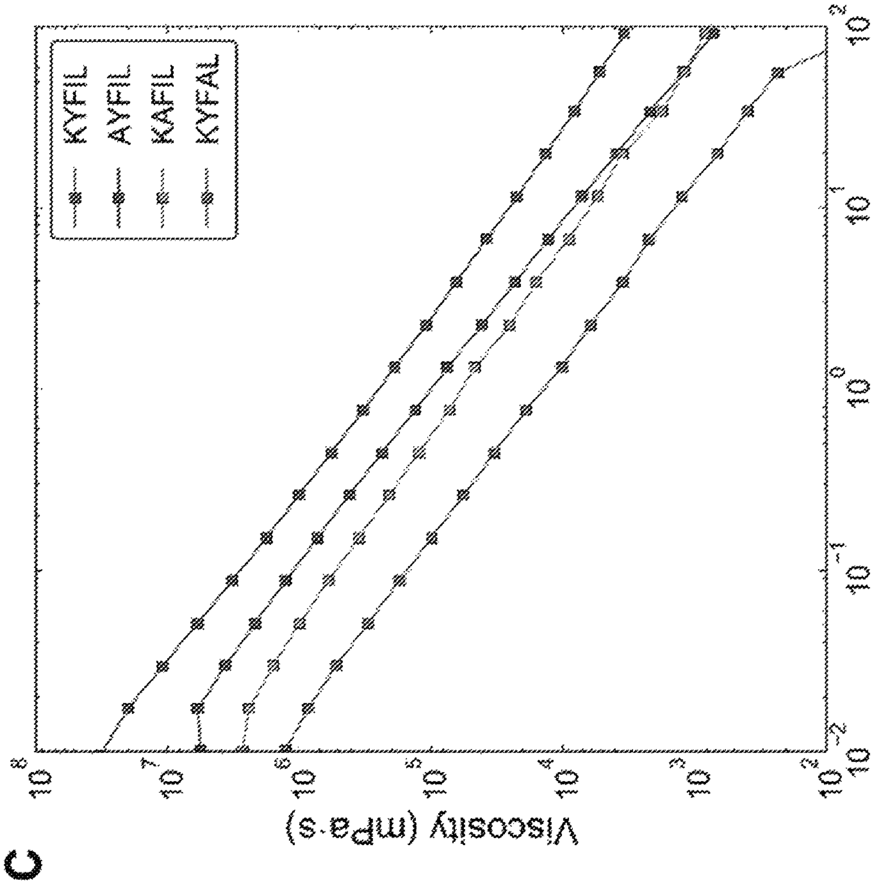
Figure 6:
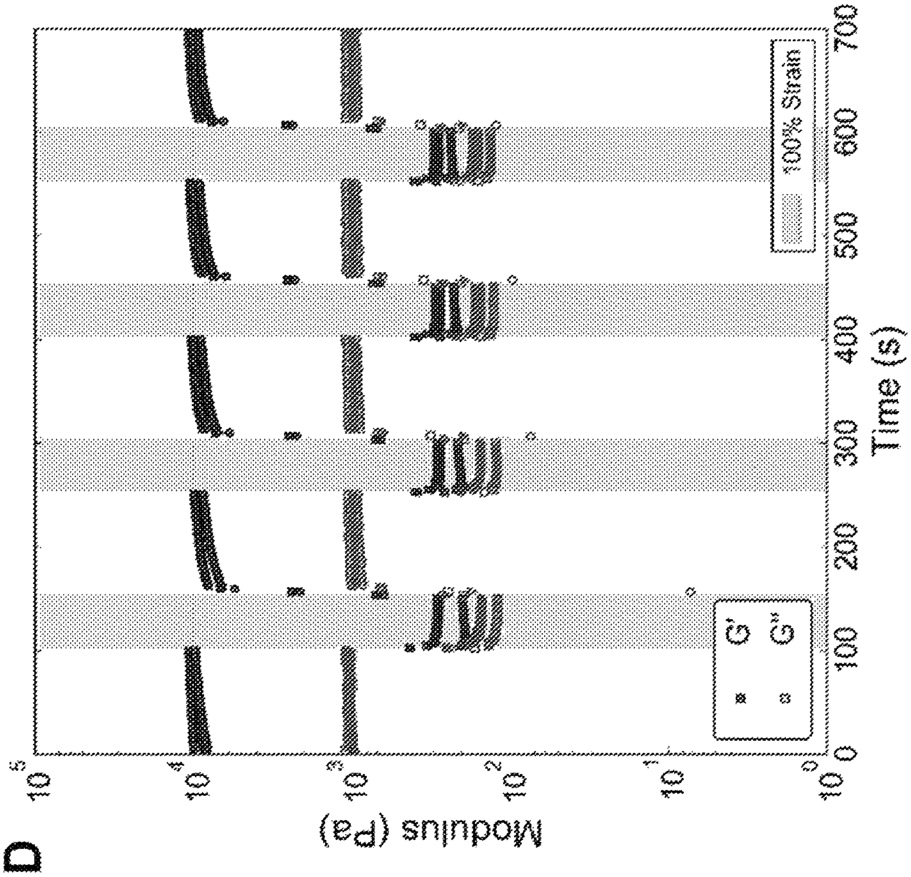

The mechanical properties of 1.5 and 3 wt % hydrogels were found to depend on the concentration, pH, and peptide sequence. Hydrogels formed in situ, in an epitube, within several seconds (data not shown) and were then pipetted onto the rheometer platform for rheological measurements. RAPID hydrogel stiffness's span 2 orders of magnitude, from approximately 50-17000 Pa in shear storage moduli (G') (FIG. 6A). For comparison, this would be similar to 520-44200 Young's modulus, although this requires a potentially fraught assumption of a Poisson's ratio of 0.5. KYFIL at 1.5 and 3 wt % forms hydrogels of 8000 and 17000 Pa, respectively (FIGS. 6A-D and FIGS. 16A-B).

Peptide hydrogels can provide structural flexibility and mechanical properties that emulate native biological tissues. Bulk matrix stiffness and topography are well known biomechanical cues that can direct stem cell proliferation as well as differentiation. In most tissues, such as the heart, muscle, and bone, the extracellular matrix contributes to the biophysical microenvironment, e.g. a Young's modulus of 6.8 kPa for heart tissue and up to 103 kPa for bone. However, tissues within the central nervous system (CNS), such as the brain and spinal cord, are some of the most compliant tissues in the body, with moduli of ~0.7 to 3.5 kPa. Such an extensive range of stiffness requires hydrogel biomaterials to have highly tunable biomechanical properties that can be catered to a wide range of applications, for numerous different tissue types throughout the body.

Our class of peptide sequences is unique in that the peptide lengths are quite short (5 amino-acid residues) and have a broad range of mechanical properties (~50-17000 Pa) that can be fine-tuned via small changes in concentration or pH (FIGS. 6A-D). The broad range and large magnitude of storage moduli we can attain is in contrast to other short, self-assembling oligopeptides. For example, $K_2(QL)_6K_2$, RADA16-I, $(FKFE)_2$, MAX1/8, and KLVFF sequences yield gels with much lower storage moduli and narrower ranges of mechanical properties (storage moduli of 50-1000 Pa). The lower storage modulus of KYFAL can be reconciled with its weaker signature peak intensities for β-sheets in the FTIR spectra (FIG. 2), implying less content of well-ordered β-sheet for KYFAL (FIGS. 4A-B). Additionally, Lys did not seem to affect gelation, so long as the amphiphilicity of the sequence was maintained. Rather, the substitution of Lys→Ala affected the solubility of the peptide (FIGS. 18A-D). Similarly, at 3 wt %, KAFIL had a G' of 200 Pa compared to KYFAL at 133 Pa. The additional bulky methyl group in the Ile-Leu C-terminus of KAFIL, relative to Ala-Leu (in KYFAL) or Ile-Ala and Ile-Val (in KYFIA and KYFIV, respectively) confers greater hydrophobicity, resulting in a self-assembly process driven mainly by increased hydrophobic interactions.

The apparent pKa shift following the substitution of Tyr to Ala increases the electrostatic repulsion between peptides, reducing the aggregation propensity. Increasing the pH, which alters the average degree of ionization, better neutralizes KAFIL and favors self-assembly of the peptide, by reducing the mean net charge of the Lys headgroup. Our rheological characterization of hydrogel-forming peptides indicates that Ile facilitates self-assembly: we detect a higher population of β-sheet conformations for Phe-Ile-Leu versus Phe-Ala-Leu sequences.

In investigating the pH responsiveness of hydrogel-forming sequences, we found that all peptides exhibited lower storage moduli upon a decrease in pH. The three pHs were chosen (4.6, 7.4 and 10.6) to include the physiological pH of 7.4—particularly relevant for viable cell encapsulation—as well as acidic and basic pHs that bracket the pI of each sequence (FIG. 1A). The G' increases by several orders of magnitude as the pH of the solution increases toward neutrality (FIG. 6B). Nongelling sequences (KYFIV, KYFIA, KYAIL) also exhibit pH-responsive behavior: at low pH, the peptides were soluble, but precipitated as an off-white powder as the pH was raised (but never gelled). The storage (G') and loss (G") moduli of 1.5 and 3 wt % hydrogels increased with increasing concentrations of the hydrogel and increasing pH conditions (FIGS. 6A-B, FIGS. 17A-D, FIGS. 18A-D, and FIGS. 30A-B).

Figure 21:
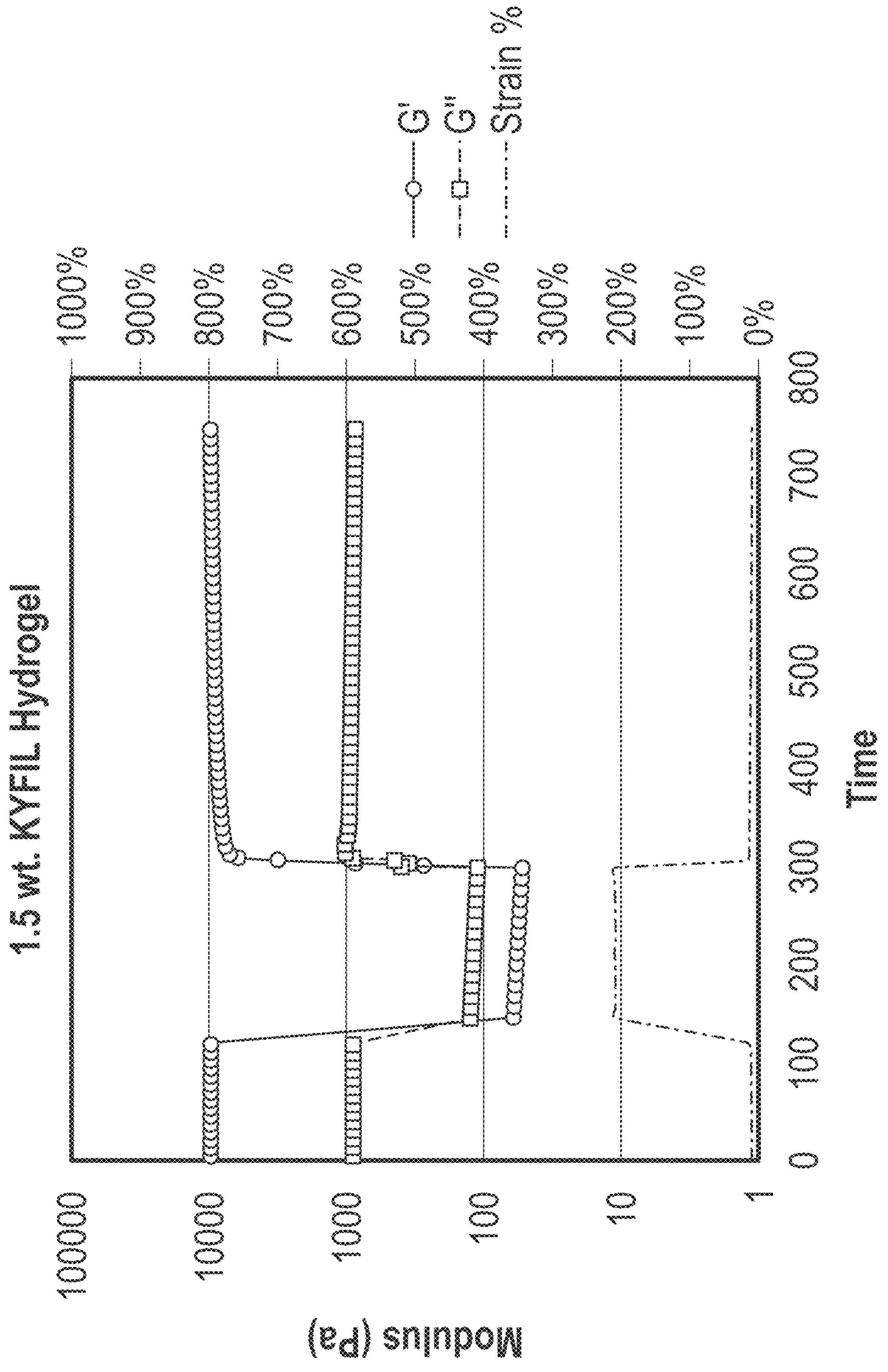
FIG. 21 depicts the results of a thixotropy test performed for 1.5 wt. % KYFIL hydrogels. A strain sweep of 0.1% (100 s) followed by a 200% strain (200 s), followed by a 400 s recovery period. The hydrogel is able to recover 90% of its initial G' in 3.5 minutes, and 7 minutes to recover 96%.

The apparent viscosity of all gelling sequences decreased linearly with increasing shear rate, demonstrating the shear thinning capacity of these hydrogels (FIG. 6C, FIGS. 20A-D, and FIGS. 30C-D). Multiple high-strain (100%) sweep cycles, with 30 s recovery periods, demonstrated KYFIL's ability to self-heal following mechanical deformation, without any evidence of hysteresis (FIG. 6D and FIG. 21). Following 100% strain, hydrogels repeatedly recovered gel behavior within 14 s (G'>G"). Within 1 min, the gel recovered 82% of its initial G' and required 3.4 min to recover 90% and 7 min to recover 96% (FIG. 21). Even after multiple high-strain cycles, the hydrogel rapidly and repeatedly recovers its mechanical strength-rendering these materials particularly ideal for biomedical applications that require injection. This enables uniform encapsulation of cells in 3-D, ex vivo, and then injection via a minimally invasive technique. Similarly, we found that the hydrogels could regel, macroscopically, following a syringe ejection (data not shown), suggesting that materials based upon these peptides could be well-suited to additive manufacturing applications like extrusion-based 3-D printing.

The propensity of our RAPID peptides to adopt β-rich structures, alongside their capacity to form hydrogels (and the presence of fibrillar networks in such gels [see below]), bears a striking resemblance to the phenomenon of liquid phase condensation as a means to form P-bodies, stress granules, and other types of intracellular protein gels or "membrane-less organelles". In such liquid-liquid phase separated systems, a multivalent web of relatively weak (individually) molecular interactions leads to the mesoscopic assembly of a distinct, de-mixed liquid phase (e.g., the nucleolus) within the cell. Notably, these molecular interactions generally occur between low-complexity, conformationally pliable peptides, as in the recently characterized, hydrogel-forming "low-complexity aromatic-rich kinked segments (LARKS)" (Hughes, M. P. et al. Atomic structures of low-complexity protein segments reveal kinked beta sheets that assemble networks. Science 2018, 359 (6376), 698-701, herein incorporated by reference in its entirety). A possible direction for future work involves elucidating any similarities between the "aromatic ladders" and other structural features of LARKS assemblies and, for instance, the conserved Phe in our RAPID peptide systems.

Electron Microscopy of Nanofiber Morphology: TEM and CryoEM

Figure 7A:
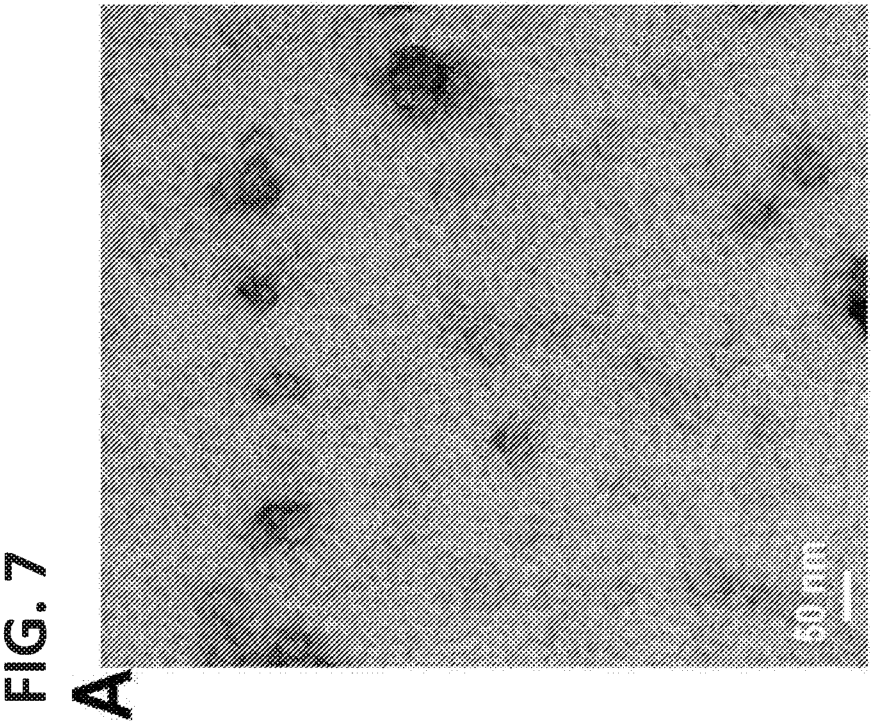
FIGS. 7A-F are representative EM images of 1.5 wt % KYFIL hydrogels.
Figure 7B:
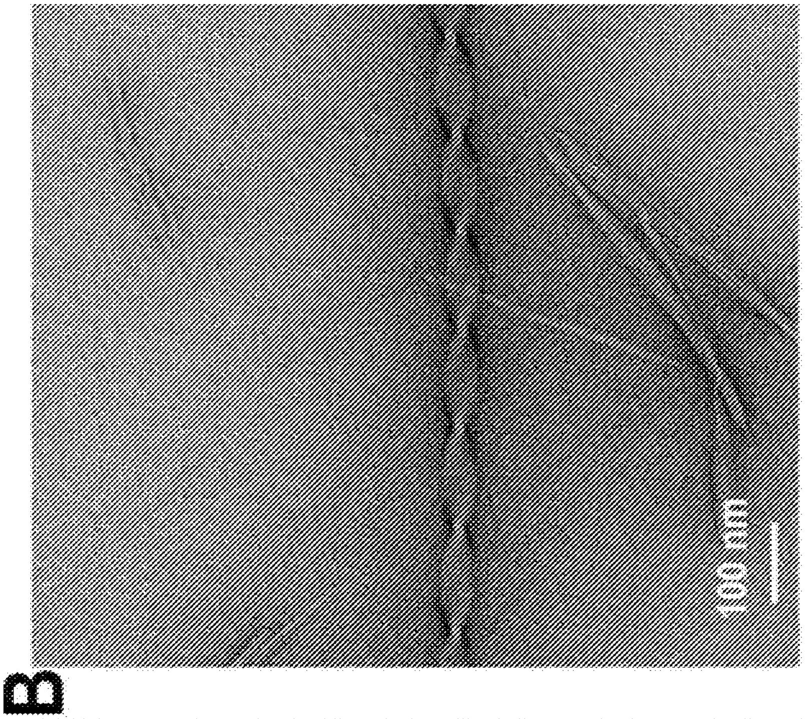

Fibrils, tubes, dendrimers, and other ultra structures often form via a hierarchical supramolecular arrangement of specific, noncovalent contacts. TEM analysis revealed that our RAPID hydrogels are composed of nanofibers as well as dense regions of fibrous bundles. At low pH (i.e., nongelling conditions), fibers do not form within the peptide solution; rather, amorphous aggregates are present (FIG. 7A). At physiological pH, individual fibers bundle into hierarchical nanostructures with clearly twisted, ribbon-like morphologies (FIG. 7B). The multistranded, twisted ribbons reported here are unique among nanofiber-forming, self-assembling peptide hydrogels. In at least some characterized systems, the helicity (and other geometric properties) of fibers are thought to depend on such atomic-level effects as the properties of steric packing between aromatic side-chains, such as for Tyr and Phe; whether the general morphological properties that we find for RAPID peptides can be traced to such underlying factors is an appealing question for future structural modeling studies. In earlier work, cooperative intermolecular hydrogen-bonding between the backbone N and C-termini were found (by modeling) to enable stronger interactions (i.e., closer intermolecular packing), leading to the classical geometric features of twisted ribbons. The instantly disclosed peptides in aspects are C-terminally amidated, and it is more likely that RAPID fibrils assemble via antiparallel stacking of pentapeptides, with details of the molecular packing predominantly stemming from apolar dispersion forces and other enthalpically favorable interactions among the Phe moiety and amphiphilic nature of the sequence.

Figure 7C:
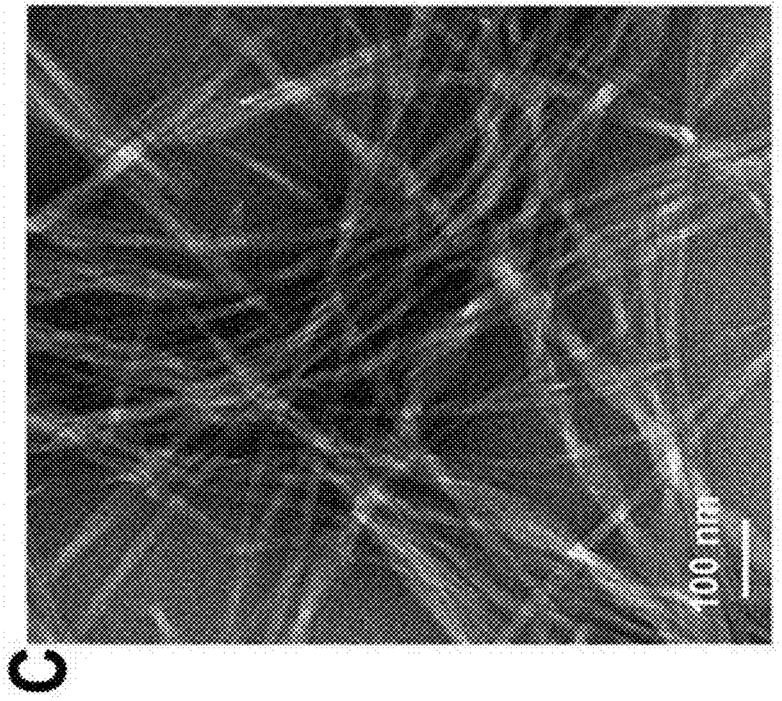

Individual fibers can apparently entangle, yielding multi-stranded twisted ribbons (FIG. 7C). Similar hierarchical "bundling" of fibrils, interwound "superhelices", and other higher-order assemblies have been seen in systems such as amyloid-related peptides. In other previously characterized self-assembling peptide systems, ionic interactions, modulation by the solvent environment, and hydrogen bonds are thought to govern the formation of interconnected networks of nanofibrils. In addition, and unlike other nanofiber-forming peptides, the pentapeptide sequences presented here are significantly shorter than many hitherto characterized systems (decapeptides and beyond). Furthermore, other self-assembling peptide hydrogels often lack distinct morphology within their nanofiber-forming sequences (instead being irregular and heterogeneous), whereas RAPID peptides form highly regular, twisted fibril nanostructures.

Figure 7D:
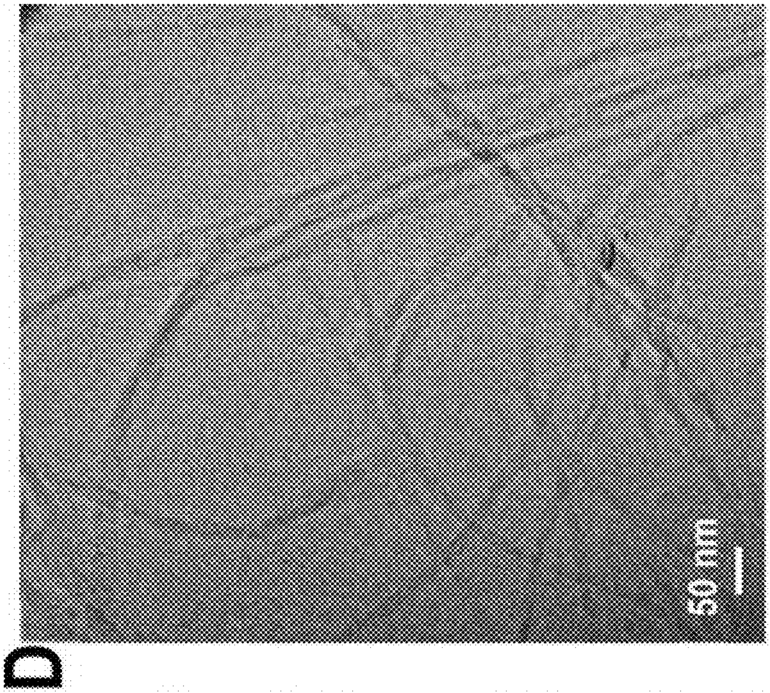
Figure 7:
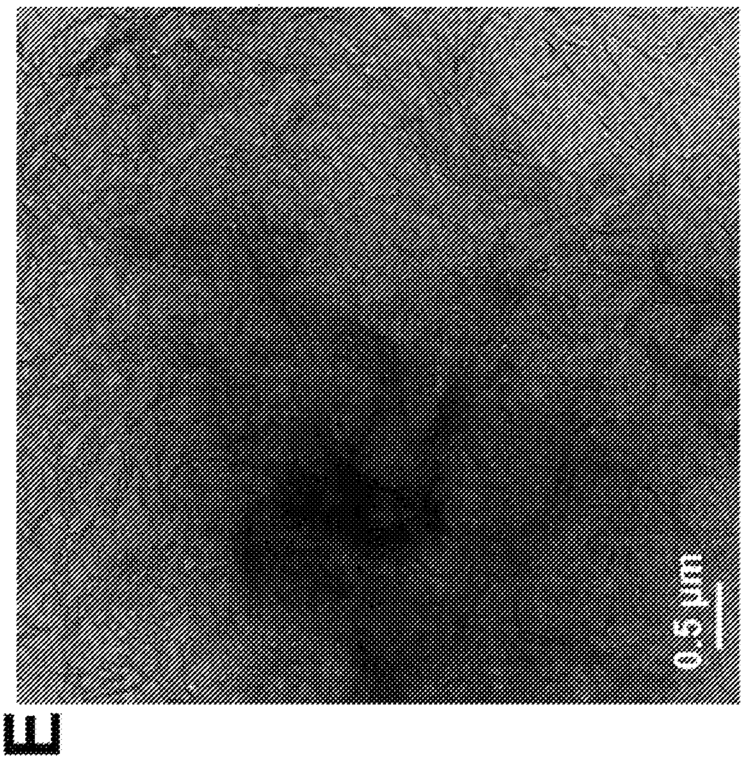
Figure 7:
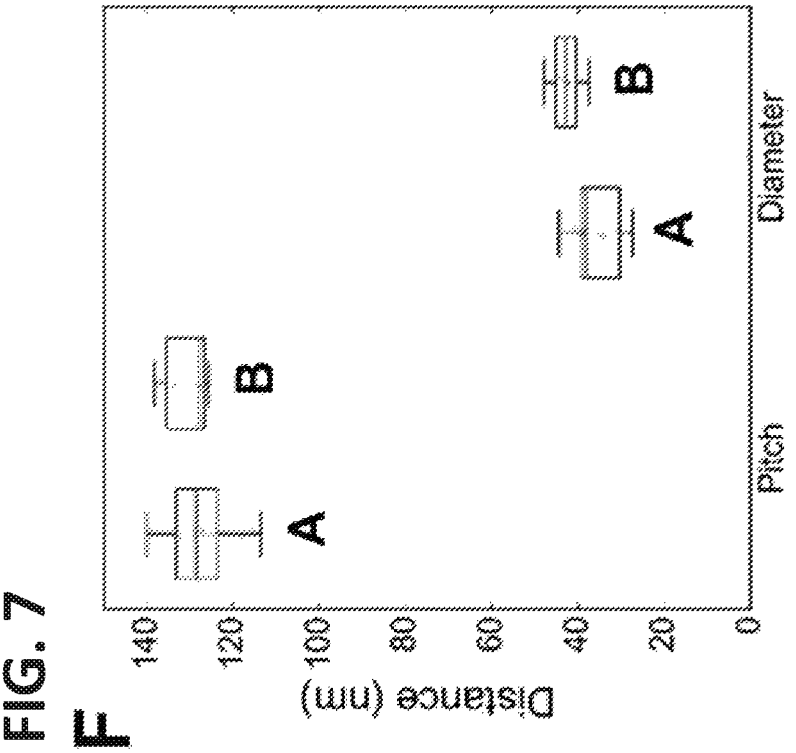
Figure 22:
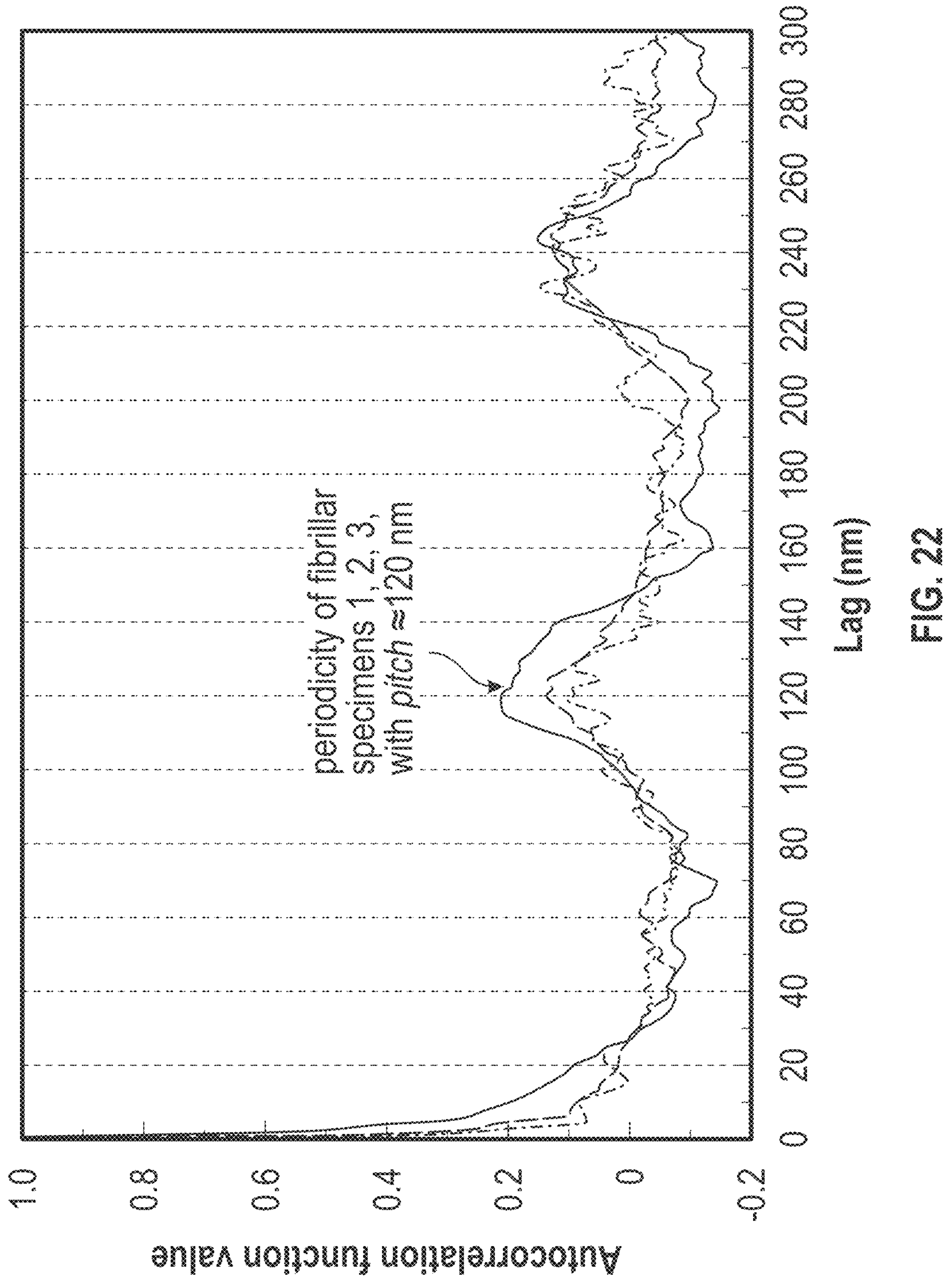
FIG. 22 depicts the periodicity of the fibrillar twist, as quantified by the intensity autocorrelation function (ACF). The ACF was computed for the height intensity of fibrils found in micrograph images of three independent TEM specimens (red, green and
blue traces); the fundamental frequency can be seen to correspond to a distance (lag) of ≈120 nm.
Figure 23:
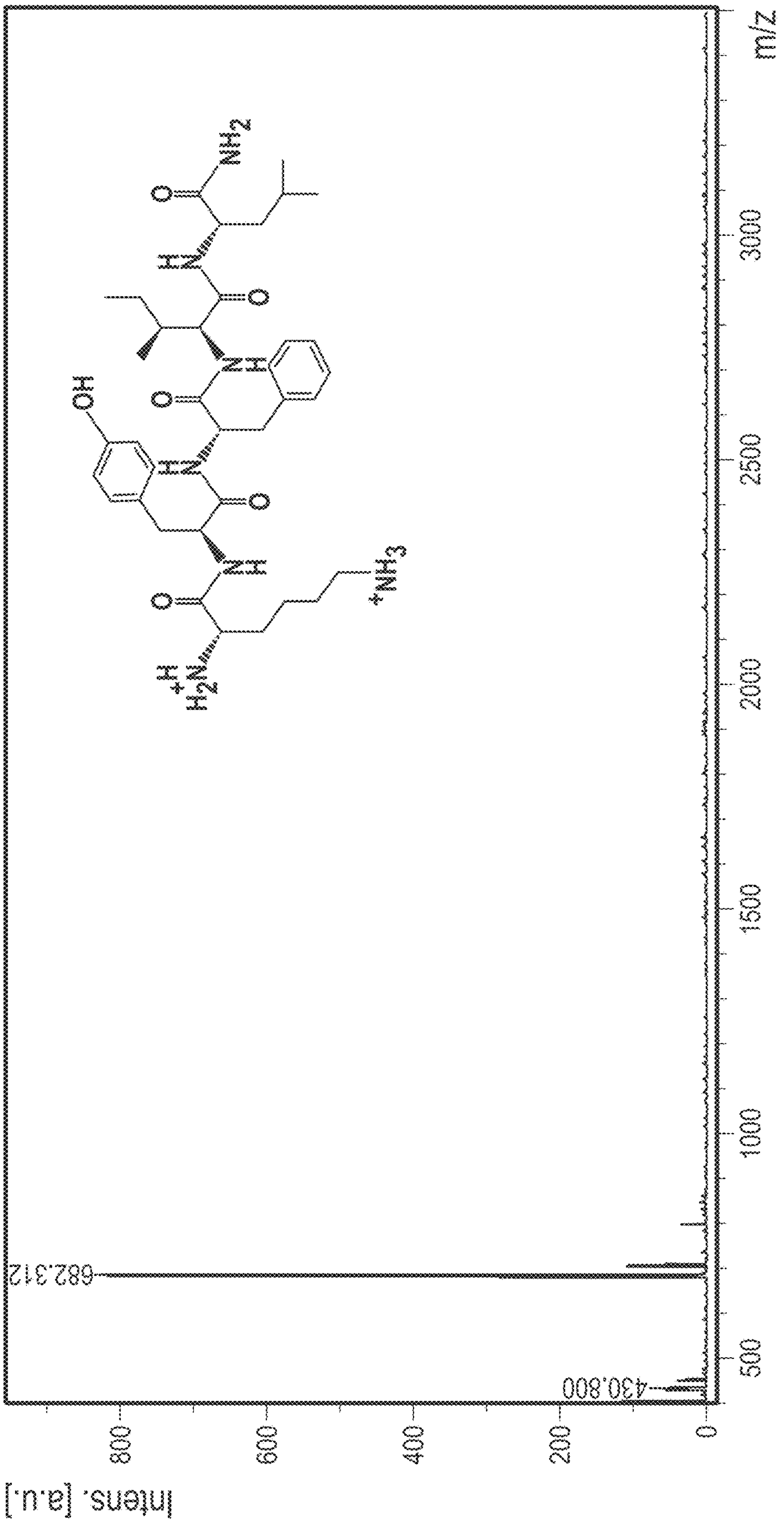
FIG. 23 depicts the MALDI-TOF MS of KYFIL peptide, with an expected mass [M+H+]+=682.87, and an observed mass=682.312.
Figure 24:
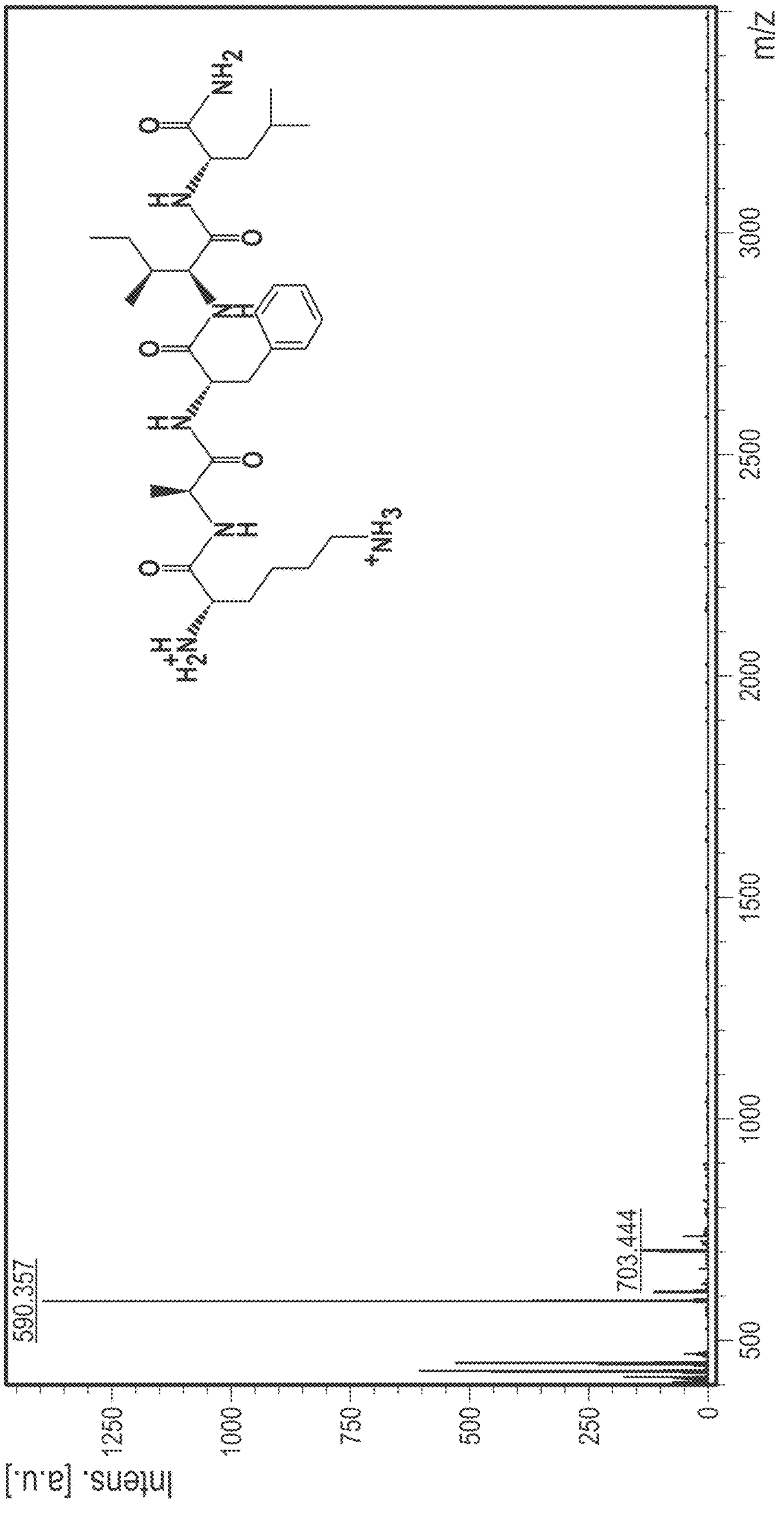
FIG. 24 depicts the MALDI-TOF MS of KAFIL peptide, with an expected mass [M+H+]+=589.77, and an observed mass=590.357.
Figure 25:
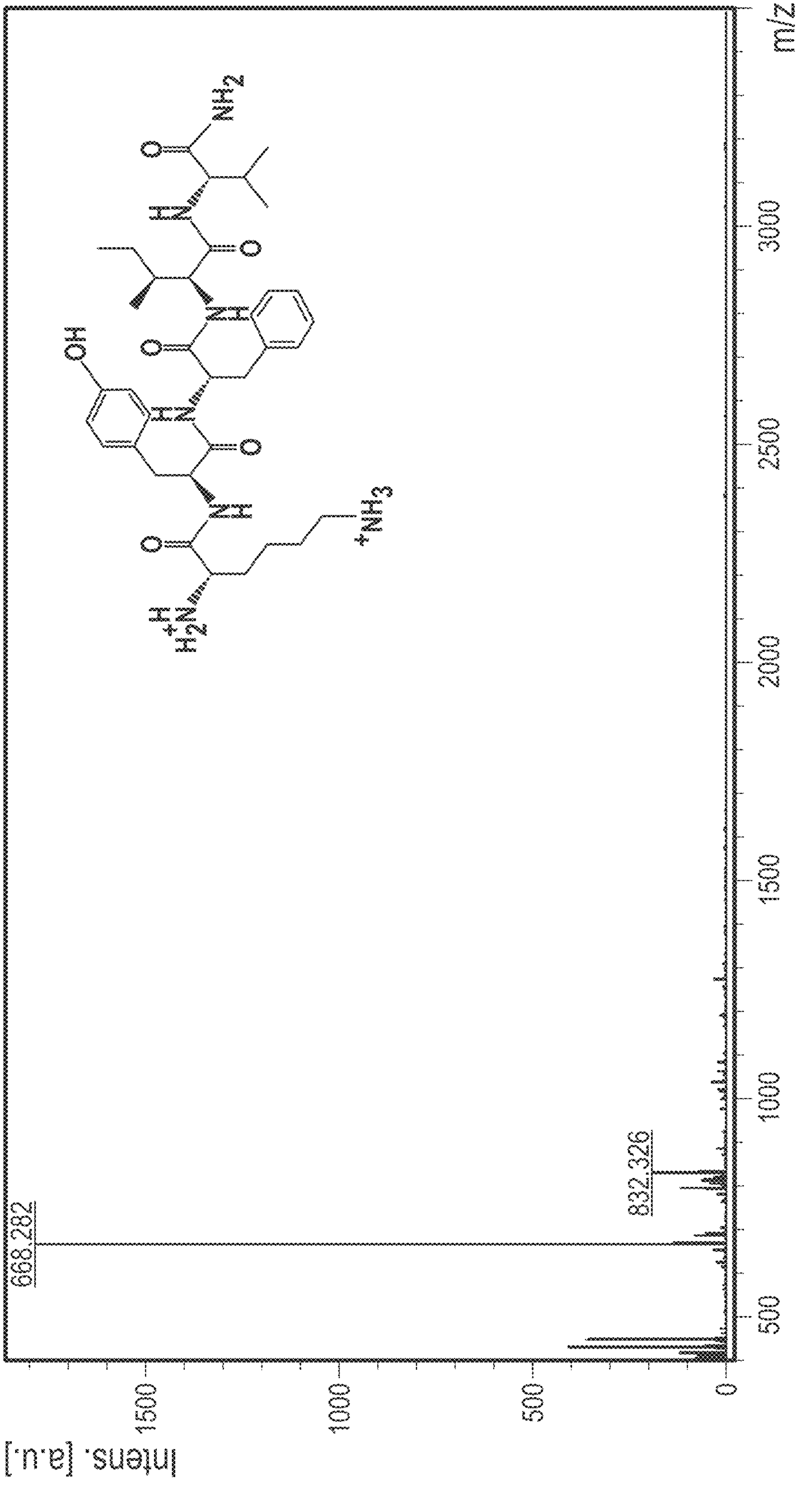
FIG. 25 depicts the MALDI-TOF MS of KYFIV peptide, with an expected mass [M+H+]+=667.84, and an observed mass=668.282.
Figure 26:
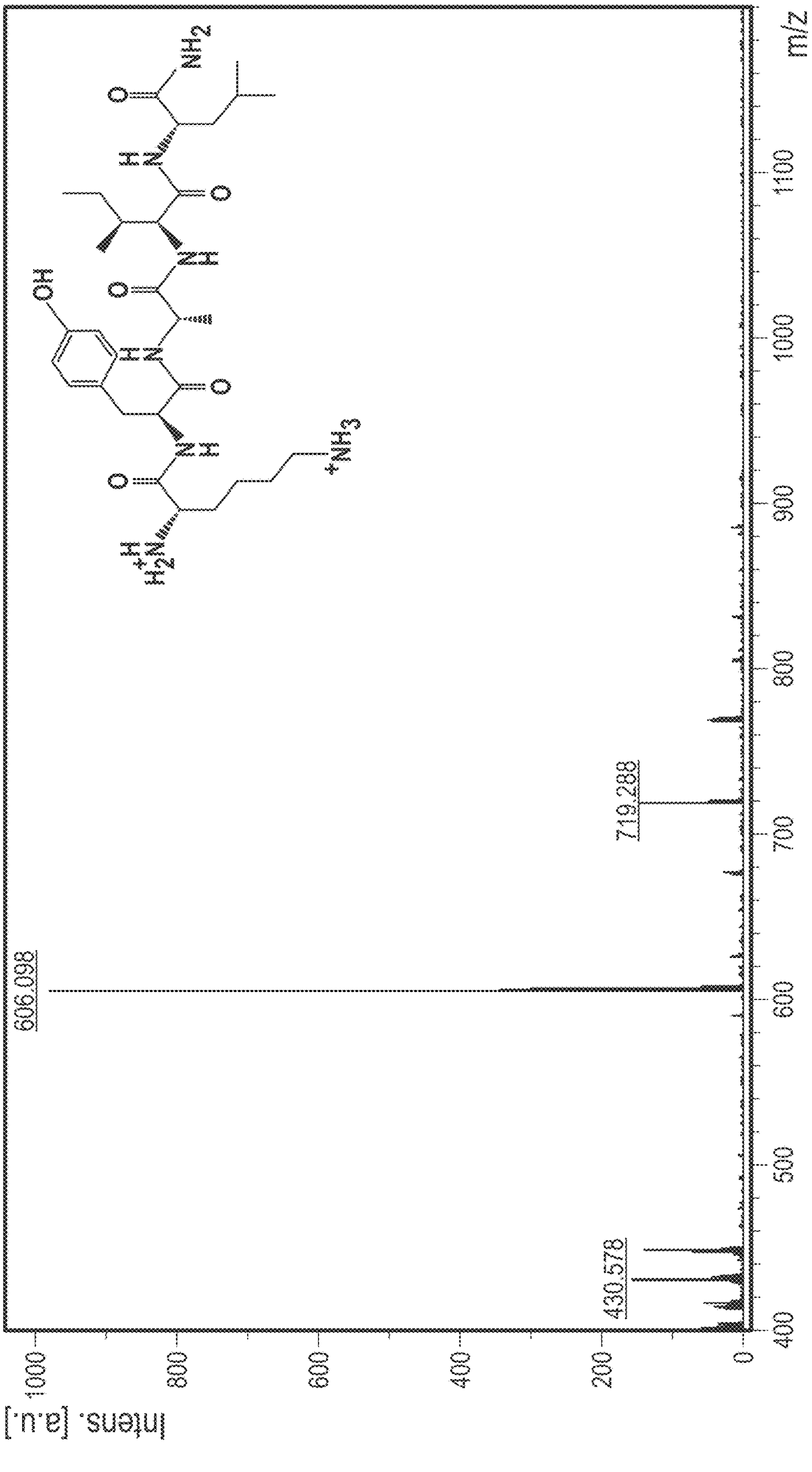
FIG. 26 depicts the MALDI-TOF MS of KYAIL peptide, with an expected mass [M+H+]+=605.77, and an observed mass=606.098.
Figure 27:
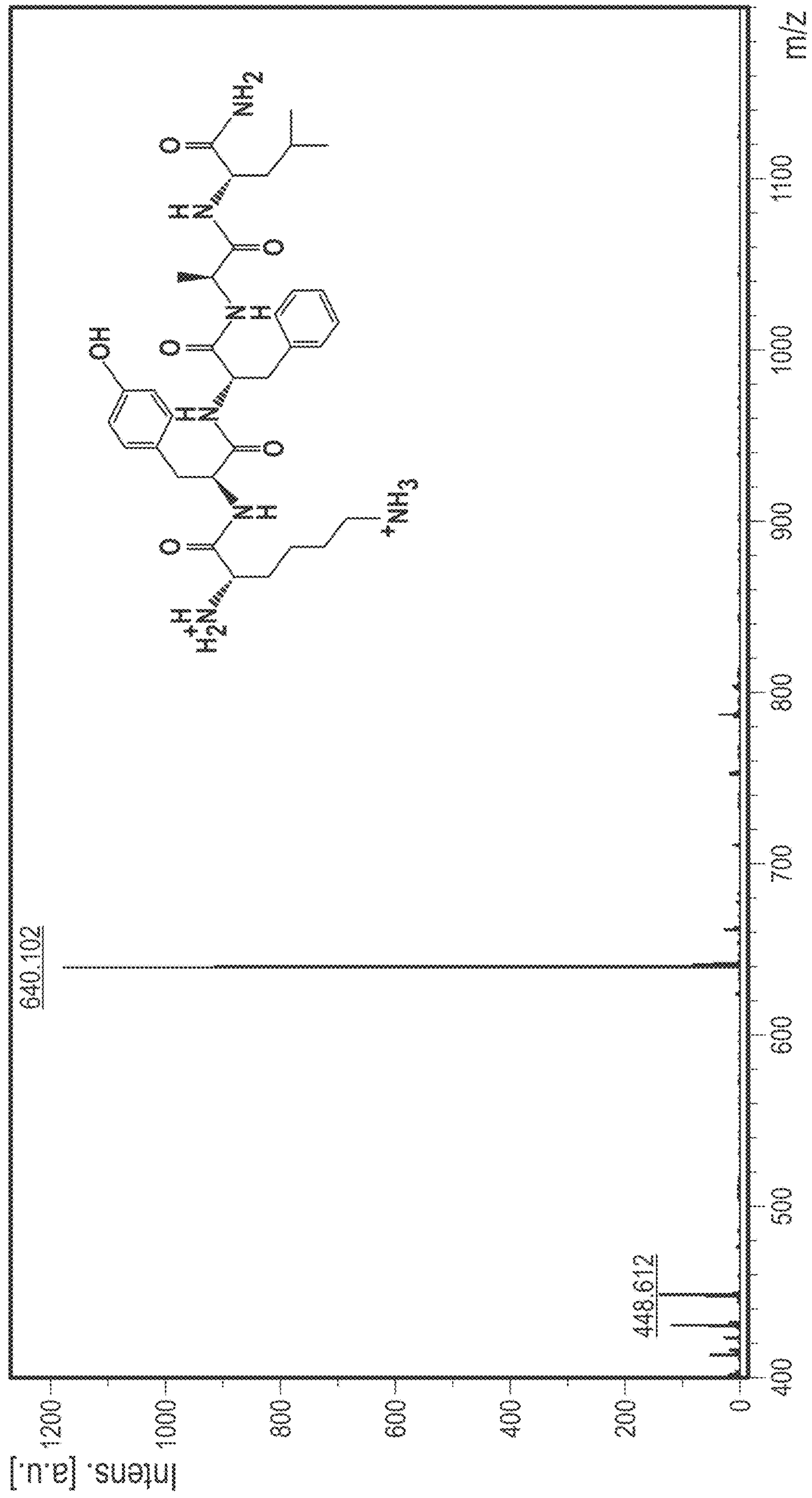
FIG. 27 depicts the MALDI-TOF MS of KYFAL peptide, with an expected mass [M+H+]+=639.79, and an observed mass=640.102.
Figure 28:
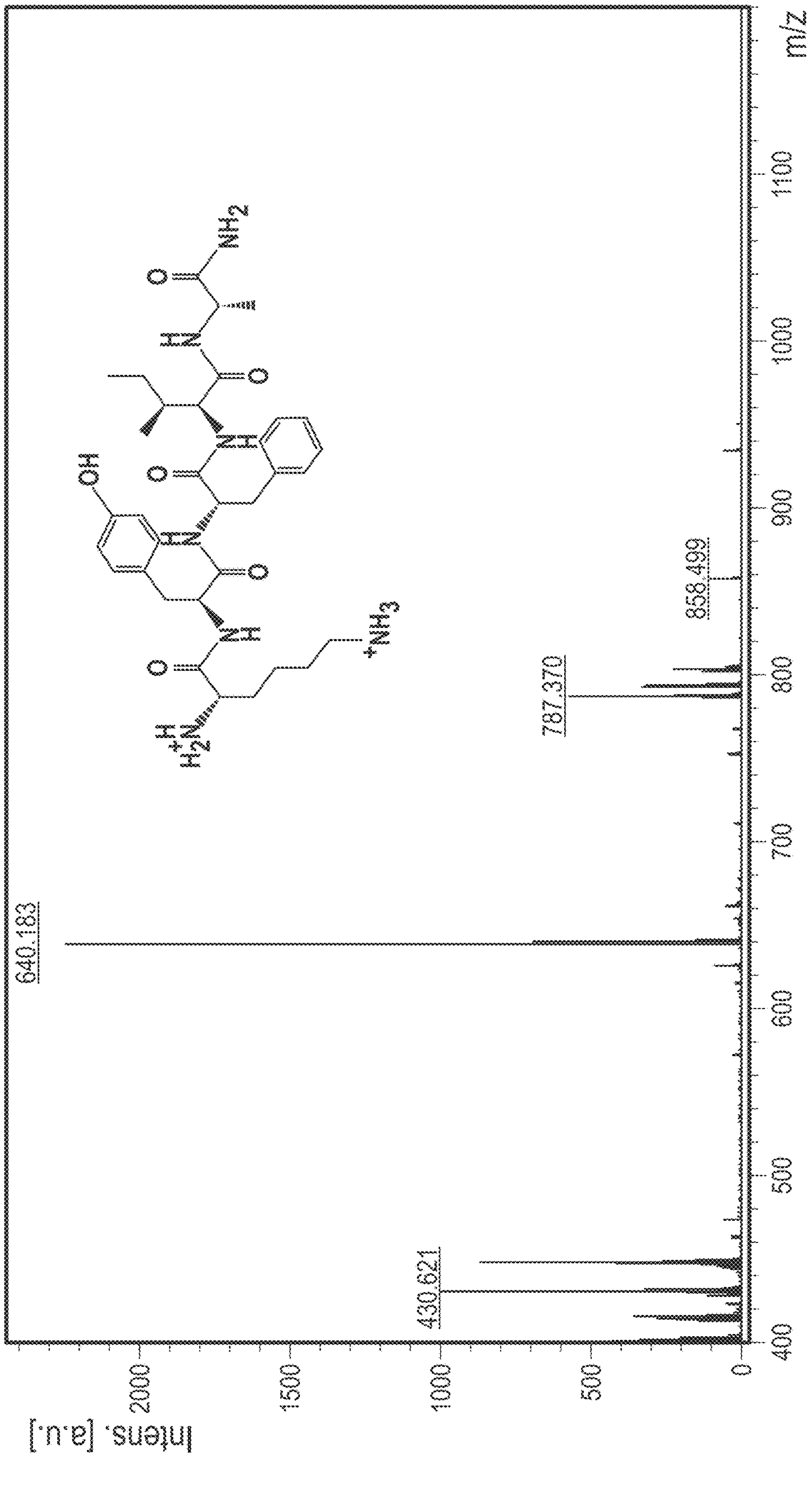
FIG. 28 depicts the MALDI-TOF MS of KYFIA peptide, with an expected mass [M+H+]+=639.79, and an observed mass=640.183.
Figure 29:
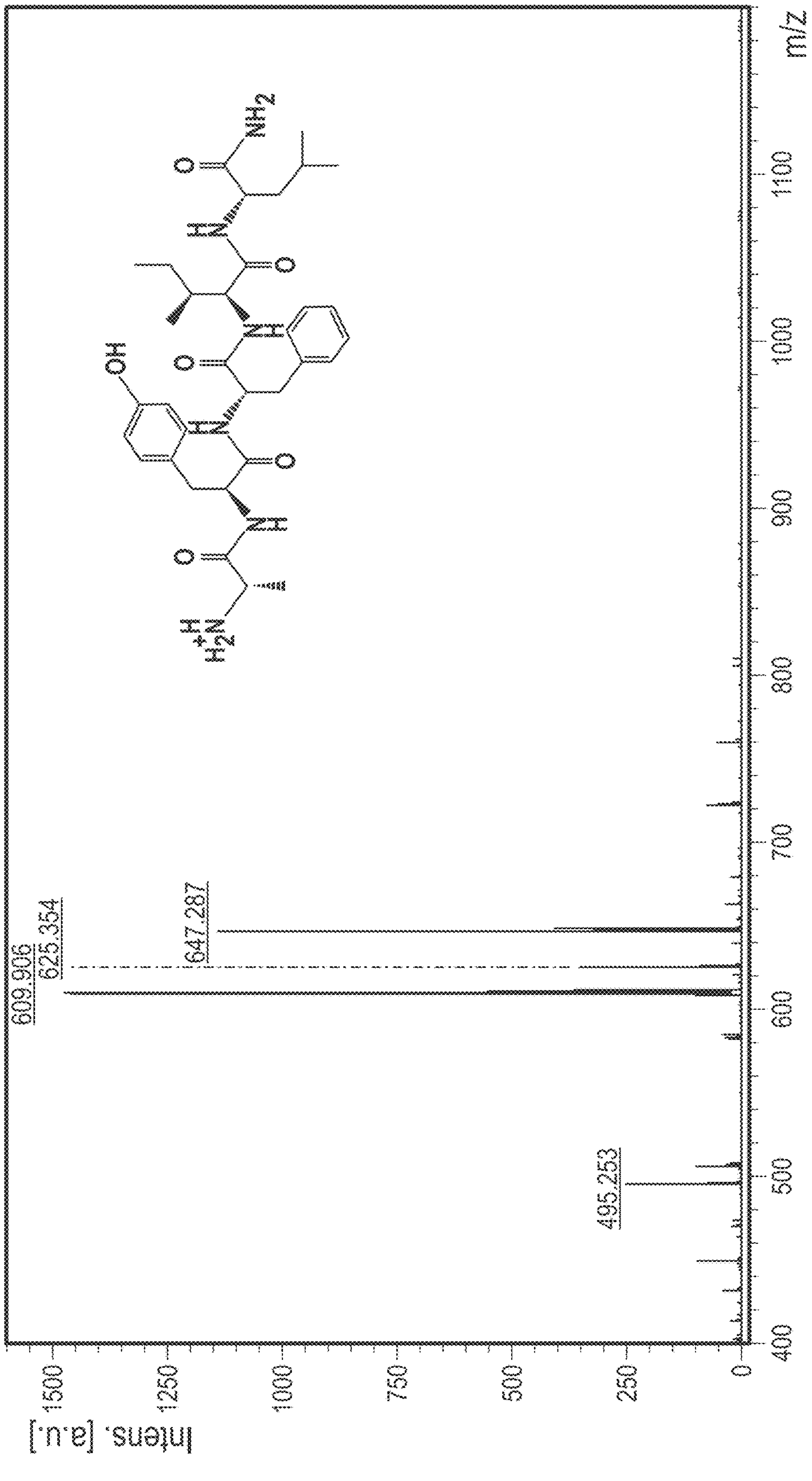
FIG. 29 depicts the MALDI-TOF MS of AYFIL peptide, with an expected mass [M+H+]+=624.77, and an observed mass=635.354.
Figure 30C:
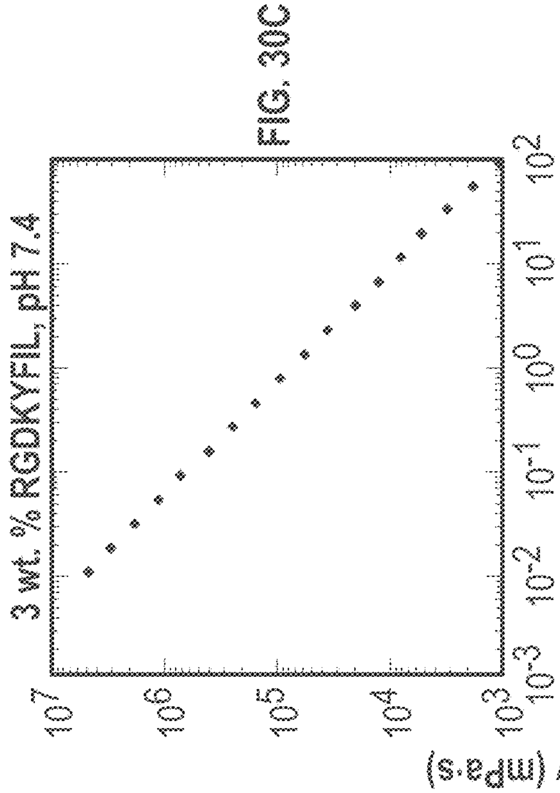
FIGS. 30A-D demonstrates the rheological characterization of RGDKYFIL (SEQ ID NO: 19). Strain sweep of RGDKYFIL at constant frequency of 1 Hz and pH 7.4 has (FIG. 30A) storage moduli of ~1000 Pa at 3 wt % and (FIG. 30B) ~100 Pa at 1.5 wt %.
Figure 30D:
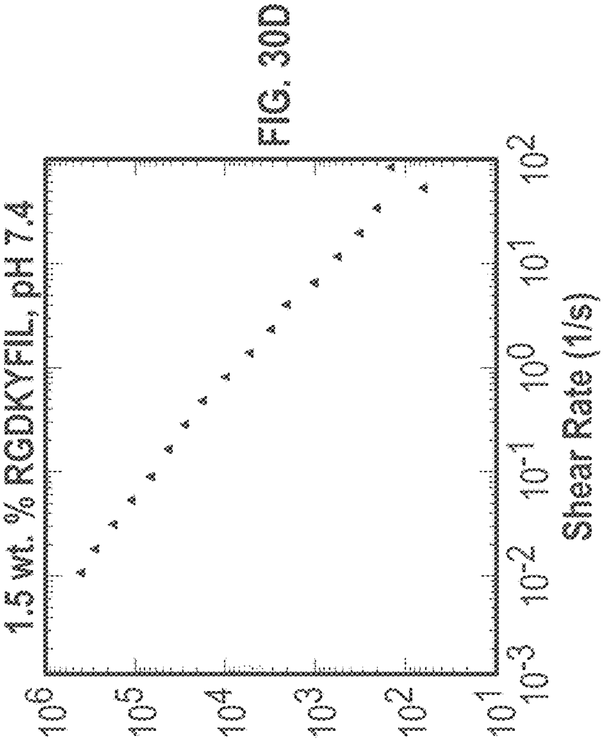
Figure 30A:
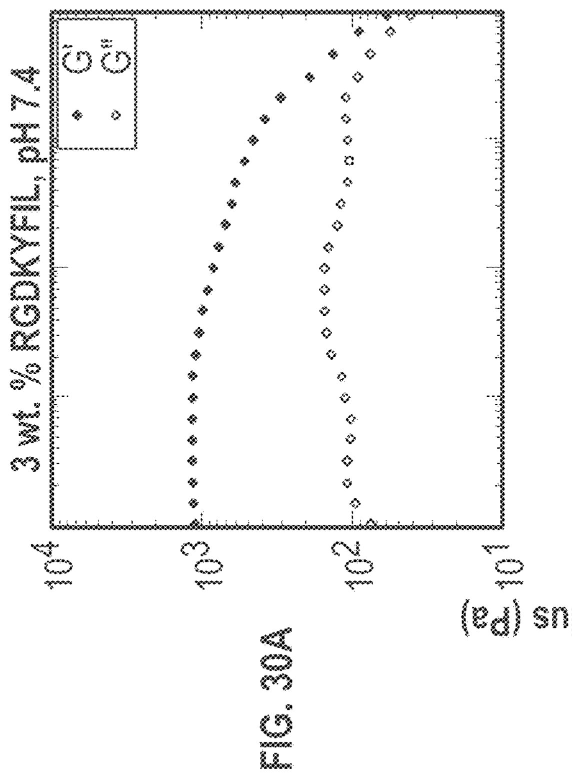
Figure 30B:
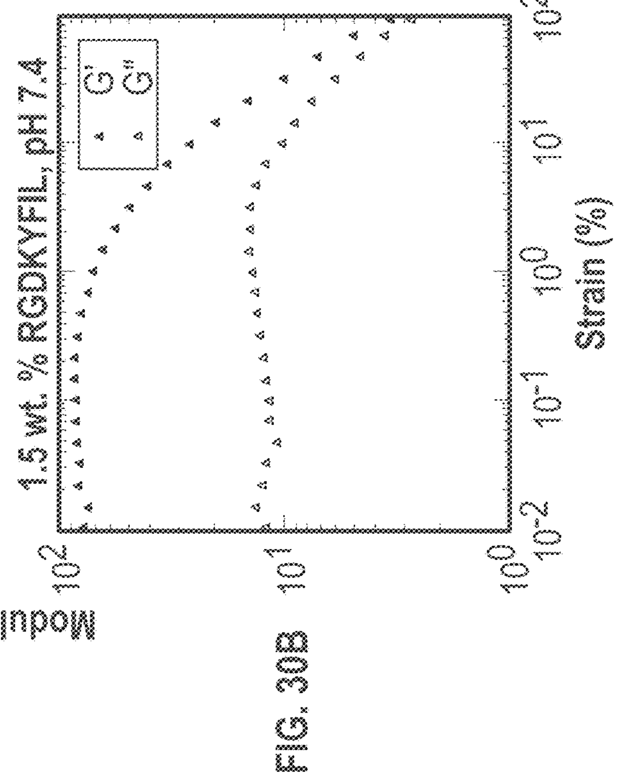

Cryo-TEM of the instantly-disclosed pentapeptide samples in vitreous ice reveals fibers that maintain twisted fiber morphologies, with finite fiber lengths up to ~100 μm (FIG. 7D). At relatively low magnification, twisted ribbons appear to pervade the hydrogel network, suggesting that these particular morphologies are not isolated, localized, or otherwise spurious instances of self-assembly (FIG. 7E). As part of an unbiased experimental design, two different batches of the KYFIL pentapeptide were independently synthesized and evaluated under TEM in order to assess the robustness and reproducibility of fibril formation. The geometric features of the fibers (helical pitch, diameter) were consistent across the two separate batches (FIG. 7F), demonstrating that these results are replicable and that there is low batch-to-batch variability as regards the peptide synthesis process, purification, and self-assembly. The periodicity of the fibrillar twist is ≈120 nm, as determined via visual analysis (FIGS. 7A-F) and by calculation of the autocorrelation function of pixel intensity along individual fibrils (FIG. 22).

Notably, both of these morphological features of our RAPID peptides—the presence of a fibrillar twist, and the ≈120 nm value of its pitch—are recapitulated in the structural features of many peptide-related systems, amyloidogenic, and otherwise. One example is β-sheet fibrils and "periodically twisted nanoribbons" formed by an Ac-NNF-GAILSS peptide from the amyloidogenic core" of islet amyloid polypeptide ($IAPP_{21-29}$). These peptides featured axial repeats of ≈85-100 nm. In a closely related system, an overlapping IAPP-derived peptide ($IAPP_{20-29}$) had AFM-characterized fibril periodicities of ≈203 nm. Fibrils from disparate proteins (e.g., SH3-containing proteins, and lysozyme) can also be polymorphic. Based on AFM studies, two subpopulations of SH3 fibrils form helical repeats of ≈105 and ≈156 nm, while human lysozyme fibrils have an "axial crossover repeat" of ≈200 nm. Perhaps most pertinent to our current study, systematic studies of a family of short peptides based on $I_3K$ (including all stereoisomeric combinations of L- and D-amino acids), showed that these amphipathic peptides form twisted fibrils with a helical pitch of ≈120 nm. This is in remarkable agreement with our RAPID fibrils, which exhibit nearly the same pitch (FIG. 7F). Though not identical to these previously characterized systems, the morphological properties of our RAPID peptide-based fibrils nevertheless are quite similar, suggesting that perhaps some unifying structural and energetic principles underlie the formation of these various supramolecular structures, amyloid-related and beyond. Most broadly, such commonalities could have overarching implications for peptide engineering and nanomaterials.

Figure 5:
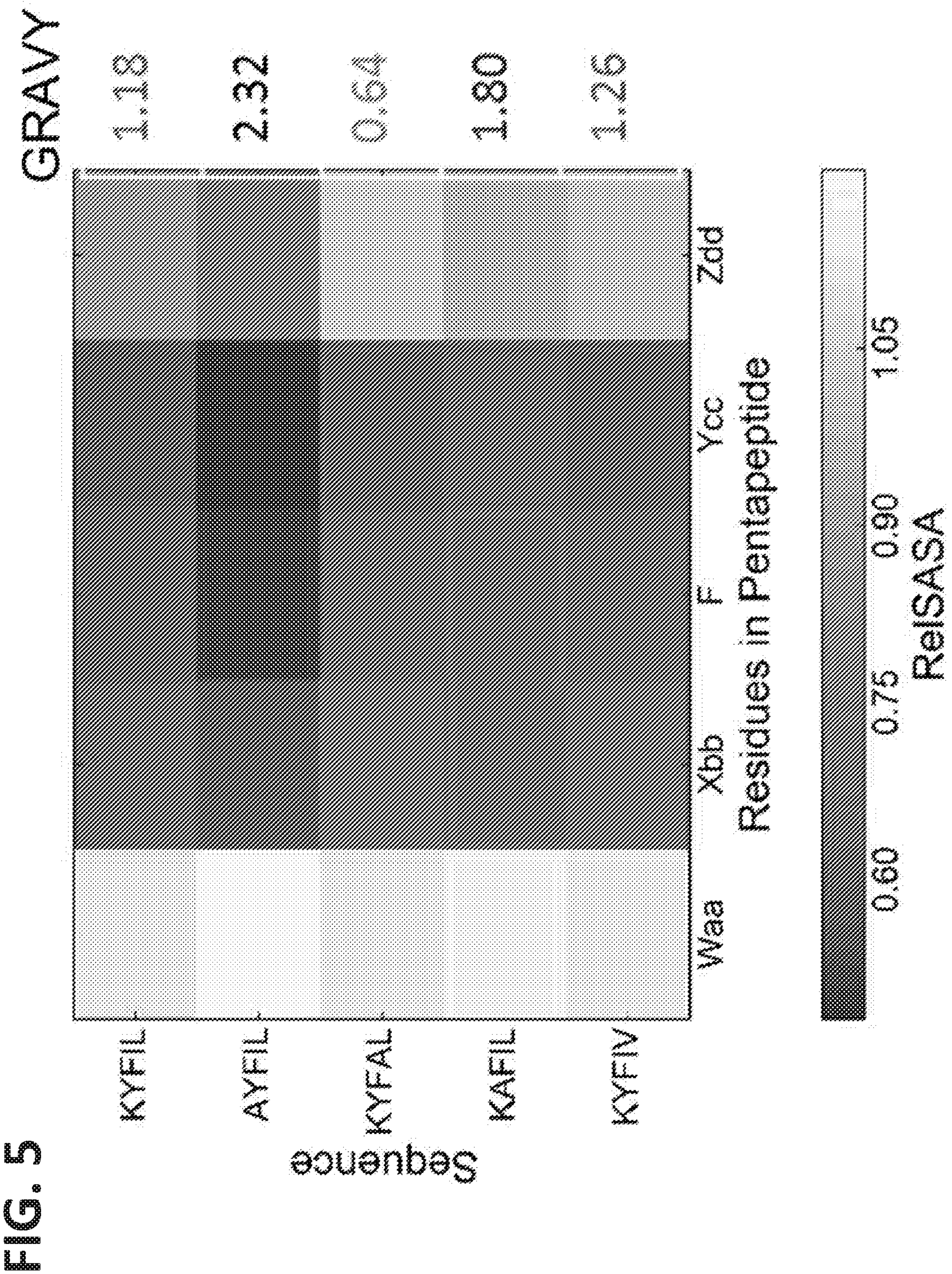
FIG. 5 is a graphical representation of sequence-dependent changes in relative solvent accessible surface areas (RelSASA) for individual residues in each pentapeptide simulation. The RelSASA quantifies the accessible surface area of each residue in the folded pentapeptide. A white color indicates that a residue is more solvent-exposed than average, while the intensity of a red color scales with residue burial. Computed grand average hydropathicity (GRAVY) values, which are essentially Kyte-Doolittle (KD) hydrophobicity indices averaged over the amino acid sequence for each peptide, are given on the right; on the KD scale, the hydrophobic amino acids have positive values (the most hydrophobic is Ile, with a value of +4.5), while hydrophilic residues have negative values (the least hydrophobic is Arg, at −4.5, followed by Lys at −3.9). At least qualitatively, the MD-based results and general hydropathicity patterns are consistent: the most hydrophobic peptide, AYFIL (most positive GRAVY score), features the least solvent exposure over the course of its MD trajectory, while the most hydrophilic peptide, KYFAL (least positive GRAVY score), exhibits the largest RelSASA values.
Figure 8:
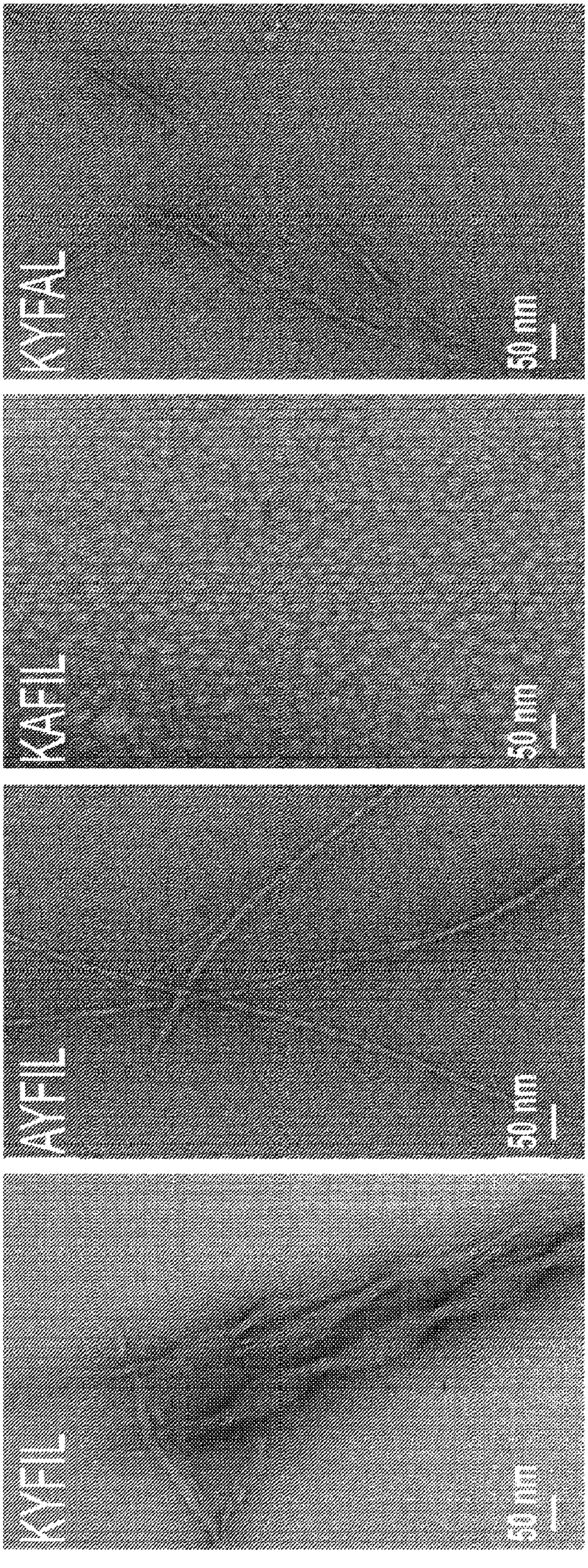
FIG. 8 shows representative TEM images of 1.5 wt % pentapeptides in PBS at pH 7.4. KYFIL hydrogels exhibit twisted ribbon morphologies, while AYFIL hydrogels are comprised of twisted fibrils. KAFIL peptide solutions at pH 7.4 form spherical aggregates (nongelling conditions), while KYFAL hydrogels also form twisted ribbon morphologies, with longer and more infrequent pitch than KYFIL peptides.

As expected, the peptide sequence has a significant effect on the nanofiber morphology. More specifically, the self-assembly of hierarchical twisted "macromolecular" structures can be altered by substituting any residue within the ••• Phe-Ile-Leu ••• moiety that detracts from the amphiphilicity of the sequence and x-system interactions. Similarly, any modification to the sequence also results in drastically different mechanical properties, as indicated in our rheology studies. We observe some twisting in nanofibers occurs within 1.5 wt % AYFIL hydrogels at pH 7.4, but the typical diameters of these fibers (≈10 nm) are significantly smaller than those of KYFIL hydrogels (≈40 nm). Though impossible to assess without more detailed analyses, a possible molecular basis for this difference relates to the sterically smaller alanine enabling a tighter packing of individual peptides within fibers or protofibers (versus the more extended Lys side-chain). For the KAFIL system under the same conditions, there is no distinct fiber formation-only spherical aggregates are seen (FIG. 8), though it should be noted that KAFIL peptides can form hydrogels at higher pH conditions. Interestingly, for KYFAL hydrogels, twisted ribbon morphologies still occur, though the persistence length of these fibers appears to be significantly shorter (based on qualitative/visual analysis), and the twist periodicity (i.e., helical pitch) is more irregular. The change in fibrillar morphology, upon an Ile→Ala substitution, may ultimately stem from an alteration in the steric properties of side chain-mediated geometric packing of peptides. While there is a great difference in length-scale between an individual peptide on the nanometer-scale and a supramolecular assembly (such as a fibril), we do see correlations between hydrophobicity properties of the different pentapeptides and the patterns of relative solvent accessibility across the different peptides, as captured by MD simulations (FIG. 5). An intriguing problem for future work is elucidation of the sequence correlates and stereochemical basis for fiber morphology (e.g., thicker ribbon diameters [≈40 nm] for KYFIL versus [≈10 nm] for KYFAL). Successfully addressing this goal will likely require an integrative, multidisciplinary, and multiscale approach, such as that used to decipher the atomic structures of cross-β amyloid fibrils of a transthyretin-derived peptide.

Cell-Protection by RAPID Hydrogels During Syringe Ejection

Figure 9:
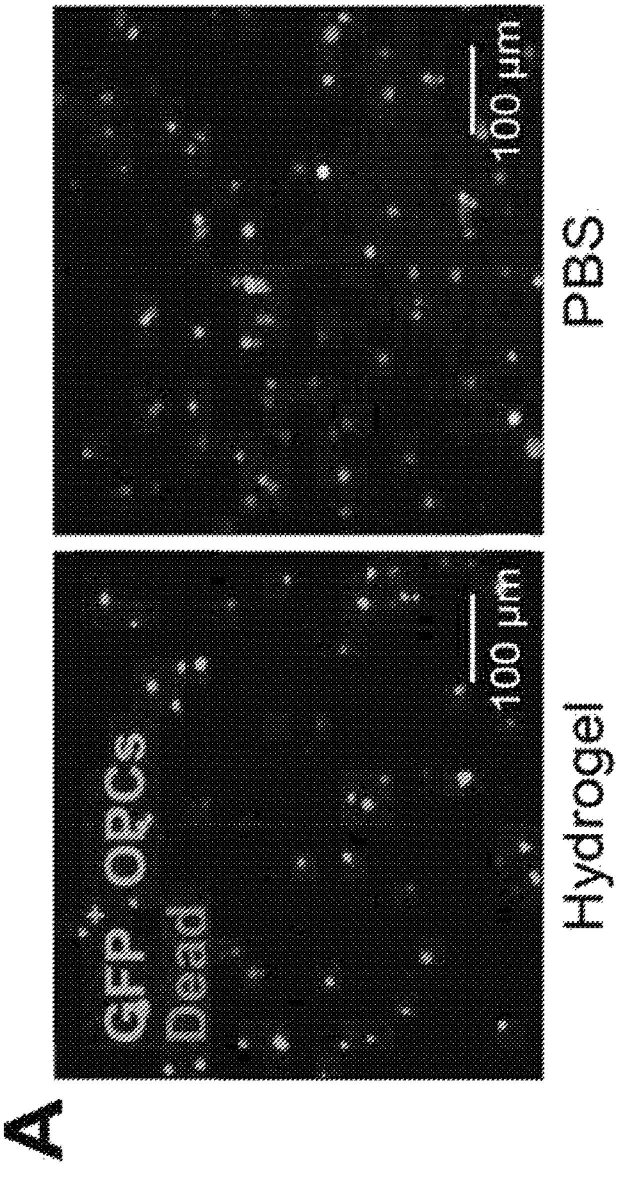
FIGS. 9A-B demonstrate viability of OPCs immediately after syringe needle flow in PBS and AYFIL hydrogels.
Figure 9:
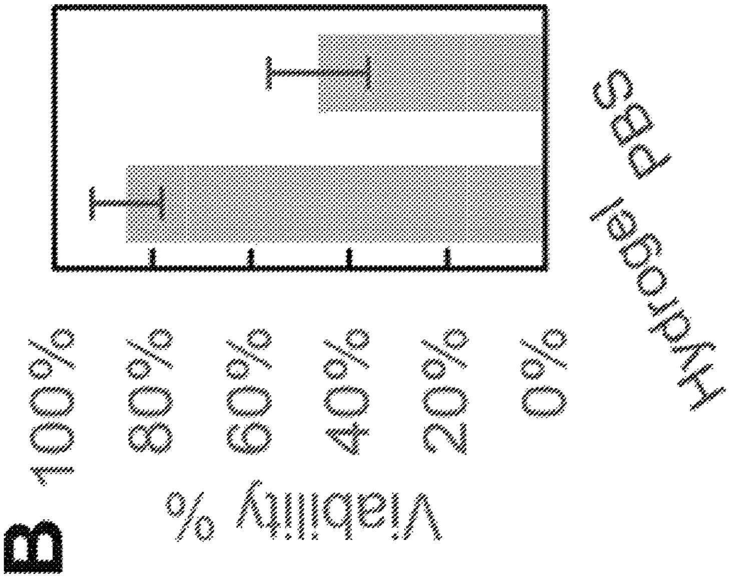

During syringe needle flow, cells can experience various types of mechanical forces that ultimately disrupt the cellular membrane: (1) extensional flow, where cells encounter stretching forces, (2) pressure drop across the cell, and (3) shear stresses, due to linear shear flow as the cell travels across the syringe. In the present study, we experimentally tested the effects of syringe needle flow on the viability of oligodendrocyte precursor cells (OPCs) suspended in PBS or RAPID hydrogels as a cell carrier at a flow rate of 1000 μL/min. OPCs are therapeutically relevant, as OPC transplantation may help circumvent the inherent regenerative limitations within the central nervous system (CNS). Indeed, this OPC transplantation strategy is currently being pursued as a therapeutic intervention in human traumatic spinal cord injury patients. When cells were ejected in PBS, OPC viability was significantly decreased compared to cells encapsulated in RAPID hydrogels and ejected ($p<0.05$, FIGS. 9A-B). Similar results were obtained with mouse myoblast (C2C12), human mesenchymal stem cells (hMSC), and primary mouse lung fibroblasts (MLF) (data not shown). This finding suggests that RAPID hydrogels could protect transplanted cells from the mechanical forces encountered during syringe needle flow and serve as valuable cell carriers in transplantation protocols.

Cytocompatibility and 3D Cell Culture Potential of RAPID Hydrogels

Mounting evidence now highlights the mechanosensitive nature of OPCs within the CNS. These lineage-restricted glial cells give rise to myelinating oligodendrocytes, and OPC proliferation and differentiation both correlate with the physical stiffness of underlying 2-D or surrounding 3-D matrices.

Figure 10:
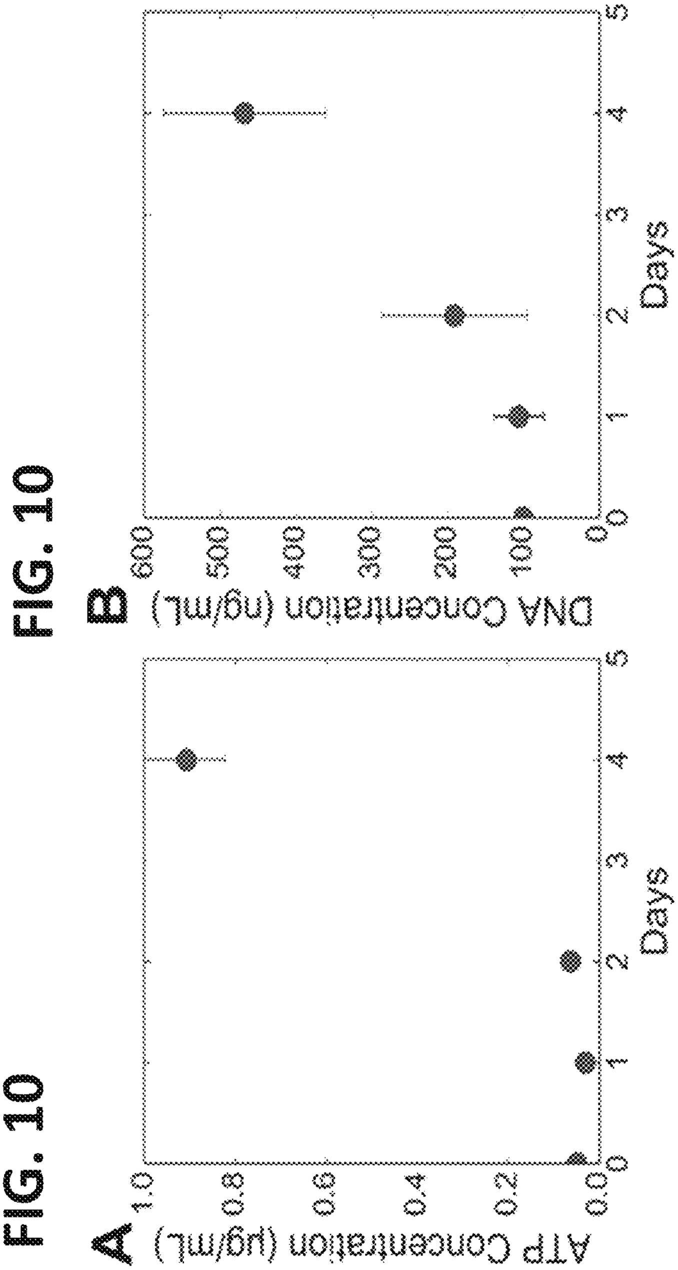
FIGS. 10A-D depict the MADM OPC line encapsulated in 1.5 wt % AYFIL hydrogels and cultured over 4 days.

The biophysical properties of hydrogels sharply influence the proliferation and differentiation of stem cells within a 3D environment. For instance, neural stem cells (NSCs) proliferate significantly more in softer substrates and preferentially differentiate into neurons in hydrogels with low moduli. Recent evidence indicates that OPCs are also sensitive to the biophysical stiffness of their surrounding microenvironment. We encapsulated OPCs in order to examine the effect of the RAPID hydrogels on viability and proliferation. OPCs survived and grew in 1.5 wt % AYFIL hydrogels (1900 Pa), as determined by the increase in both ATP and DNA concentrations over time (FIGS. 10A-B, respectively). A 1.5 wt % AYFIL hydrogel was used to investigate cytocompatibility and cell growth, as its mechanical properties (≈1900 Pa) approximate CNS tissue stiffness. Cell encapsulations with 1.5 wt % KYFIL hydrogels resulted in poor cell viability, likely due to the stiffness (≈8000 Pa) being much greater than native CNS tissue.

Figure 10C:
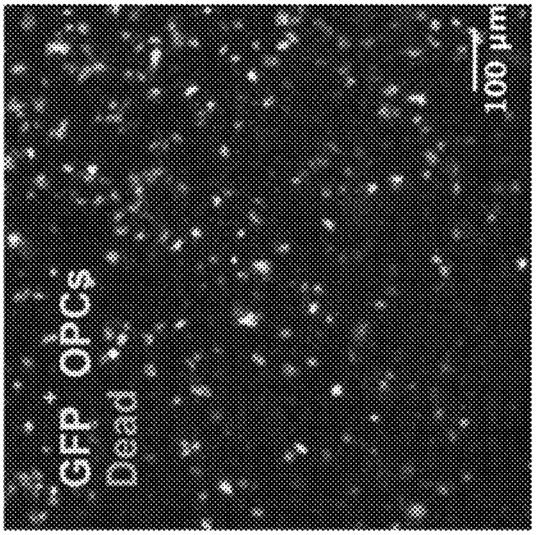
Figure 10D:
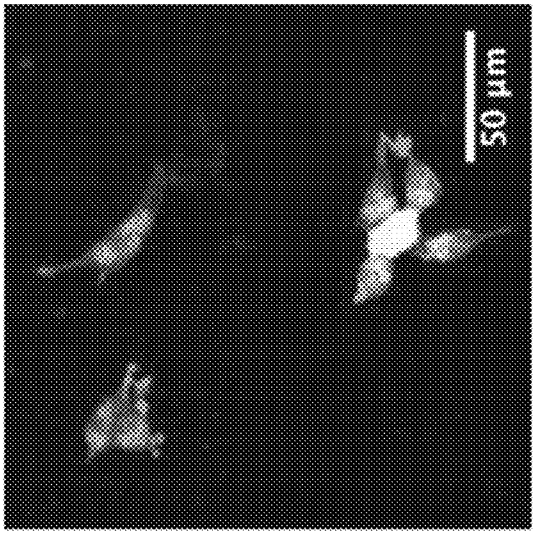

Live/dead imaging indicated a high percentage of viable cells (FIG. 10C). Others have previously shown that OPCs can extend processes within 3D poly(ethylene glycol) hydrogels after 7 days of culture, but only in the presence of laminin. Here, we demonstrate that cells within an AYFIL hydrogel can extend processes within 2 days of culture without any bioactive cellular adhesion peptide sequences or incorporating native ECM proteins (FIG. 10D and data not shown). This could be due to physical hydrogel peptide matrix being permissive of remodeling by the cells. This finding highlights that the simplicity of our cell culture system is sufficient for growth of cells derived from the CNS, without the need for laminin-derived peptide sequences as has been demonstrated in other peptide hydrogel systems.

CONCLUSIONS

The instantly-disclosed new family of short, five amino acid, peptide sequences are capable of self-assembling into robust hydrogels. We synthesized seven closely related, stimuli-responsive pentapeptide sequences. Under the conditions presented herein, four of the RAPID sequences form robust hydrogels at concentrations down to at least 1.5% (w/v). Physicochemical features of the sequence, in particular, amphiphilicity and inclusion of a central phenylalanine influence the self-assembly and β-strand formation propensities of this class of peptides. MD simulations, aimed at examining the structural properties of these β-strand-forming peptides, reveal that hydration plays an integral role in the conformational dynamics of these peptides. Experiments reveal that our hydrogels exhibit shear-thinning and self-healing properties features that may stem, at least partly, from the facile formation of β-sheet structures (in accord with our MD simulations). These rheological properties suggest the suitability of our RAPID peptides for biomedical applications requiring injection. Additionally, we observe that at physiological pH, hierarchical nanostructures (i.e., individual fibers) bundle into clearly twisted, ribbon-like morphologies. The multistranded, twisted ribbons reported here are unique among nanofiber-forming, self-assembling peptide hydrogels. We demonstrate that these self-assembling hydrogels offer effective strategies for encapsulating OPCs within 3-D matrices of tunable viscoelasticity. These scaffolds allow for cell growth and morphological process extension in OPCs. We also demonstrate that RAPID hydrogels can mitigate the damaging effects of extensional flow during syringe injections. The supramolecular assemblies formed by RAPID peptides represent injectable hydrogel systems that may offer new and translational approaches for cell delivery and tissue engineering applications.

Various modifications of the present invention, in addition to those shown and described herein, will be apparent to those skilled in the art of the above description. Such modifications are also intended to fall within the scope of the appended claims.

It is appreciated that all reagents are obtainable from commercial sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular aspects of the invention, but is not meant to be a limitation upon the practice thereof.

The invention claimed is:

1. A peptide consisting of an amino acid sequence selected from the group consisting of SEQ ID NO: 1 (KYFIL), SEQ ID NO: 2 (AYFIL), SEQ ID NO: 3 (KYFAL), SEQ ID NO: 4 (KAFIL), SEQ ID NO: 10 (KYFILKYFIL), SEQ ID NO: 11 (AYFILAYFIL), SEQ ID NO: 12 (KYFALKYFAL) and SEQ ID NO: 13 (KAFILKAFIL), wherein said peptide optionally has an uncharged C-terminus or is C-terminally amidated, wherein said peptide self-assembles and forms robust nanofiber hydrogels.

2. A peptide consisting of an amino acid sequence $(X_1\text{-}X_2\text{-F-}X_3\text{-L})_a$, wherein $X_1$ is an amino acid residue selected from the group consisting of K and A, $X_2$ is an amino acid residue selected from the group consisting of Y and A, $X_3$ is an amino acid residue selected from the group consisting of I and A, and a is 1 or 2, wherein said peptide self-assembles and forms robust nanofiber hydrogels.

* * * * *

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence

<400> SEQUENCE: 1

Lys Tyr Phe Ile Leu
1               5


<210> SEQ ID NO 2
```

```
<211> LENGTH: 5
<212> TYPE: PRT
<213> ORGANISM: Artificial Sequence
<220> FEATURE:
<223> OTHER INFORMATION: Synthetic sequence

<400> SEQUENCE: 2

Ala Tyr Phe Ile Leu
1               5


<210> SEQ ID NO 3
<211> LENGTH: 5
<212> TYPE: PRT
<213> ORGANISM: Artificial Sequence
<220> FEATURE:
<223> OTHER INFORMATION: Synthetic sequence

<400> SEQUENCE: 3

Lys Tyr Phe Ala Leu
1               5


<210> SEQ ID NO 4
<211> LENGTH: 5
<212> TYPE: PRT
<213> ORGANISM: Artificial Sequence
<220> FEATURE:
<223> OTHER INFORMATION: Synthetic sequence

<400> SEQUENCE: 4

Lys Ala Phe Ile Leu
1               5


<210> SEQ ID NO 5
<211> LENGTH: 5
<212> TYPE: PRT
<213> ORGANISM: Artificial Sequence
<220> FEATURE:
<223> OTHER INFORMATION: Synthetic sequence

<400> SEQUENCE: 5

Lys Tyr Ala Ile Leu
1               5


<210> SEQ ID NO 6
<211> LENGTH: 5
<212> TYPE: PRT
<213> ORGANISM: Artificial Sequence
<220> FEATURE:
<223> OTHER INFORMATION: Synthetic sequence

<400> SEQUENCE: 6

Lys Tyr Phe Ile Ala
1               5


<210> SEQ ID NO 7
<211> LENGTH: 5
<212> TYPE: PRT
<213> ORGANISM: Artificial Sequence
<220> FEATURE:
<223> OTHER INFORMATION: Synthetic sequence

<400> SEQUENCE: 7

Lys Tyr Phe Ile Val
1               5


<210> SEQ ID NO 8
<211> LENGTH: 5
```

```
<212> TYPE: PRT
<213> ORGANISM: Artificial Sequence
<220> FEATURE:
<223> OTHER INFORMATION: Synthetic sequence

<400> SEQUENCE: 8

Val Tyr Phe Ile Leu
1               5


<210> SEQ ID NO 9
<211> LENGTH: 5
<212> TYPE: PRT
<213> ORGANISM: Artificial Sequence
<220> FEATURE:
<223> OTHER INFORMATION: Synthetic sequence

<400> SEQUENCE: 9

Arg Tyr Phe Ile Leu
1               5


<210> SEQ ID NO 10
<211> LENGTH: 10
<212> TYPE: PRT
<213> ORGANISM: Artificial Sequence
<220> FEATURE:
<223> OTHER INFORMATION: Synthetic sequence

<400> SEQUENCE: 10

Lys Tyr Phe Ile Leu Lys Tyr Phe Ile Leu
1               5                   10


<210> SEQ ID NO 11
<211> LENGTH: 10
<212> TYPE: PRT
<213> ORGANISM: Artificial Sequence
<220> FEATURE:
<223> OTHER INFORMATION: Synthetic sequence

<400> SEQUENCE: 11

Ala Tyr Phe Ile Leu Ala Tyr Phe Ile Leu
1               5                   10


<210> SEQ ID NO 12
<211> LENGTH: 10
<212> TYPE: PRT
<213> ORGANISM: Artificial Sequence
<220> FEATURE:
<223> OTHER INFORMATION: Synthetic sequence

<400> SEQUENCE: 12

Lys Tyr Phe Ala Leu Lys Tyr Phe Ala Leu
1               5                   10


<210> SEQ ID NO 13
<211> LENGTH: 10
<212> TYPE: PRT
<213> ORGANISM: Artificial Sequence
<220> FEATURE:
<223> OTHER INFORMATION: Synthetic sequence

<400> SEQUENCE: 13

Lys Ala Phe Ile Leu Lys Ala Phe Ile Leu
1               5                   10


<210> SEQ ID NO 14
<211> LENGTH: 10
<212> TYPE: PRT
```

<213> ORGANISM: Artificial Sequence
<220> FEATURE:
<223> OTHER INFORMATION: Synthetic sequence

<400> SEQUENCE: 14

Lys Tyr Ala Ile Leu Lys Tyr Ala Ile Leu
1 5 10

<210> SEQ ID NO 15
<211> LENGTH: 10
<212> TYPE: PRT
<213> ORGANISM: Artificial Sequence
<220> FEATURE:
<223> OTHER INFORMATION: Synthetic sequence

<400> SEQUENCE: 15

Lys Tyr Phe Ile Ala Lys Tyr Phe Ile Ala
1 5 10

<210> SEQ ID NO 16
<211> LENGTH: 10
<212> TYPE: PRT
<213> ORGANISM: Artificial Sequence
<220> FEATURE:
<223> OTHER INFORMATION: Synthetic sequence

<400> SEQUENCE: 16

Lys Tyr Phe Ile Val Lys Tyr Phe Ile Val
1 5 10

<210> SEQ ID NO 17
<211> LENGTH: 10
<212> TYPE: PRT
<213> ORGANISM: Artificial Sequence
<220> FEATURE:
<223> OTHER INFORMATION: Synthetic sequence

<400> SEQUENCE: 17

Val Tyr Phe Ile Leu Val Tyr Phe Ile Leu
1 5 10

<210> SEQ ID NO 18
<211> LENGTH: 10
<212> TYPE: PRT
<213> ORGANISM: Artificial Sequence
<220> FEATURE:
<223> OTHER INFORMATION: Synthetic sequence

<400> SEQUENCE: 18

Arg Tyr Phe Ile Leu Arg Tyr Phe Ile Leu
1 5 10

<210> SEQ ID NO 19
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 19

Arg Gly Asp Lys Tyr Phe Ile Leu
1 5